(12) United States Patent
Wipf et al.

(10) Patent No.: US 9,840,515 B2
(45) Date of Patent: Dec. 12, 2017

(54) PROTEIN KINASE D INHIBITORS

(75) Inventors: Peter Wipf, Pittsburgh, PA (US); Qiming Jane Wang, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 758 days.

(21) Appl. No.: 13/992,546

(22) PCT Filed: Dec. 8, 2011

(86) PCT No.: PCT/US2011/063933
§ 371 (c)(1),
(2), (4) Date: Nov. 1, 2013

(87) PCT Pub. No.: WO2012/078859
PCT Pub. Date: Jun. 14, 2012

(65) Prior Publication Data
US 2014/0045821 A1    Feb. 13, 2014

Related U.S. Application Data

(60) Provisional application No. 61/421,403, filed on Dec. 9, 2010, provisional application No. 61/451,507, filed on Mar. 10, 2011.

(51) Int. Cl.
| | |
|---|---|
| *A61K 31/55* | (2006.01) |
| *C07D 495/04* | (2006.01) |
| *C07D 487/04* | (2006.01) |
| *C07D 491/048* | (2006.01) |
| *C07D 491/147* | (2006.01) |
| *C07D 498/04* | (2006.01) |
| *C07D 513/04* | (2006.01) |
| *C07D 513/14* | (2006.01) |

(52) U.S. Cl.
CPC ......... *C07D 495/04* (2013.01); *C07D 487/04* (2013.01); *C07D 491/048* (2013.01); *C07D 491/147* (2013.01); *C07D 498/04* (2013.01); *C07D 513/04* (2013.01); *C07D 513/14* (2013.01)

(58) Field of Classification Search
None
See application file for complete search history.

(56) References Cited

U.S. PATENT DOCUMENTS

| | | | |
|---|---|---|---|
| 5,703,069 A | 12/1997 | Connor et al. | |
| 2005/0137220 A1* | 6/2005 | Anderson et al. | 514/291 |
| 2005/0143371 A1 | 6/2005 | Meyers et al. | |
| 2011/0098325 A1* | 4/2011 | Raynham et al. | 514/352 |

FOREIGN PATENT DOCUMENTS

WO   WO 2004/098520 A2   11/2004

OTHER PUBLICATIONS

Elizabeth R. Sharlow‡§1, Karthik V. Giridhar‡1, Courtney R. LaValle‡, Jun Chen‡, Stephanie Leimgruber§, Rebecca Barrett§, Karla Bravo-Altamirano, Peter Wipf§, John S. Lazo‡§, and Q. Jane Wang The Journal of Biological Chemistry vol. 283, No. 48, pp. 33516-33526, Nov. 28, 2008.*
Alasdair MacGowan, Chris Rogers, and Karen Bowker, In Vitro Models, In Vivo Models, and Pharmacokinetics: What Can We Learn from In Vitro Models? CID 2001:33 (Suppl 3), p. S214 ohttp://cid.oxfordjournals.org/.*
Elizabeth R. Sharlow, Karthik V. Giridhar, Courtney R. LaValle, Jun Chen, Stephanie Leimgruber, Rebecca Barrett, Karla Bravo-Altamirano, Peter Wipf, John S. Lazo, and Q. Jane Wang The Journal of Biological Chemistry vol. 283, No. 48, pp. 33516-33526, Nov. 28, 2008.*
Chen, et al., Chapter 32, The use of bioisosteric groups in lead optimization in Annual Reports in Medicinal Chemlstry-38, p. 333-346. ISSN: 0065•7743; 2003 El&evier Inc.*
LaValle, C. et al, BMC Chemical Biology, 2010, 10:5. Published May 5, 2010.*
Bregman et al., J. Am. Chem. Soc. 2006, 128, 877-884.*
Rozengurt, "Protein Kinase D Signaling: Multiple Biological Functions in Health and Disease," *Physiology*, 26, pp. 23-33 (2011).
Di Fabio et al., "From Pyrroles to 1-oxo-2,3,4,9-tetrahydro-1H-β-carbolines: A new class of orally bioavailable mGluR1 Antagonists," *Bioorg. Med. Chem. Lett.*, 17, pp. 2254-2259 (2007).
Amir et al., "Synthesis of Novel S-Bridged Heterotrinuclear Complexes Containing Six-Membered Chelate Rings: Structural, Spectroscopic, and Electrochemical Properties of [Co{Rh(apt)3}2]3+(apt= 3-Aminopropanethiolate)," *Eur. J. Inorg. Chem*, pp. 1041-1049 (2006).
Sharlow et al., "Potent and Selective Disruption of Protein Kinase D Functionality by a Benzoxoloazepinolone," *J. Biol. Chem.*, 283, pp. 33516-33526 (2008).
Barral et al., "Efficient Conversion of Aromatic Amines into Azides: A One-Pot Synthesis of Triazole Linkages," *Org. let*, 9, pp. 1809-1811 (2007).
Bertolasi et al., "Structure and base catalyzed cyclization of methyl (2,6-disubstituted-4-nitrophenylsulphanyl)ethanoates," *J. Mol. Struct.* 658, pp. 33-42 (2003).
Dudova et al., "Preparation of Substituted Methyl o-Nitrophenyl Sulfides," *Molecules*, 7, pp. 7-17 (2002).
George et al., "Design Synthesis, and Biological Evaluation of PKD Inhibitors," *Pharmaceutics*, vol. 3, No. 2, pp. 186-228 (2011).

(Continued)

*Primary Examiner* — Sreeni Padmanabhan
*Assistant Examiner* — Jeanmarie Calvillo
(74) *Attorney, Agent, or Firm* — Foley & Lardner LLP

(57) ABSTRACT

Compounds according to Formula (I), are potent inhibitors of protein kinase D (pan-PKD) activity. PKD controls key signaling cascades in cells, affecting cell proliferation, gene transcription, and protein trafficking. Accordingly, pharmaceutically acceptable compositions of the inventive compounds are candidate therapeutics for pathological conditions conditioned by changes in PKD activity.

11 Claims, 3 Drawing Sheets

(56) References Cited

OTHER PUBLICATIONS

Lavalle et al., "Protein Kinase D as a Potential New Target for Cancer Therapy," *Biochimica et Biophysica Acta,* vol. 1806, No. 2, pp. 183-192 (2010).
Glushkov et al., *Dokl. Akad. Nauk,* vol. 187, pp. 327-329 (1969).
International Search Report issued in related International Patent Application No. PCT/US2011/063933, dated Jul. 17, 2012.
International Preliminary Report on Patentability issued in related International Patent Application No. PCT/US2011/063933, dated Jun. 20, 2013.

* cited by examiner

PROTEIN KINASE D INHIBITORS

CROSS-REFERENCE TO RELATED APPLICATIONS

This application is a national phase of PCT/US2011/063933, filed Dec. 8, 2011, which was published on Jun. 14, 2012, as WO 2012/078859, which claims the benefit of U.S. provisional applications No. 61/421,403, filed Dec. 9, 2010 and No. 61/451,507, filed Mar. 10, 2011. The respective contents of these applications are incorporated here by reference in their entirety.

STATEMENT REGARDING FEDERALLY SPONSORED RESEARCH

This invention was made with United States government support under grant numbers MH082038, CA129127, CA142580, MH074411 and GM067082, awarded by the National Institutes of Health. The United States government has certain rights in the invention.

BACKGROUND

The present description relates generally to the field of small molecule inhibitors of protein kinase D, collectively called "pan-PKDs." The protein kinase D (PKD) family of enzymes includes three closely related but distinct serine kinases, PKD1, PKD2 and PKD3. These three enzymes have a conserved N-terminal regulatory domain made of two cysteine rich diacylglycerol (DAG) binding motifs and an autoinhibitory pleckstrin homology (PH) domain, and a conserved C-terminal catalytic domain.

Enzymes of the PKD family are activated by signaling pathways involving the activation of gamma-phospholipase C, production of diacylglycerol and activation of protein kinase C enzymes. PKC-mediated phosphorylation of the two conserved serine residues in the catalytic domain appears to be essential for activation of PKD enzymes.

The PKD enzymes play an important role in various biological processes. For instance, PKD is implicated to play a role in lymphocyte biology, the regulation of Golgi organization in cell and in protein trafficking. It also has been proposed that PKD1 controls gene transcription via regulation of class II histone deacetylases in T-lymphocytes and cardiac cells. The role of PKD in various cellular processes such as angiogenesis, cell proliferation cellular hypertrophy, cell migration and invasion thus make members of this family of enzymes candidate therapeutic targets for the treatment of various disease conditions, including cancer, cardiac hypertrophy, and angiogenesis-related diseases.

SUMMARY

Inhibitors of the PKD family of enzymes are candidate therapeutics for the treatment of cardiac diseases and cancer. In particular, the present disclosure provides, as pan-PKD inhibitors, a class of compounds that conform to Formula I, infra. Thus, these compounds and their pharmaceutically acceptable formulations are therapeutics for treating various disease states associated with an imbalance of the PKD enzymes. The compounds and their pharmaceutical compositions also are useful in treating or preventing diseases or conditions that are associated with the expression or activity of PKD.

More specifically, the present disclosure provides compounds that conform to Formula I:

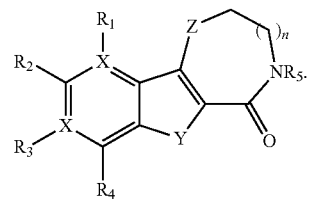

In Formula I, $R_1$, $R_2$, $R_3$, and $R_4$ are each independently selected from the group consisting of hydrogen, straight or branched chain $(C_1\text{-}C_6)$alkyl, $(C_2\text{-}C_6)$alkene, halogen, —OH, —OR', —OC(O)CH$_3$, $(C_1\text{-}C_6)$alkoxy, —N$_3$, —NR'R", isocyanate, isothiocyanate, straight or branched $(C_1\text{-}C_6)$haloalkyl and straight or branched $(C_1\text{-}C_6)$haloalkoxy. Substituent $R_5$ is selected from the group consisting of hydrogen, a straight or branched chain $(C_1\text{-}C_6)$alkyl, $(C_1\text{-}C_6)$alkylene-NH$_2$, $(C_1\text{-}C_6)$alkoxy, and —C(O)—$(C_1\text{-}C_6)$alkyl. Variable X is independently a —CR'—, or —N— and variable Y is selected from the group consisting of —O—, —S—, —S(O)— and —NR$^a$—. Variable Z is selected from the group consisting of —C(R$^d$)$_2$—, —O—, —S— and —NR"—. Subscript n is an integer between 0 and 3 inclusive, and substituent groups R', R", R$^a$, R$^b$ and R$^d$ are each independently selected from the group consisting of H, straight or branched $(C_1\text{-}C_6)$alkyl, $(C_2\text{-}C_6)$alkene, $(C_2\text{-}C_6)$alkenyloxy, halogen, —OH, —OC(O)CH$_3$, —C(O)CH$_3$, —C(O)CH$_2$-halide, straight or branched $(C_1\text{-}C_6)$haloalkyl, and benzyl.

The present description also provides a pharmaceutically acceptable salt, a stereoisomer, a tautomer and a prodrug, respectively, of any given Formula I compound. By the same token, a pharmaceutical composition is provided that comprises a therapeutically effective amount of at least one of a Formula I compound or a pharmaceutically acceptable salt, tautomer, or prodrug thereof, along with a pharmaceutically acceptable carrier.

Illustrative Formula I compounds are shown in the following table.

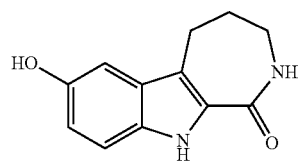 [SMILES: O=C1NCCCc2c1[nH]c1ccc(O)cc21]

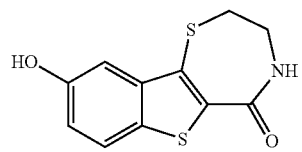

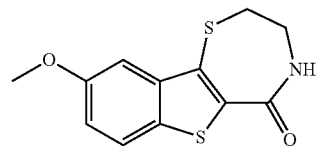 [SMILES: COc1ccc2sc3c(c2c1)SCCNC3=O]

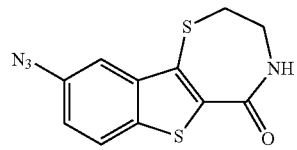 [SMILES: [N-]=[N+]=Nc1ccc2sc3c(c2c1)SCCNC3=O]
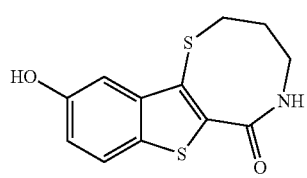 [SMILES: O=C1NCCCSc2c1sc1ccc(O)cc21]
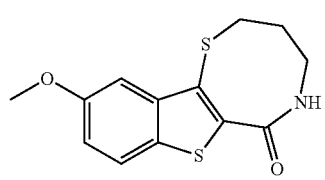 [SMILES: COc1ccc2sc3c(c2c1)SCCCNC3=O]
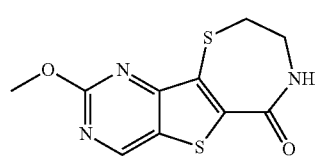 [SMILES: COc1ncc2sc3c(c2n1)SCCNC3=O]
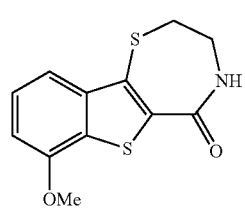 [SMILES: COc1cccc2c3c(sc12)C(=O)NCCS3]
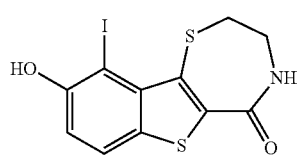 [SMILES: O=C1NCCSc2c1sc1ccc(O)c(I)c21]
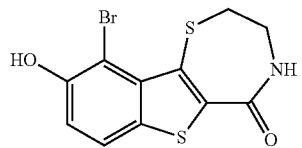 [SMILES: O=C1NCCSc2c1sc1ccc(O)c(Br)c21]
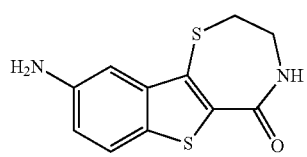 [SMILES: Nc1ccc2sc3c(c2c1)SCCNC3=O]
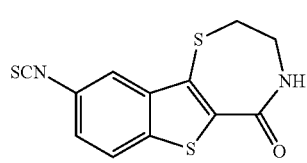
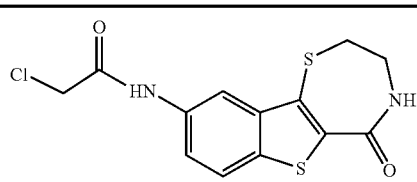
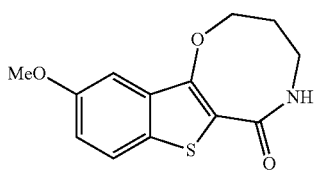 [SMILES: COc1ccc2sc3c(c2c1)OCCCNC3=O]
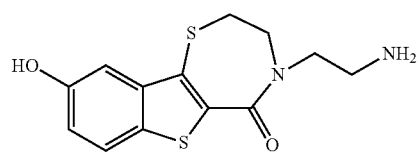 [SMILES: NCCN1CCSc2c(sc3ccc(O)cc23)C1=O]
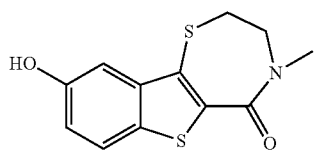 [SMILES: CN1CCSc2c(sc3ccc(O)cc23)C1=O]
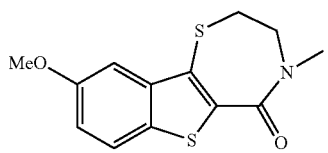 [SMILES: COc1ccc2sc3c(c2c1)SCCN(C)C3=O]
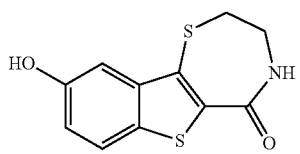
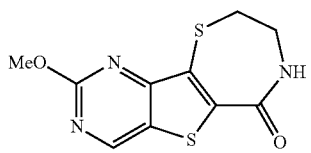
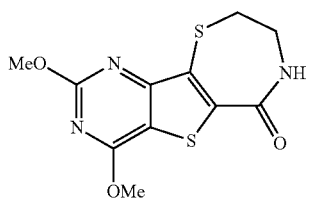
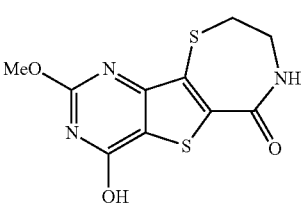 [SMILES: COc1nc(O)c2sc3c(c2n1)SCCNC3=O]

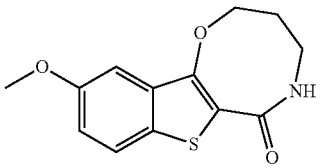 [SMILES: COc1ccc2sc3c(c2c1)OCCCNC3=O]

In one embodiment, Formula I compounds encompass thiazepinothiophenopyrimidinone analogs in which X is —N— and Z is —S—. For certain Formula I, moreover, compounds $R_1$ is —OH or methoxy. Because of their high affinity for protein kinase D, Formula I compounds having one or more electrophilic reactive functional groups are suitable agents for photoaffinity/affinity labeling of key amino acid residues within the binding pocket of a PKD. Illustrative of Formula I compounds having electrophilic reactive functional groups are those in which $R_1$ is an azide ($N_3$), an isothiocyanate (—N═C═S), or a -2-haloacetamide (—NHC(O)CH$_2$Cl).

In another embodiment, the description provides a method for inhibiting PKD1 in a cell. The method comprises contacting the cell with at least one compound according to Formula I. Pursuant to yet another embodiment, a method is provided for treating or preventing a disease or condition associated with expression or activity of PKD in a subject. According to an aspect of this embodiment, the disease or condition associated with expression or activity of PKD1 in the subject. Treatment or prevention is effected by administering to the subject a therapeutically effective amount of at least one Formula I compound or a pharmaceutically acceptable formulation thereof.

The pharmaceutical formulations described here are suitable for treating or preventing a number of diseases and conditions that have in common an association with aberrant expression and activity of PKD enzymes. Thus, a pharmaceutical formulation as described can be used in the treatment or prevention of diseases and conditions that include but are not limited to cardiac hypertrophy, cancer, and angiogenesis-related diseases.

DETAILED DESCRIPTION

Figure 1:
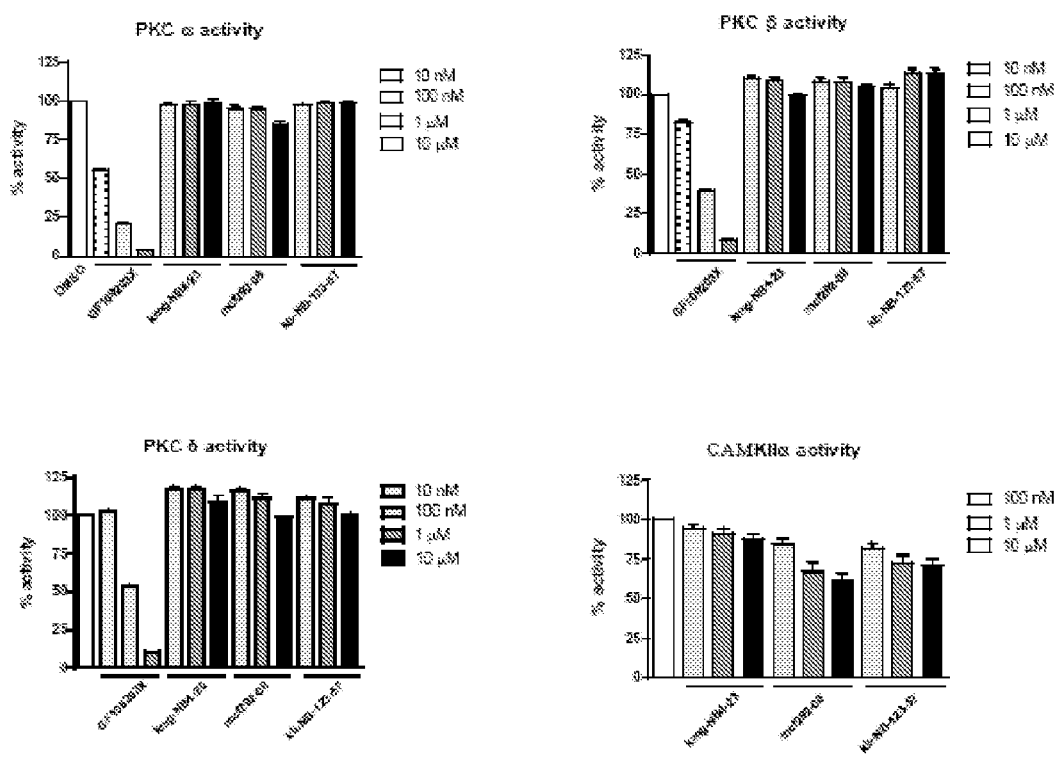
FIG. 1 is a bar graph showing the lack of inhibitory activity of certain inventive compounds against PKCα, PKCβ, PKCδ and CAMKIIα kinases.

The compounds described here are small molecule inhibitors of protein kinase D. Protein kinase D is implicated to play a central role in a number of cellular processes, including cellular signaling, cell proliferation, cell survival, activation of NF-κB and gene expression/regulation. Compounds that conform to Formula I and their pharmaceutical compositions are candidate therapeutics, therefore, in treating or preventing diseases or conditions that arise due to improper regulation of cellular processes. Illustrative of such diseases and conditions are: cancer, including cell metastasis; cardiac hypertrophy and contraction; immune function, e.g., in relation with inflammation and oxidative stress; and angiogenesis. See Rozengurt, *Physiology* 26: 23-33 (2011).

Definitions

"Alkyl" refers to straight, branched chain hydrocarbyl groups including from 1 to about 20 carbon atoms. For instance, an alkyl can have from 1 to 10 carbon atoms or 1 to 5 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, and the like. Thus, alkyl groups include primary alkyl groups, secondary alkyl groups, and tertiary alkyl groups.

The phrase "substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl.

Each of the terms "halogen," "halide," and "halo" refers to —F, —Cl, —Br, or —I.

The terms "alkylene" and "substituted alkylene" refer to divalent alkyl and divalent substituted alkyl, respectively. Examples of alkylene include without limitation, ethylene (—CH$_2$—CH$_2$—). "Optionally substituted alkylene" refers to alkylene or substituted alkylene.

"Alkene" refers to straight, branched chain, or cyclic hydrocarbyl groups including from 2 to about 20 carbon atoms having 1-3, 1-2, or at least one carbon to carbon double bond. "Substituted alkene" refers to alkene substituted at 1 or more, e.g., 1, 2, 3, 4, 5, or even 6 positions, which substituents are attached at any available atom to produce a stable compound, with substitution as described herein. "Optionally substituted alkene" refers to alkene or substituted alkene.

The term "alkenylene" refers to divalent alkene. Examples of alkenylene include without limitation, ethenylene (—CH═CH—) and all stereoisomeric and conformational isomeric forms thereof "Substituted alkenylene" refers to divalent substituted alkene. "Optionally substituted alkenylene" refers to alkenylene or substituted alkenylene.

"Alkyne or "alkynyl" refers to a straight or branched chain unsaturated hydrocarbon having the indicated number of carbon atoms and at least one triple bond. Examples of a (C$_2$-C$_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkoxy" refers to an —O-alkyl group having the indicated number of carbon atoms. For example, a ($C_1$-$C_6$)alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "alkenyloxy" refers to an —O-alkene group having the indicated number of carbon atoms. For example, a ($C_2$-$C_6$)alkenyloxy group includes —Oethene, allyloxy, or prop-1-ene-3-oxy, 2-methylprop-1-ene-3-oxy and but-1-ene-4-oxy.

The term "aryl," alone or in combination refers to a ($C_3$-$C_{14}$) aromatic monocyclic or bicyclic ring system such as phenyl or naphthyl. "Aryl" also includes aromatic ring systems that are optionally fused with a cycloalkyl ring as herein defined.

A "substituted aryl" is an aryl that is independently substituted with one or more substituents attached at any available atom to produce a stable compound, wherein the substituents are as described herein. "Optionally substituted aryl" refers to aryl or substituted aryl.

"Arylene" denotes divalent aryl, and "substituted arylene" refers to divalent substituted aryl. "Optionally substituted arylene" refers to arylene or substituted arylene.

The term "sulfoxide" refers to a compound in which the sulfinyl group (—(SO)—), is attached to two carbon atoms. The —S(O)— group together with the two carbons to which it is attached can form a 5-, or 6-membered ring.

The term "araalkyl," "araalkylene," or ($C_3$-$C_{14}$)aryl-($C_1$-$C_6$)alkylene refers to a divalent ($C_1$-$C_6$) alkylene group in which one or more hydrogen atoms in the ($C_1$-$C_6$)alkylene group is replaced by an ($C_3$-$C_{14}$)aryl group. Exemplary are benzyl, 1-phenylbutylene, phenyl-2-butylene, 1-phenyl-2-methylpropylene and naphthylethylene.

The term "heteroatom" refers to N, O, and S. Inventive compounds that contain N or S atoms can be optionally oxidized to the corresponding N-oxide, sulfoxide or sulfone compounds.

"Heteroaryl," alone or in combination with any other moiety described herein, refers to a monocyclic aromatic ring structure containing 5 or 6 ring atoms, or a bicyclic aromatic group having 8 to 10 atoms, containing one or more, such as 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl.

A "substituted heteroaryl" is a heteroaryl that is independently substituted, unless indicated otherwise, with one or more, e.g., 1, 2, 3, 4 or 5, also 1, 2, or 3 substituents, also 1 substituent, attached at any available atom to produce a stable compound, wherein the substituents are as described herein. "Optionally substituted heteroaryl" refers to heteroaryl or substituted heteroaryl.

"Heteroarylene" refers to divalent heteroaryl, and "substituted heteroarylene" refers to divalent substituted heteroaryl. "Optionally substituted heteroarylene" refers to heteroarylene or substituted heteroarylene.

"Heterocycloalkyl" means a saturated or unsaturated non-aromatic monocyclic, bicyclic, tricyclic or polycyclic ring system that has from 5 to 14 atoms in which from 1 to 3 carbon atoms in the ring are replaced by heteroatoms of O, S or N. A heterocycloalkyl is optionally fused with benzo or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl.

"Optionally substituted heterocycloalkyl" denotes heterocycloalkyl that is substituted with 1 to 3 substituents, e.g., 1, 2 or 3 substituents, attached at any available atom to produce a stable compound, wherein the substituents are as described herein.

"Heteroalkyl" means a saturated alkyl group having from 1 to about 20 carbon atoms, 1 to 10 carbon atoms, 1 to 6 carbon atoms, or 1 to 3 carbon atoms, in which from 1 to 3 carbon atoms are replaced by heteroatoms of O, S or N. Heteroalkyl is also intended to include oxidized S or N, such as sulfinyl, sulfonyl and N-oxide of a tertiary ring nitrogen. The point of attachment of the heteroalkyl substituent is at an atom such that a stable compound is formed. Examples of heteroalkyl groups include, but are not limited to, N-alkylaminoalkyl (e.g., $CH_3NHCH_2$—), N,N-dialkylaminoalkyl (e.g., $(CH_3)_2NCH_2$—), and the like.

"Heteroalkylene" refers to divalent heteroalkyl. The term "optionally substituted heteroalkylene" refers to heteroalkylene that is substituted with 1 to 3 substituents, e.g., 1, 2 or 3 substituents, attached at any available atom to produce a stable compound, wherein the substituents are as described herein.

"Heteroalkene" means a unsaturated alkyl group having from 1 to about 20 carbon atoms, 1 to 10 carbon atoms, 1 to 6 carbon atoms, or 1 to 3 carbon atoms, in which from 1 to 3 carbon atoms are replaced by heteroatoms of O, S or N, and having 1-3, 1-2, or at least one carbon to carbon double bond or carbon to heteroatom double bond.

"Heteroalkenylene" refers to divalent heteroalkene. The term "optionally substituted heteroalkenylene" refers to heteroalkenylene that is substituted with 1 to 3 substituents, e.g., 1, 2 or 3 substituents, attached at any available atom to produce a stable compound, wherein the substituents are as described herein.

The term "cycloalkyl" refer to monocyclic, bicyclic, tricyclic, or polycyclic, 3- to 14-membered ring systems, which are either saturated, unsaturated or aromatic. The heterocycle may be attached via any atom. Cycloalkyl also contemplates fused rings wherein the cycloalkyl is fused to an aryl or hetroaryl ring as defined above. Representative examples of cycloalkyl include, but are not limited to cyclopropyl, cycloisopropyl, cyclobutyl, cyclopentyl, cyclohexyl, cyclopropene, cyclobutene, cyclopentene, cyclohexene, phenyl, naphthyl, anthracyl, benzofuranyl, and benzothiophenyl. A cycloalkyl group can be unsubstituted or optionally substituted with one or more substituents as described herein below.

The term "cycloalkylene" refers to divalent cycloalkylene. The term "optionally substituted cycloalkylene" refers to cycloalkylene that is substituted with 1 to 3 substituents, e.g., 1, 2 or 3 substituents, attached at any available atom to produce a stable compound, wherein the substituents are as described herein.

The term 'nitrile or cyano" can be used interchangeably and refer to a —CN group which is bound to a carbon atom of a heteroaryl ring, aryl ring and a heterocycloalkyl ring.

The term "oxo" refers to a =O atom attached to a saturated or unsaturated ($C_3$-$C_8$) cyclic or a ($C_1$-$C_8$) acyclic moiety. The =O atom can be attached to a carbon, sulfur, and nitrogen atom that is part of the cyclic or acyclic moiety.

The term "amine or amino" refers to an —NR'R" group wherein R' and R" each independently refer to a hydrogen, ($C_1$-$C_8$)alkyl, aryl, heteroaryl, heterocycloalkyl, ($C_1$-$C_8$)haloalkyl, and ($C_1$-$C_6$)hydroxyalkyl group.

The term "amide" refers to a —NR'R"C(O)— group wherein R' and R" each independently refer to a hydrogen, ($C_1$-$C_8$)alkyl, or ($C_3$-$C_6$)aryl, heteroaryl, heterocycloalkyl, ($C_1$-$C_8$)haloalkyl, and ($C_1$-$C_6$)hydroxyalkyl group.

The term "aryloxy" refers to an —O-aryl group having the indicated number of carbon atoms. Examples of aryloxy groups include, but are not limited to, phenoxy, napthoxy and cyclopropeneoxy.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof.

The term "aminoalkyl," refers to an ($C_1$-$C_6$)alkyl group wherein one or more hydrogen atoms in the $C_1$-$C_6$ alkyl group is replaced with a —$NR^dR^e$ group, where $R^d$ and $R^e$ can be the same or different, for example, $R^d$ and $R^e$ each independently refer to a hydrogen, ($C_1$-$C_8$)alkyl, aryl, heteroaryl, heterocycloalkyl, ($C_1$-$C_8$)haloalkyl, and ($C_1$-$C_6$) hydroxyalkyl group. Examples of aminoalkyl groups include, but are not limited to, aminomethyl, aminoethyl, 4-aminobutyl and 3-aminobutylyl.

The term "thioalkyl" or "alkylthio" refers to a ($C_1$-$C_6$) alkyl group wherein one or more hydrogen atoms in the $C_1$-$C_6$ alkyl group is replaced with a —$SR^j$ group, wherein $R^j$ is selected from the group consisting of hydrogen, ($C_1$-$C_6$)alkyl and ($C_3$-$C_{14}$)aryl.

The term "haloalkyl," refers to an alkyl group having the indicated number of carbon atoms wherein one or more of the alkyl group's hydrogen atoms is replaced with a halogen (X), for instance, a chlorine, a fluorine, a bromine or a iodine atom which can be the same or different. Examples of haloalkyl groups include, but are not limited to, —$CH_2X$, —$CH_2CH_2X$, —$CH_2CH_2CH_2X$, —$CH_2CH_2CH_2CH_2X$, —$CH_2CH_2CH_2CH_2CH_2X$, —$CH_2CH_2CH_2CH_2CH_2CH_2X$, and branched versions thereof.

The term "haloalkoxy," refers to an alkoxy group having the indicated number of carbon atoms wherein one or more of the alkyl group's hydrogen atoms are replaced with a halogen (X), for instance, a chlorine, a fluorine, a bromine or a iodine which can be the same or different. Examples of haloalkyl groups include, but are not limited to, —$OCH_2X$, —$OCH_2CH_2X$, —$OCH_2CH_2CH_2X$, —$OCH_2CH_2CH_2CH_2X$, —$OCH_2CH_2CH_2CH_2CH_2X$, —$OCH_2CH_2CH_2CH_2CH_2CH_2X$, and branched versions thereof.

"Amino ($C_1$-$C_6$)alkylene" refers to a divalent alkylene wherein one or more hydrogen atoms in the $C_1$-$C_6$ alkylene group is replaced with a —$NR^dR^e$ group. Examples of amino ($C_1$-$C_6$)alkylene include, but are not limited to, aminomethylene, aminoethylene, 4-aminobutylene and 3-aminobutylylene.

An "isocyanate" refers to a group of formula R—N=C=O, where R can be a ($C_1$-$C_{10}$) alkyl, ($C_3$-$C_{14}$) aryl, ($C_3$-$C_{14}$) heteroaryl, ($C_3$-$C_{14}$) cycloalkyl, or a ($C_3$-$C_{14}$) heterocycloalkyl.

An "isothiocyanate" refers to a group of formula R—N=C=S, where R can be a ($C_1$-$C_{10}$) alkyl, ($C_3$-$C_{14}$) aryl, ($C_3$-$C_{14}$) heteroaryl, ($C_3$-$C_{14}$) cycloalkyl, or a ($C_3$-$C_{14}$) heterocycloalkyl.

A "hydroxyl" or "hydroxy" refers to an —OH group.

A "thiol" refers to an —SH group.

The term "thione" refers to a —C=S group attached to a saturated or unsaturated ($C_3$-$C_8$) cyclic or a ($C_1$-$C_8$) acyclic moiety.

The term "azide" refers to a —$N_3$ group attached to a saturated or unsaturated ($C_3$-$C_8$) cyclic or a ($C_1$-$C_8$) acyclic moiety.

The term "($C_3$-$C_{14}$)aryl-($C_1$-$C_6$)alkylene" refers to a divalent alkylene wherein one or more hydrogen atoms in the $C_1$-$C_6$ alkylene group is replaced by a ($C_3$-$C_{14}$)aryl group. Examples of ($C_3$-$C_{14}$)aryl-($C_1$-$C_6$)alkylene groups include without limitation 1-phenylbutylene, phenyl-2-butylene, 1-phenyl-2-methylpropylene, phenylmethylene, phenylpropylene, and naphthylethylene.

The term "($C_3$-$C_{14}$)heterocycloalkyl-($C_3$-$C_{14}$)heterocycloalkylene" refers to a divalent heterocycloalkylene wherein one or more hydrogen atoms in the $C_3$-$C_{14}$ heterocycloalkylene group is replaced by ($C_3$-$C_{14}$)heterocycloalkyl group. Exemplary of the ($C_3$-$C_{14}$)heterocycloalkyl-($C_3$-$C_{14}$)heterocycloalkylene group is 3-Piperidin-1-yl-1,5, 6,7-tetrahydroazepin-2-one.

The substituent —$CO_2H$, may be replaced with bioisosteric replacements such as:

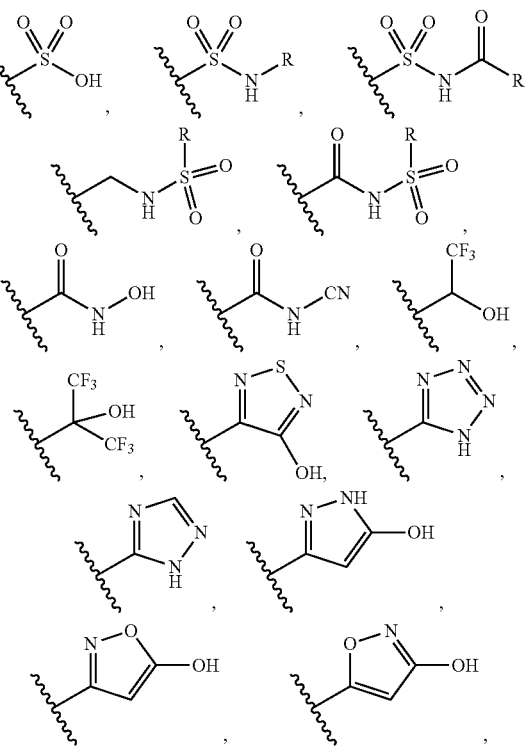

-continued

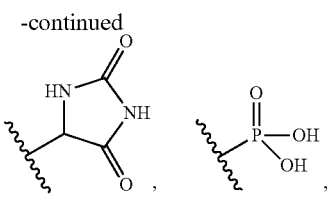

and the like, wherein R has the same definition as R' and R" as defined herein. See, e.g., THE PRACTICE OF MEDICINAL CHEMISTRY (Academic Press: New York, 1996), at page 203.

The compound of the invention can exist in various isomeric forms, including configurational, geometric, and conformational isomers, including, for example, cis- or trans-conformations. Compounds of the present invention may also exist in one or more tautomeric forms, including both single tautomers and mixtures of tautomers. The term "isomer" is intended to encompass all isomeric forms of a compound of this invention, including tautomeric forms of the compound.

If compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, simulated moving bed technology or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

A "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The phrases "effective amount" and "therapeutically effective amount" refer to an amount of a compound of the invention or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy of or synergies with another therapeutic agent.

The terms "inhibit," "inhibition" and the like refer to the ability of a compound to decrease the function, or activity of, for example, PKD1. PKD inhibitors are compounds that, e.g., bind to, partially or totally block activity of PKD, its ability to regulate gene transcription, protein trafficking, and regulate Golgi organiztion. The ability of a compound to inhibit PKD activity can be demonstrated using an enzyme kinetic assay.

A "patient" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

Compounds

The compounds of this description are small molecule inhibitors of PKD. Specifically, the compounds belong to a class represented by Formula I:

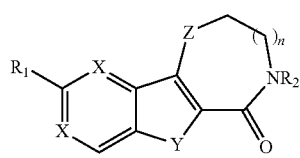

The present inventors used structure-activity relationship studies (SAR), to identify compounds that have increased selectivity and potency for PKD than the known PKD inhibitor CID755673.

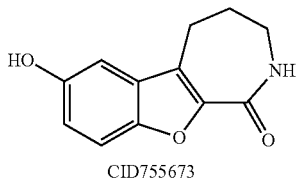 [SMILES: O=C1NCCCc2c1oc1ccc(O)cc21]

CID755673

CID755673 selectively inhibits PKD over protein kinase-C (PKC), with $IC_{50}$ values for the three isoforms of PKD, namely, PKD1, PKD2 and PKD3, being in the range from about 180 nM to about 300 nM.

To study which regions of CID755673 take part in inhibition of PKD1, the present inventors dissected CID755673 into four separate structural zones as illustrated below. More specifically, the inventors synthesized and tested CID755673 derivatives to identify which substituent groups increase potency and/or specificity of the CID755673 derivatives for PKD1.

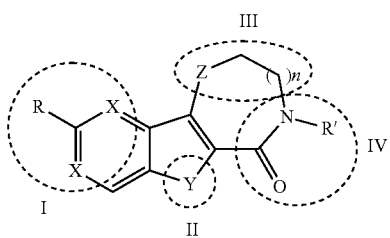

In the context of the present invention, therefore, the term "derivative" refers to a compound that is derived from a similar compound or a compound that can be imagined to arise from another compound, if one atom is replaced with another atom or group of atoms.

SAR trends deduced from analysis of a series of CID755673 derivatives indicate that for zone I compounds, the introduction of a substituent group ortho- to the phenolic —OH group of CID755673 decreased binding to PKD1, expect for ortho-halo derivatives which had similar binding affinity to PKD1 as CID755673. Exemplary Formula I compounds that have a substituent group ortho- to the phenolic —OH are shown below in Table 1.

TABLE 1

Chemical structures and PKD1 inhibitory activities of CID755673 analogs.

| | | | | | | $IC_{50}$ IMAP-FP PKD1 | radiometric |
|---|---|---|---|---|---|---|---|
| Entry | Compound | Z | $R^1$ | $R^2$ | $R^3$ | (μM) | PKD1 (μM) |
| 1 | kb-NB77-88 | $CH_2$ | Cl | OH | H | 1.4 ± 0.1 (n = 3) | 0.89 (n = 1) |
| 2 | kb-NB96-21 | $CH_2$ | F | OH | H | 1.3 ± 0.05 (n = 3) | 0.24 (n = 1) |
| 3 | kb-NB96-50 | $CH_2$ | Cl | OAllyl | H | not inhibitory | n.d. |
| 4 | kb-NB96-47-5 | $CH_2$ | H | OH | Cl | >100 | n.d. |
| 5 | kb-NB96-43 | $CH_2$ | Cl | OH | Cl | not inhibitory | n.d. |
| 6 | kb-NB96-02 | $CH_2$ | Allyl | OH | H | 2.4 ± 0.3 (n = 3) | 1.58 (n = 1) |
| 7 | kb-NB96-30 | $CH_2$ | Propenyl | OH | H | 1.0 ± 0.1 (n = 3) | 0.24 (n = 1) |
| 8 | kb-NB123-63 | C=O | H | OH | H | 14.9 ± 1.2 (n = 3) | 0.85 ± 0.11 (n = 2) |
| 9 | kb-NB123-89 | CHOH | H | OH | H | 24.09 ± 0.71 (n = 3) | 1.23 ± 0.21 (n = 2) |
| 10 | kb-NB142-05 | C=NNHPh | H | OH | H | 21.70 ± 0.52 (n = 3) | 1.13 (n = 1) |
| 11 | kb-NB142-11 | C=NNHTs | H | OH | H | 38.21 ± 1.17 (n = 3) | n.d. |
| 12 | kb-NB142-10 | C=NOBn | H | OH | H | not inhibitory | n.d. |

Furthermore, derivatization of the zone I phenolic group to form the corresponding O-ether derivatives changed binding affinity depending on the nature and size of the substituent group. Thus, the O-benzyl ether derivative had a lower activity, that is, decreased potency to inhibit PKD1 than CID755673, (see $IC_{50}$ for the O-derivatives in Table 2), while the less bulky O-methyl derivative inhibits PKD1 more potently with an ex vivo $IC_{50}$ of 82.5 nM. The O-methyl ether kb-NB165-09, however, exhibited lower inhibitory activity than the corresponding hydroxyl analog (kb-NB142-70). The approximately three fold loss in activity indicates that hydrogen bonding interactions between the active site zone I amino acid residues and the phenolic —OH group are less important in binding within the zone I pocket. Similar decreases in inhibitory activity were observed for the O-allyl, O-acetyl and the tert-butylsilyl analogs in comparison to the phenolic analog kb-NB142-70.

Based on the results from SAR studies, particularly in view of differences in the PKD1 inhibition potencies of the O-methyl and O-benzyl derivatives of CID755673, the inventors have hypothesized that the loss of inhibitory activity for the O-benzyl derivative implicates that the zone I pocket of PKD1 is unable to accommodate bulky substituent groups and is sterically limiting. Comporting with this analysis, and as shown by data in Table 2, the azido analog mcf292-08, of Formula I is a stronger inhibitor than the —Obenzyl analog with an $IC_{50}$ of 74.9 nM.

TABLE 2

| Zone | Compound | Structure | | | | | | IC$_{50}$ | |
|---|---|---|---|---|---|---|---|---|---|
| | | X | Y | Z | R$_2$ | N | R$_5$ | PKD1 (nM)[a] | Cellular PKD1 (μM)[b] |
| — | CID755673 | CH | O | CH$_2$ | OH | 1 | H | 182 ± 27 (n = 5) | 11.8 ± 4.0 (n = 3) |
| II | kb-NB123-57 | CH | NH | CH$_2$ | OH | 1 | | 130 ± 14 (n = 3) | nd |
| II, III | kb-NB142-70 | CH | S | S | OH | 1 | H | 28.3 ± 2.3 (n = 3) | 2.2 ± 0.6 (n = 3) |
| I, II, III | kb-NB165-09 | CH | S | S | OMe | 1 | H | 82.5 ± 4.6 (n = 4) | 3.1 ± 0.5 (n = 3) |
| I, II, III | kb-NB123-66 | CH | S | S | OBn | 1 | H | n.d. | n.d. |
| I | mcf292-08 | CH | S | S | N$_3$ | 1 | H | 74.9 ± 14.8 (n = 5) | 2.2 ± 0.2 (n = 3) |
| III | kb-NB165-92 | CH | S | S | OH | 2 | H | 111 ± 6 (n = 3) | 2.6 ± 0.7 (n = 2) |
| III | kb-NB184-02 | CH | S | S | OMe | 2 | H | 193 ± 27 (n = 3) | 18.6 ± 2.0 (n = 3) |
| I | kmg-NB4-23 | N | S | S | OMe | 1 | H | 124 ± 31 (n = 4) | 6.8 ± 1.3 (n = 3) |
| I | kb-NB77-84 | CH | O | CH | Oallyl | 1 | H | 123 | n.d. |
| I | kb-NB77-77 | CH | O | CH | OTBS | 1 | H | n.d | n.d. |
| I | kb-NB77-36 | CH | O | CH | OAc | 1 | H | n.d | n.d. |
| I & IV | kb-NB123-37 | CH | O | CH | OMe | 0 | Me | n.d | n.d. |
| I & IV | kb-NB142-25 | CH | O | CH | OH | 1 | Me | 4.0 ± 1.1 (n = 2) | n.d. |
| I & IV | kb-NB96-04 | CH | O | CH | OMe | 1 | Me | n.d | n.d. |
| I & IV | kb-NB123-45-1 | CH | O | CH | OAc | 1 | OAc | n.d. | n.d. |
| I | kb-NB123-23A | CH | O | CH | OH | 0 | H | | |
| I | kb-NB123-32 | CH | O | CH | OMe | 0 | H | | |
| I | kb-NB96-53 | CH | O | CH | OH | 2 | H | | |
| I | kb-NB96-59 | CH | O | CH | OMe | 2 | H | | |
| I | kb-NB77-56 | CH | O | CH | OMe | 1 | H | | |
| I & IV | kb-NB165-15 | | | | | | | No inhibition | n.d. |

[a] PKD1 IC$_{50}$ was determined using a radiometric kinase activity assay as previously described.[20] Each IC$_{50}$ was calculated as the mean ± S.E.M. of at least three independent experiments with triplicate determinations at each concentration in each experiment; n = number of independent experiments. [b] Cellular IC$_{50}$ was determined by densitometry analysis of Western blotting data for PKD1 autophosphorylation at S916 in LNCaP cells as previously described. 21 Each IC$_{50}$ was calculated as the mean ± S.E.M. of at least two independent experiments; n = number of independent experiments; n.d. = not determined.

The present inventors also explored the effect on binding to PKD's for Formula I compounds having a substituent group ortho to the sulfur of the thiophene ring. As illustrated by data in Table 2A, substitutions at the ortho R$^4$ position lowered PKD1 inhibitory activity in vitro (Table 2A, entries 7-9). Without necessarily implicating any particular theory, this result suggests a sterically limiting nature of the zone I binding pocket in PKDs.

In contrast, introducing a halogen ortho to the phenolic —OH (Table 2A, entries 5 and 6), or replacement of the phenolic hydroxy group with amine variants (Table 2A, entries 1-4) were surprisingly well tolerated. For example, the ortho-iodinated analog, kb-NB165-31, was a potent inhibitor with an IC$_{50}$ value of 114 nM; however, its cellular activity was 4-fold lower than that of the unhalogenated analog kb-NB142-70. Again, the azide analog, mcf292-08, maintained a high inhibitory activity both in vitro and in cells, with IC$_{50}$ values of 74.9 nM and 2.2 μM, respectively,

TABLE 2A

Chemical structures and PKD1 inhibitory activities of analogs with zone I modifications.

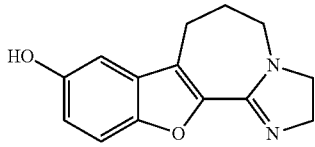

| | | Structure | | | % PKD1 activity | IC$_{50}$ | |
|---|---|---|---|---|---|---|---|
| | | | | | | radiometric | cellular |
| Entry | Compound | R$^1$ | R$^2$ | R$^4$ | at 1 μM | PKD1 (μM) | PKD1 (μM) |
| 1 | mcf292-03 | H | NH$_2$ | H | 74.4 ± 1.1 (n = 2) | 3.17 (n = 1) | n.d. |
| 2 | mcf292-08 | H | N$_3$ | H | n.d. | 0.08 ± 0.01 (n = 5) | 2.17 ± 0.22 (n = 3) |
| 3 | mcf292-05 | H | N=C=S | H | n.d. | 2.77 (n = 1) | n.d. |
| 4 | mcf292-09 | H | NHCOCH$_2$Cl | H | n.d. | 1.50 (n = 1) | n.d. |
| 5 | kb-NB165-31 | I | OH | H | 13.6 (n = 1) | 0.11 ± 0.02 (n = 3) | 8.6 ± 2.0 (n = 3) |
| 6 | kb-NB184-52 | Br | OH | H | 12.7 ± 0.2 (n = 2) | 0.048 (n = 1) | n.d. |
| 7 | kb-NB184-38 | H | H | OBn | 98.6 ± 4.1 (n = 2) | n.d. | n.d. |

TABLE 2A-continued

| | | | | | | |
|---|---|---|---|---|---|---|
| 8 | kb-NB184-40 | H | H | OH | 99 ± 11 (n = 2) n.d. | n.d. |
| 9 | kb-NB184-44 | H | H | OMe | 77.5 ± 3.6 (n = 2) n.d. | n.d. |

Electronic properties of the aryl ring also play a role in binding interactions. Thus, the methoxypyrimidine kmg-NB4-23 (Table 2B) exhibited an $IC_{50}$ of 124 nM, which represents only a slight decrease in activity compared to that of the parent compound, kb-NB165-09 (Table 2). This result suggests that the zone I binding pocket is tolerant to a decrease in electron density in the aryl region. Surprisingly, the hydroxy analog kmg-NB4-69A showed a significant loss in activity relative to the parental compound, kb-NB142-70 (Table 2). The loss of activity is attributed to the susceptibility of the C-4 position of the pyrimidine towards nucleophilic attack which causes the heterocycle to spontaneously degrade in protic solvents, and results in reduced inhibitory activity towards PKD1. More hydrolytically stable pyrimidine analogs containing a substituent at the $R^4$ position also exhibited a dramatic loss in activity, which is consistent with the general SAR results and provides additional support for a sterically limited zone I binding pocket. Compound kmg-NB4-23 suffers, however, from low aqueous solubility (<0.4 mg/mL), even in the presence of lipophilic solubilizing agents.

which the oxygen was replaced by an amino (—NH) group or sulfur atom were synthesized. SAR based on these studies indicated that the replacement of oxygen in CID755673 with an —NH group resulted in a pyrrole (β-carboline) derivative (kb-NB123-57, table 1A, entry 2) that has equal or slightly enhanced binding potency for PKD1, compared to CID755673. For example, the exemplified pyrrole derivative with an $IC_{50}$ of 130 nM is a better inhibitor of PKD1 protein than CID755673 (Table 3), however, kb-NB123-57 compound showed no significant cellular activity.

Moreover, variation of either the phenolic hydroxyl group or the lactam ring size in the β-carboline series did not provide any enhancement in activity (Table 3), and in cases where $R^2$ was replaced with O-benzyl (Table 3, entries 3 and 4) or N-acyl (Table 3, entries 7 and 8), all inhibitory activity was lost. These modifications, accordingly, confirm that the 7-membered azepinone represents an optimal size and that the binding pocket of the protein is sterically demanding at the aryl binding region.

TABLE 2B

Chemical structures and PKD1 inhibitory activities of analogs with zone I modifications to the pyrimidine scaffold.

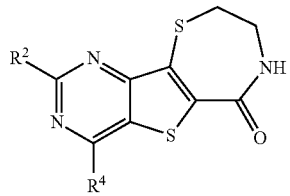

| | | Structure | | $IC_{50}$ | |
|---|---|---|---|---|---|
| Entry | Compound | $R^2$ | $R^4$ | radiometric PKD1 (µM) | cellular PKD1 (µM) |
| 1 | kmg-NB4-23 | OMe | H | 0.12 ± 0.03 (n = 4) | 6.8 ± 1.3 (n = 3) |
| 2 | kmg-NB4-69A | OH | H | 25.3 (n = 1) | n.d. |
| 3 | kmg-NB5-13C | OMe | OMe | >30.0 (n = 2) | n.d. |
| 4 | kmg-NB5-15A | OMe | OH | >30.0 (n = 2) | n.d. |

To evaluate the role of the zone II oxygen atom of CID755673 in inhibiting to PKD1, several derivatives in

TABLE 3

Chemical structure and PKD1 inhibitory activity of the β-carboline analogs.

| | | Structure | | IMAP-FP | $IC_{50}$ radiometric | cellular |
|---|---|---|---|---|---|---|
| Entry | Compound | $R^2$ | n | PKD1 (µM) | PKD1 (µM) | PKD1 (µM) |
| 1 | kb-NB123-59 | OH | 0 | 19.4 ± 1.4 (n = 3) | 1.57 ± 0.20 (n = 2) | n.d. |
| 2 | kb-NB123-57 | OH | 1 | 2.14 ± 0.12 (n = 3) | 0.13 ± 0.01 (n = 3) | >50 (n = 3) |

TABLE 3-continued

| | | | | | | |
|---|---|---|---|---|---|---|
| 3 | kb-NB123-52 | OBn | 0 | not inhibitory | n.d. | n.d. |
| 4 | kb-NB123-53 | OBn | 1 | not inhibitory | n.d. | n.d. |
| 5 | kb-NB142-08 | $NH_2$ | 0 | 74.4 ± 2.2 (n = 3) | 15.74 ± 0.19 (n = 2) | n.d. |
| 6 | kb-NB142-01 | $NH_2$ | 1 | 47.1 ± 2.5 (n = 3) | 9.68 ± 1.01 (n = 2) | n.d. |
| 7 | kb-NB123-93 | NHAc | 0 | not inhibitory | n.d. | n.d. |
| 8 | kb-NB123-94 | NHAc | 1 | not inhibitory | n.d. | n.d. |

It was unexpectedly found, however, that the corresponding zone II sulfur analogs of CID755673 were significantly more potent than CID755673. Thus, benzothienothiazepinone derivatives kb-NB142-70 and kb-NB165-09 represent a new class molecules that are candidate compounds for inhibiting PKD1 activity. As shown in Table 2, the in vitro $IC_{50}$ of two representative benzothienothiazepinone derivatives kb-NB142-70 and kb-NB165-09 are 28.3 nM and 82.5 nM respectively. The hydroxylbenzothienothiazepinone derivative inhibits PKD1 at a concentration approximately an order of magnitude lower than the $IC_{50}$ of CID755673.

Structural modifications to evaluate the effect of the size of the azepinone ring (zone III), indicate that the introduction or removal of a methylene group did not significantly alter the $IC_{50}$ value of ring expanded or ring contracted derivatives respectively, when compared to the parent compound CID755673. Zone III derivatives having a six- or eight-member ring show decreased binding affinity to the protein, however, compared to the corresponding seven member zone III derivatives. For example, the $IC_{50}$ values for the eight member hydroxyl (kb-NB165-92), and O-methyl ether (kb-NB184-02) derivatives are about 2.5-fold to 4-fold greater than the $IC_{50}$ values for the corresponding seven member hydroxyl (kb-NB142-70) and methyl (kb-NB165-09) compounds respectively, indicating that the zone III region of the protein accommodates seven member rings better than eight member ring systems.

Moreover, it was unexpectedly found during SAR exploration within zone III, that the insertion of a sulfur atom exo to the thiophene ring resulted in derivatives that were equally potent inhibitors of PKD1 as the corresponding methylene analogs. These results suggest that the benzothienothiazepinone ring represents a new molecular scaffold for a class of compound that are potent inhibitors of PKD1. Interestingly, etherification of the hydroxyl group of the eight member benzothienothiazocinone derivative kb-NB165-92, to give the corresponding O-methyl ether (kb-NB184-02), resulted in a decrease in binding affinity, similar to a decrease in binding observed for the seven member O-methyl benzothienothiazepinone derivative. Thus, hydrogen bonding interactions continue to play a role in binding for the exocyclic sulfur compounds.

Modifications of the oxidation state of the benzothiophene sulfur atom, the size of the thiazepinone ring, and the oxidation and substitution of the thiazepinone ring sulfur atom were also explored (Table 4). Sulfur oxidations in zones II and III provided analogs with reduced activity (Table 4, entries 1-3), while increasing the thiazepinone ring size by the addition of a methylene group had only minor effects on PKD1 inhibition for both the hydroxy and methoxy analogs (Table 4, entries 5 and 6). Additionally, the replacement of the thiazepinone ring sulfur atom with an oxygen resulted in a loss of inhibitory activity (Table 4, entries 7 and 8), suggesting high hydrophobicity and polarizability to be preferred in zone III. Furthermore, an acyclic precursor was tested (Table 4, entry 9), as an inhibitor of PKD's. The lack of inhibitory activity for this analog suggests that the zone III binding pocket may require the rigidity of a ring system for optimal binding interactions.

TABLE 4

Chemical structures and PKD1 inhibitory activities of zone II and III modifications

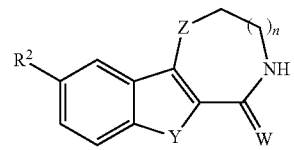

| | | Structure | | | | $IC_{50}$ | | |
|---|---|---|---|---|---|---|---|---|
| Entry | Compound | Y | Z | $R^2$ | n | % PKD1 activity at 1 µM | radiometric PKD1 (µM) | cellular PKD1 (µM) |
| 1 | kb-NB184-22 | S=O | S | OH | 1 | 66.5 ± 6.1 (n = 2) | n.d. | n.d. |
| 2 | kb-NB184-25 | S=O | S | OMe | 1 | 50.4 ± 2.3 (n = 2) | 1.08 (n = 1) | n.d. |
| 3 | kb-NB184-45 | S | S=O | OMe | 1 | 97 ± 16 (n = 2) | n.d. | n.d. |
| 4 | kb-NB165-89 | S | S | OBn | 2 | 84.3 (n = 1) | 21.7 (n = 1) | n.d. |
| 5 | kb-NB165-92 | S | S | OH | 2 | 16.7 (n = 1) | 0.11 ± 0.01 (n = 3) | 2.56 ± 0.66 (n = 2) |
| 6 | kb-NB184-02 | S | S | OMe | 2 | 29.5 (n = 1) | 0.19 ± 0.03 (n = 3) | 18.6 ± 2.0 (n = 3) |
| 7 | kb-NB184-36 | S | O | OBn | 2 | 83.3 ± 3.8 (n = 2) | n.d. | n.d. |
| 8 | kb-NB184-57 | S | O | OMe | 2 | 62.0 ± 3.5 (n = 2) | n.d. | n.d. |

TABLE 4-continued

Chemical structures and PKD1 inhibitory activities of zone II and III modifications

| Entry | Compound | Y | Z | R² | n | % PKD1 activity at 1 µM | IC₅₀ radiometric PKD1 (µM) | cellular PKD1 (µM) |
|---|---|---|---|---|---|---|---|---|
| 9 | kb-NB184-80 | | | | | 91.3 ± 1.5 (n = 2) | not inhibitory | n.d. |

The presence of an amide moiety in zone IV was found to be important for binding. Thus, replacement of the zone IV amide by other functional groups or the replacement of the zone IV amide by methylene groups destroyed binding and derivatives of CID755673 with zone IV modifications were found to be poor inhibitors of PKD1. For example, alkylation/acylation of the amide or bioisosteric replacements with an imidazole resulted in weak or no PKD1 inhibition (Table 2, entries 12-15 and 21). These observations suggest that the amide functionality may provide crucial H-bonding interactions in the azepinone binding pocket that are required for optimal inhibitor-enzyme interactions. See Table 2, above, and data illustrated in Table 5 below.

TABLE 5

Chemical structures and PKD1 inhibitory activities of zone IV modifications.

| Entry | Compound | W | R² | R⁵ | % PKD1 activity at 1 µM | IC₅₀ radiometric PKD1 (µM) |
|---|---|---|---|---|---|---|
| 1 | kb-NB165-16 | O | OMe | Me | | 4.57 ± 0.78 (n = 2) |
| 2 | kb-NB165-17 | O | OH | Me | | 0.45 ± 0.05 (n = 2) |
| 3 | kb-NB165-75 | O | OH | (CH₂)₂NH₂ | 55.6 (n = 1) | 0.757 (n = 1) |
| 4 | kb-NB165-81 | — | OBn | H | 78.3 (n = 1) | 39.6 (n = 1) |
| 5 | kb-NB165-83 | — | OH | H | 92.4 (n = 1) | 16.4 (n = 1) |

In one embodiment, the present invention provides compounds that conform to Formula I. For Formula I compounds $R_1$ is selected from the group consisting of hydrogen, straight or branched chain ($C_1$-$C_6$)alkyl, —OH, ($C_1$-$C_6$) alkoxy, —$N_3$, —NR'R", straight or branched ($C_1$-$C_6$)haloalkyl and straight or branched ($C_1$-$C_6$)haloalkoxy.

Substituent $R_2$ is hydrogen, or a straight or branched chain ($C_1$-$C_6$)alkyl. According to one embodiment, the inventive compounds belong to the benzothienoazepinone class. For this class of compounds, each X is independently a —CH— group. In another embodiment, each X is —N— and the inventive compounds belong to the azepinothiophenopyrimidinone class.

For Formula I compounds, Y is selected from the group consisting of —O—, —S— and —NR$^a$— and Z is selected from the group consisting of —C(R$^d$)$_2$—, —O—, —S— and —NR$^b$—. Substituents R', R" R$^a$, R$^b$ and R$^d$ for Formula I compounds are each independently selected from the group consisting of H, straight or branched ($C_1$-$C_6$)alkyl, straight or branched ($C_1$-$C_6$)haloalkyl, and —OH. Subscript "n" is an integer between 0 and 3 inclusive, for Formula I compounds.

Exemplary Formula I compounds include, without limitation, those shown below:

TABLE 6

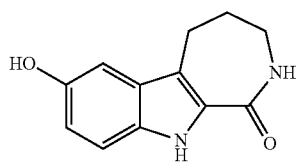 [SMILES: O=C1NCCCc2c1[nH]c1ccc(O)cc21]

TABLE 6-continued
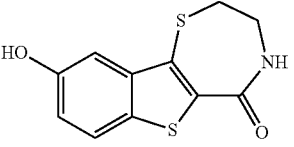 [SMILES: O=C1NCCSc2c1sc1ccc(O)cc21]
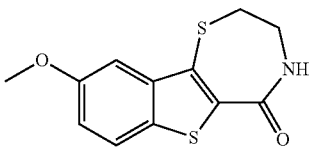 [SMILES: COc1ccc2sc3c(c2c1)SCCNC3=O]
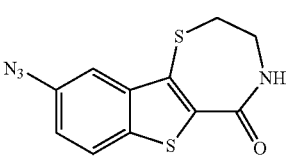 [SMILES: [N-]=[N+]=Nc1ccc2sc3c(c2c1)SCCNC3=O]
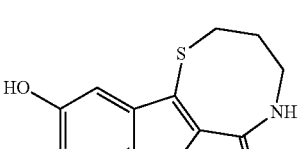
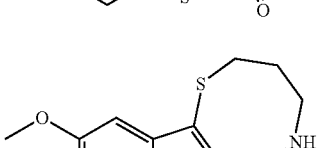
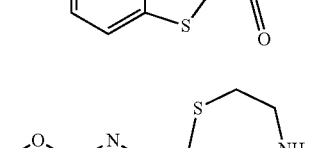
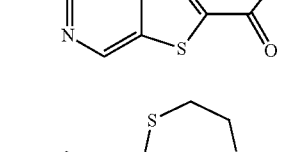
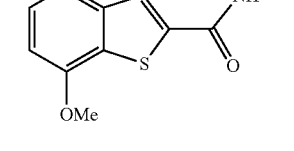
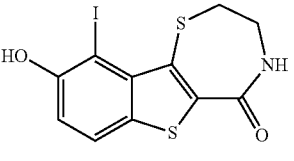 [SMILES: O=C1NCCSc2c1sc1ccc(O)c(I)c21]
TABLE 6-continued
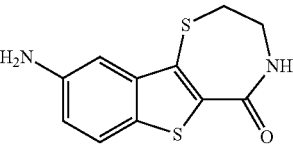 [SMILES: Nc1ccc2sc3c(c2c1)SCCNC3=O]
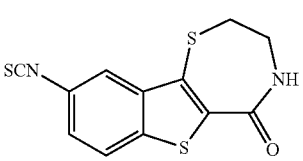
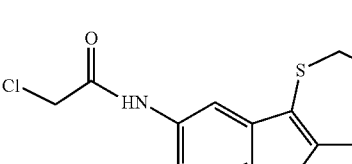
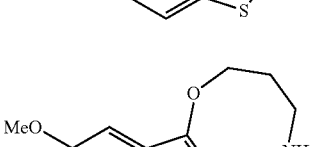
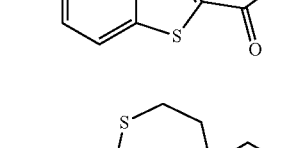
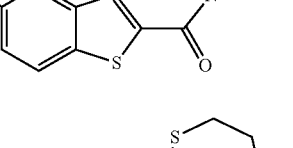
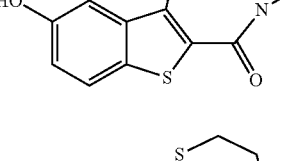
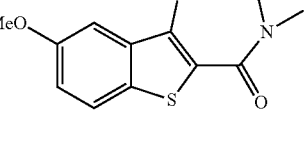
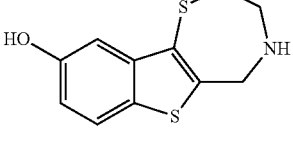
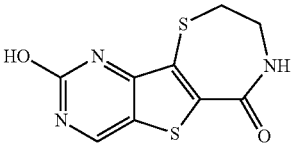

TABLE 6-continued

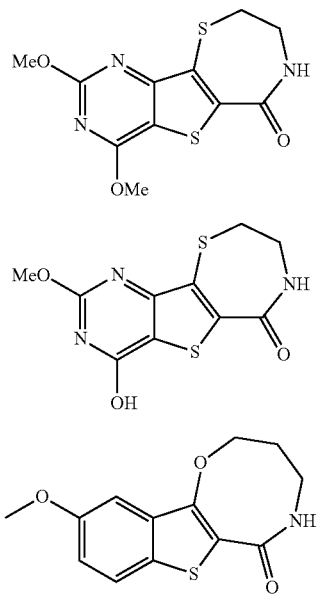

TABLE 7

| Analog | IC$_{50}$ (μM)(Ave ± SD) | | | |
|---|---|---|---|---|
|  | AKT | PLK1 | PLK2 | CAK(CDK7) |
| KMG-NB4-23 | >100 | >100 | >100 | >100 |
| MCF 292-08 | >50 | >50 | >50 | >50 |
| Kb-NB-142-70 | >100 | 17 ± 7.7 | 39 ± 3.4 | 12 ± 0.6 |
| Kb-NB 165-09 | >50 | >50 | >50 | 17.1 ± 13.6 |
| Kb-NB-123-57 | >100 | >100 | >100 | 39.2 ± 10.2 |
| Kb-NB-184-02 | >100 | >50 | >50 | 9 ± 4.1 |
| Kb-NB-165-92 | >50 | 13 ± 7.7 | 28 ± 3.1 | 11 ± 3.3 |

Selectivity and Potency

The described compounds were designed to be selective PKD inhibitors. The study of the SAR relationships described above was conducted to further improve potency and selectivity of the inventive compounds to PKD1. To establish the selectivity profile of the inventive compounds against other cellular kinases, the present inventors performed counter-screen selectivity assays using the following cellular kinases—AKT, CAK (CDK7), PLK1, PLK2, CaMK and the PKC family of enzymes as further explained below. Table 7 illustrates that Formula I compounds are poor inhibitors of the above mentioned cellular kinases, with IC$_{50}$ values in high micromolar range. In sharp contrast, the inventive compounds inhibit PKD in the low nanomolar range. As illustrated by the data in Table 2, IC$_{50}$ values for exemplary Formula I compounds for the PKD1 protein are in the range from about 20 nM to about 200 nM. For inhibition of cellular PKD1, the IC$_{50}$ values of exemplified inventive compounds was in the range from about 2.0 μM to about 20 μM. See Table 2. FIG. 1 further illustrates that the inventive compounds are poor inhibitors of PKCα, PKClβ, PKCδ and CaMKIIa kinases. The results from the counter-screen assays clearly indicate that Formula I compounds are selective and potent inhibitors of PKD.

Figure 2:
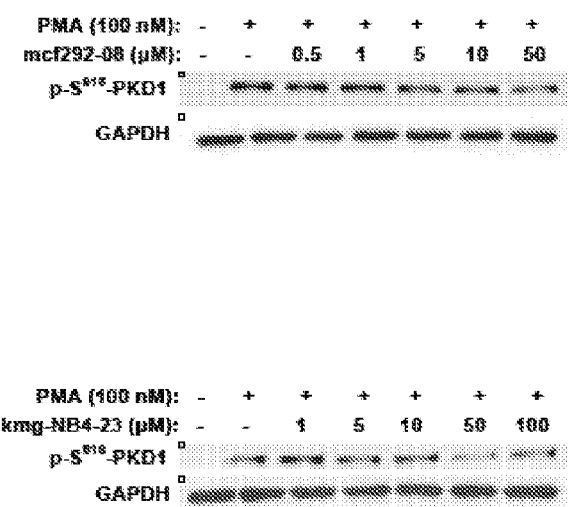
FIG. 2 represents Western Blot analysis of PMA-induced PKD1 $S^{916}$ autophosphorylation by two inventive compounds, kmg-NB4-23 and mcf292-08 in LNCap prostate cancer cells. Also illustrated is a graph for determining the $IC_{50}$ values for the inventive compounds based on densitometric analysis of the intensity of the visualized bands.
Figure 2:
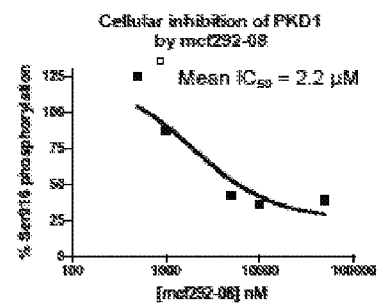
Figure 2:
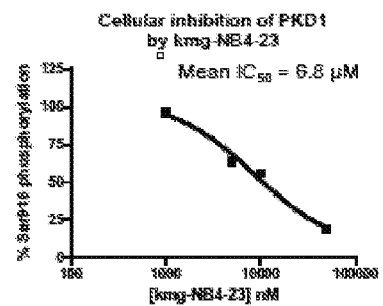
Figure 3:
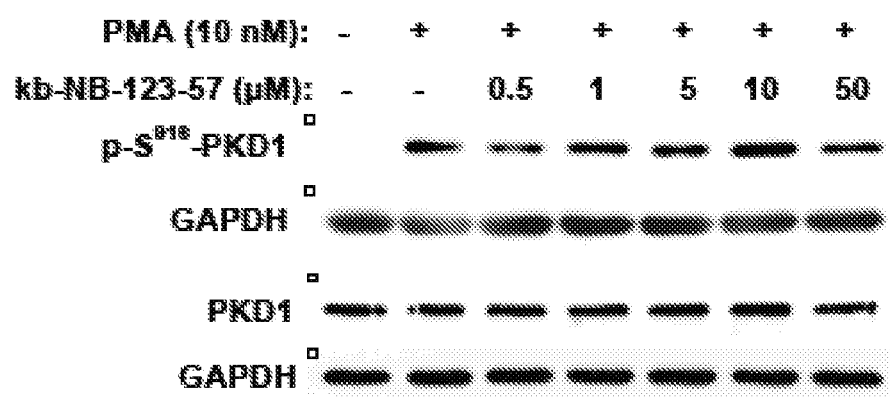
FIG. 3 represents Western Blot analysis of PMA-induced PKD1 $S^{916}$ autophosphorylation by a Formula I compound kmg-NB123-57 in LNCap prostate cancer cells.

To further elucidate the molecular mechanism for PKD inhibition by Formula I compounds, the present inventors tested the ability of certain Formula I compounds to block PMA-induced PKD1-S$^{916}$ autophosphorylation in LNCap prostate cancer cells. Western blot analysis using a primary antibody targeting p-S916-PKD1 was used to probe the cell lysates as further explained below. As illustrated in FIGS. 2 and 3, based on densitometric analysis of the visualized bands, the concentration of the inventive azidobenzothienothiazepinone compound (mcf292-08), required for 50% inhibition of PMA-induced PKD1 S916 autophosphorylation (IC$_{50}$) was 2.2 μM. The IC$_{50}$ value for PMA-induced PKD1 S916 autophosphorylation in LNCap prostate cancer cells using the inventive thiazepinothiophenopyrimidinone (kmgNB4-23) compound, was 6.8 μM. See FIG. 2. In contrast, kb-NB123-57 showed weaker inhibition of PMA-induced PKD1 autophosphorylation at S916. See FIG. 3.

Pharmaceutical Compositions and Dosages

The compounds of Formula I can be administered to a patient or subject in need of treatment either alone or in combination with other compounds having similar or different biological activities. For example, the compounds and compositions of the invention may be administered in a combination therapy, i.e., either simultaneously in single or separate dosage forms or in separate dosage forms within hours or days of each other. Examples of such combination therapies include administering the compositions of Formula I compounds with other agents used to treat cancer and cardiac problems.

In one embodiment, therefore, the invention provides a pharmaceutical composition comprising one or more compounds according to Formula I or a pharmaceutically acceptable salt, solvate, tautomer, or prodrug, in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

In one embodiment, the pharmaceutical composition comprises a compound selected from those illustrated in Table 6 or a pharmaceutically acceptable salt, solvate, tautomer, or prodrug thereof, and a pharmaceutically acceptable carrier.

The inventive compositions can be administered orally, parenterally, by inhalation or spray or rectally in dosage unit formulations. The term parenteral as used herein includes subcutaneous injections, intravenous, intramuscular, intrasternal injection or infusion techniques.

Inventive compositions suitable for oral use may be prepared according to any method known to the art for the manufacture of pharmaceutical compositions. For instance, liquid formulations of the inventive compounds contain one or more agents selected from the group consisting of sweetening agents, flavoring agents, coloring agents and preserving agents in order to provide pharmaceutically elegant and palatable preparations of the PKD1 inhibitor.

For tablet compositions, the active ingredient in admixture with non-toxic pharmaceutically acceptable excipients is used for the manufacture of tablets. Exemplary of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions the inventive compound is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as lecithin, or the condensation product of an alkylene oxide with fatty acids, for example polyoxyethylene stearate, or the product of ethylene oxide with long chain aliphatic alcohols, such as, heptadecaethyleneoxycetanol, or compounds such as polyoxyethylene sorbitol monooleate, or polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents include without limitation, naturally-occurring gums, for example gum acacia or gum tragacanth, other naturally-occurring compounds, for example, soy bean, lecithin, and esters or partial esters derived from fatty acids and hexitol, anhydrides, sorbitan monooleate and polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Synthesis of Compounds

Compounds that conform to Formula I were synthesized using synthetic methodologies described below and illustrated in the following schemes. The choice of an appropriate synthetic methodology is guided by the choice of Formula I compound desired and the nature of functional groups present in the intermediate and final product. Thus, selective protection/deprotection protocols may be necessary during synthesis depending on the specific functional groups desired. A description of such protecting groups and how to introduce and remove them is found in PROTECTIVE GROUPS IN ORGANIC SYNTHESIS ($3^{rd}$ ed.), T. W. Green and P. G. M. Wuts, John Wiley and Sons, New York (1999).

Exemplary general synthetic methodologies for making the fused ring scaffolds of Formula I compounds are provided below. More specific syntheses of illustrative Formula I compounds are also provided.

Scheme 1 below illustrates a general method for synthesizing the cyclic scaffold of Formula I compounds that have a pyrrole ring. According to this synthetic methodology, the tricyclic scaffold of kb-NB123-57 was prepared from phenylhydrazine 2 via a Fischer-like indole synthesis with the corresponding 7-membered α-ketolactam, obtained in situ by acid-catalyzed hydrolysis of the enamine 1 (Scheme 1). See Glushkov, R. G. et al., *Dokl. Akad. Nauk SSSR* 1969, 187, 327-329. Debenzylation by transfer hydrogenation led to the phenol kb-NB123-57. See Di Fabio, R. et al., *Bioorg. Med. Chem. Lett.* 2007, 17, 2254-2259.

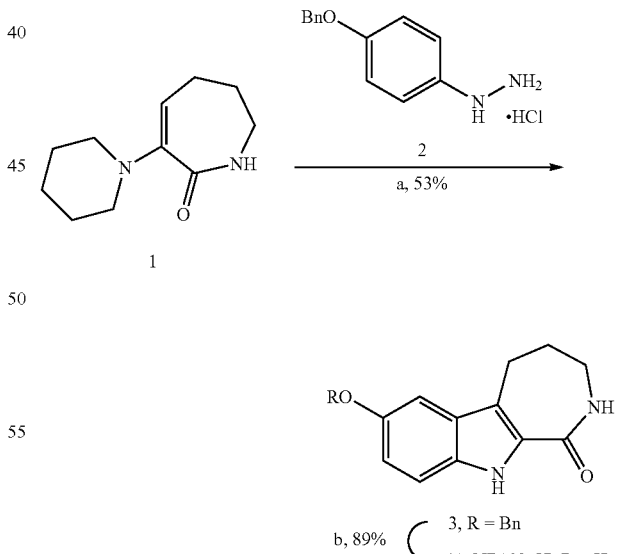

Scheme 1. Synthesis of the β-carboline analog kb-NB123-57

$^a$Reagents and conditions: (a) $H_2SO_4$, EtOH, reflux, 5 h. (b) Pd/C, $NH_4HCO_3$, MeOH, reflux, 2 h.

Formula I compounds that conform to the tetrahydro-1H-benzofuro[2,3-c]azepin-1-one scaffold were synthesized as illustrated in Scheme 2.

Scheme 2.

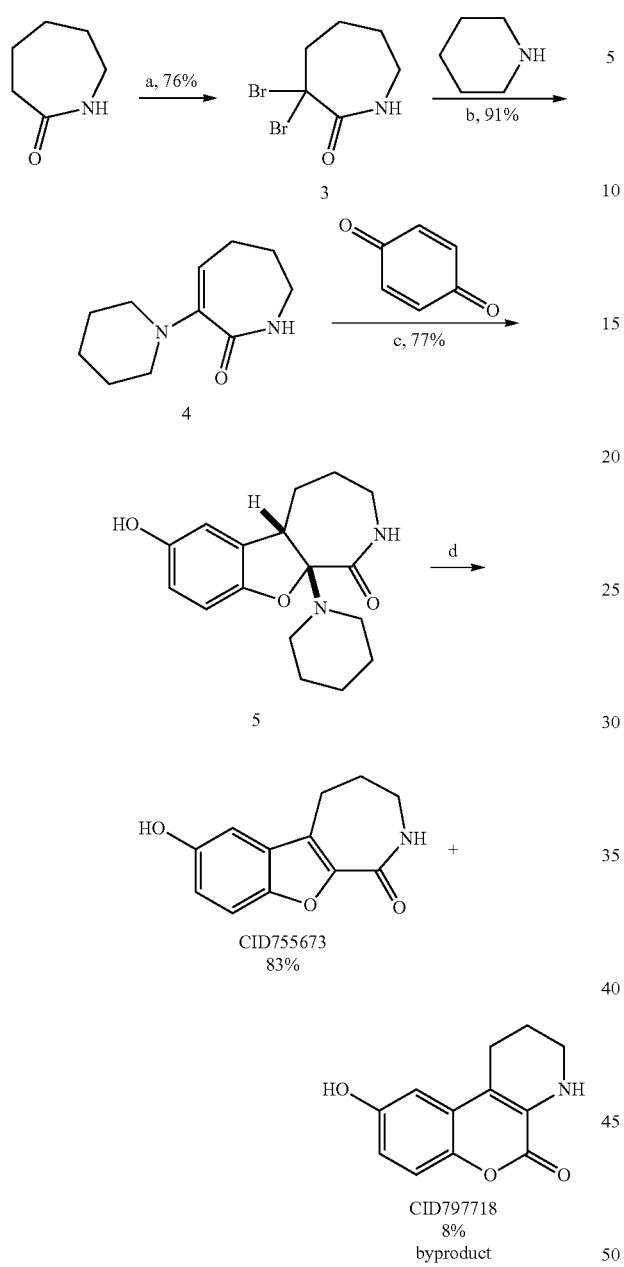

Scheme 3. Synthesis of the chlorinated analogs of CID755673

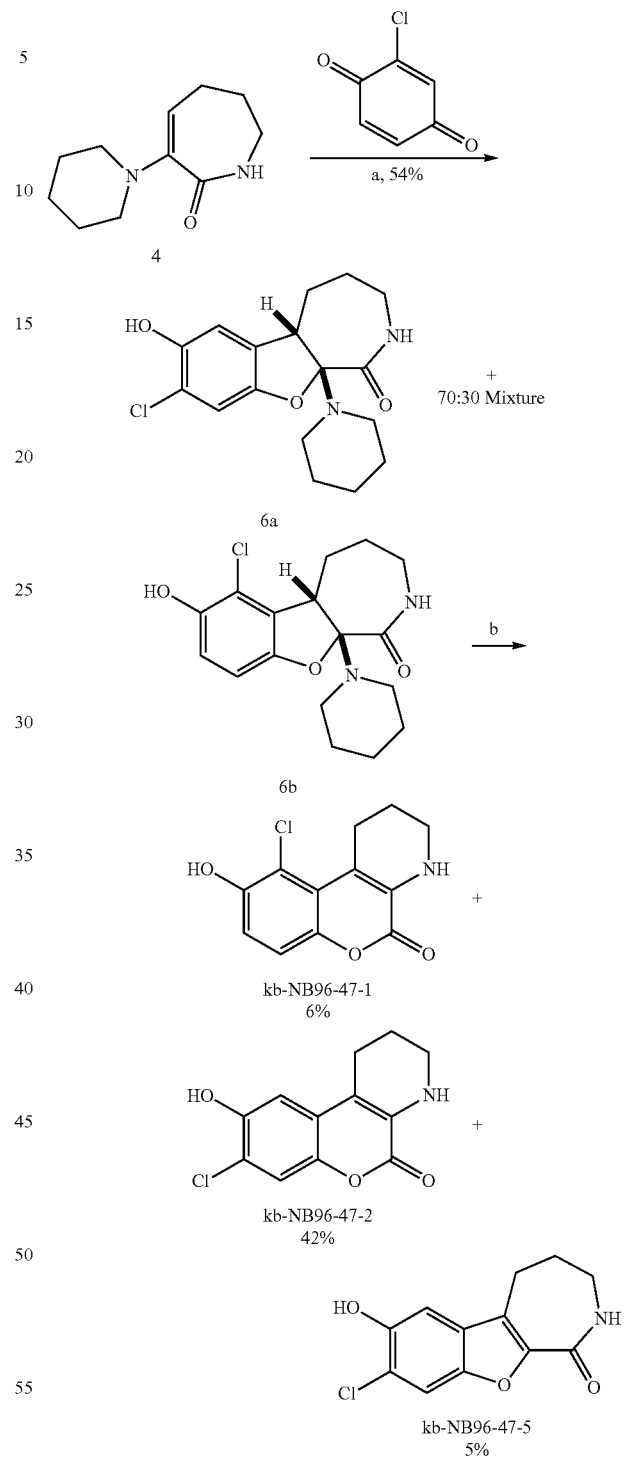

Commercially available δ-caprolactam, which was dibrominated at the α-position, and then treated with piperidine to afford the known α-oxolactam enamine 4. A Nenitzescu reaction between 4 and para-benzoquinone resulted in the formation of cyclic adduct 5, which was in turn subjected to heating in aqueous acid to provide the desired CID755673.

The synthesis of chlorinated analogs of CID755673 was challenging and the desired product was obtained in lower yields. Briefly, 4 was contacted with a cholorobenzophenone at room temperature, followed by heating in the presence of acetic acid and then refux of the resultant reaction mixture to give a mixture of the desired product and a halogenated chromenone pyridine compound.

[a] Reagents and conditions: (a) acetone, rt. (b) AcOH, 40° C.; then reflux.

The synthesis and functionalization of 6- and 8-membered ring analogs of CID755673 was carried out in a manner analogous to the methodology illustrated in Scheme 2. Briefly, for the 8-membered ring derivative 7b, acid-mediated piperidine elimination reaction proceeded with complete chemoselectivity toward the formation of the desired product kb-NB96-53. See Scheme 4. In contrast, for the 6-membered ring derivative 7a treatment with acetic acid provided the N-acetylated analog of the desired compound and the corresponding chromenopyrrole as the major products. Attempts to cleave the N-acetyl functionality to obtain the desired analog kb-NB123-23A were unsuccessful. However, subjecting 7a to mCPBA at elevated temperatures afforded the desired 6-membered azepinone ring analog, kb-123-23A, in good yield. See Scheme 4.

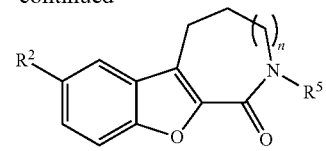

kb-NB123-32, n = 0, R² = OMe, R⁵ = H, 94%
kb-NB123-37, n = 0, R² = OMe, R⁵ = Me, 83%
kb-NB96-59, n = 2, R² = OMe, R⁵ = Me, 58%

<sup>a</sup>Reagents and conditions: (a) n = 0, DCE, 0.1 M aq. NaHCO₃, m-CPBA, reflux. (b) n = 2, AcOH, 40° C.; then reflux. (c) MeI, K₂CO₃. (d) MeI, KOt-Bu.

The 6- and 8-membered ring analogs (Scheme 4) were further modified by alkylating the phenolic hydroxyl group and the azepinone amide nitrogen atom. Treatment of kb-NB123-23A with MeI and K₂CO₃ provided the O-methylated compound, kb-NB123-32, while use of a stronger base such as KOt-Bu gave the desired dimethylated analog, kb-NB123-37, in good yield. The 8-membered dimethylated product kb-NB96-59 was obtained in a similar manner to kb-NB123-37, although only in modest yield.

The lack of potency of the 6- and 8-membered azepinone analogs, prompted efforts to further modify the aryl region of the parent compound CID755673. As stated above, functionalization of the phenolic —OH group was achieved by treatment with base in the presence of an electrophile (Table 8, entries 1-4). The presence of a stronger base, such as KOt-Bu or the presence of additional equivalents of the desired electrophile, gave the dimethylated compound kb-NB96-04 or the diacylated compound kb-NB123-45-1 (Table 8, entries 5 and 6). Modification of the aryl region also included addition of halogens (Table 8, entries 7-9). These derivatives could be obtained by the treatment of CID755673 with N-chlorosuccinimide in the case of the chlorinated analogs kb-NB77-88 and kb-NB96-43, or Selectfluor® in the case of the fluorinated analog kb-NB96-21.

Scheme 4. Synthesis of the 6- and 8-membered azepinone analogs

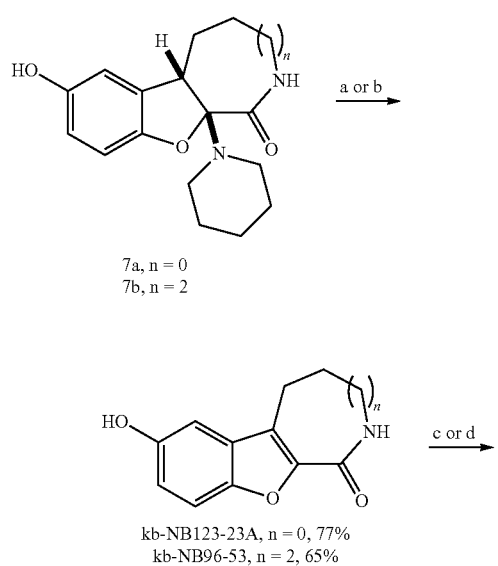

7a, n = 0
7b, n = 2 kb-NB123-23A, n = 0, 77%
kb-NB96-53, n = 2, 65%

TABLE 8

Functionalizations of CID755673.

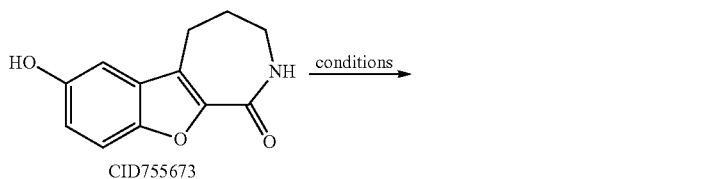

CID755673

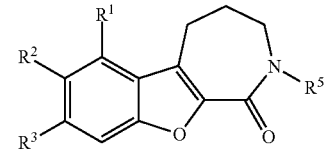

| Entry | Conditions | R¹ | R² | R³ | R⁵ | Yield, % | Product |
|---|---|---|---|---|---|---|---|
| 1 | MeI, K₂CO₃ | H | OMe | H | H | 74 | kb-NB77-56 |
| 2 | AllylBr, K₂CO₃ | H | OAllyl | H | H | 69 | kb-NB77-84 |
| 3 | TBSCl, iPr₂NEt | H | OTBS | H | H | 91 | kb-NB77-77 |
| 4 | AcCl (2 equiv), DMAP | H | OAc | H | H | 91 | kb-NB123-36 |
| 5 | MeI, KOt-Bu | H | OMe | H | Me | 34 | kb-NB96-04 |
| 6 | AcCl (3 equiv), DMAP | H | OAc | H | Ac | 33 | kb-NB123-45-1 |
| 7 | N-Chlorosuccinimide (1.05 equiv) | Cl | OH | H | H | 86 | kb-NB77-88 |

TABLE 8-continued

| 8 | Selectfluor® | F | OH | H | H | 29 | kb-NB96-21 |
| 9 | N-Chlorosuccinimide (2 equiv) | Cl | OH | Cl | H | 73 | kb-NB96-43 |

Further modifications were carried out in order to obtain a more complete SAR for the benzofuroazepinone series (Scheme 5). O-Allylation and N-methylation were performed on kb-NB77-88 and kb-NB77-77, respectively. Additionally, the microwave-mediated Claisen rearrangement of the O-allylated-benzoxoloazepinolone kb-NB77-84 provided the target compound kb-NB96-02 with the allyl functionality at the $R^1$ position. Protection of the phenol of kb-NB96-02 with a silyl group provided a derivative which could be subjected to Ru-catalyzed olefin isomerization conditions. Subsequent TBS deprotection provided the isomerized product kb-NB96-30 in modest yield over the three steps.

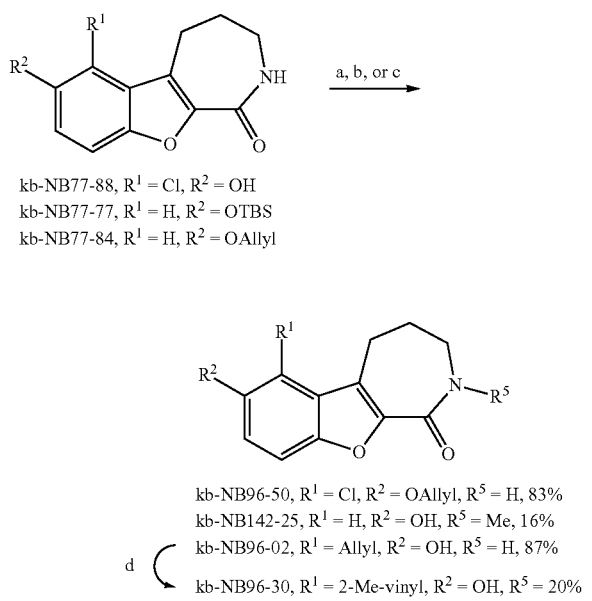

Scheme 5. Functionalizations of the benzofuran-based analogs kb-NB77-88, $R^1$ = Cl, $R^2$ = OH
kb-NB77-77, $R^1$ = H, $R^2$ = OTBS
kb-NB77-84, $R^1$ = H, $R^2$ = OAllyl kb-NB96-50, $R^1$ = Cl, $R^2$ = OAllyl, $R^5$ = H, 83%
kb-NB142-25, $R^1$ = H, $R^2$ = OH, $R^5$ = Me, 16%
kb-NB96-02, $R^1$ = Allyl, $R^2$ = OH, $R^5$ = H, 87%
kb-NB96-30, $R^1$ = 2-Me-vinyl, $R^2$ = OH, $R^5$ = 20%

$^a$ Reagents and conditions: (a) Allyl-Br, K$_2$CO$_3$, rt. (b) i.) NaH, MeI, DMF, 50° C.; ii.) TBAF, THF, rt. (c) MWI, 220° C. (d) i.) TBSCl, i-Pr$_2$Et, DMF, rt; ii.) RuClH(CO)(PPh$_3$), EtOH, reflux; iii.) TBAF, THF, rt.

In addition to alkylations and acetylations of the azepinone amide moiety, the effect of the isosteric replacement of the amide with an imidazole ring (Scheme 6), was evaluated. Thus, TIPS protection of the parental compound CID755673 followed by N-alkylation provided 8. Debenzylation by transfer hydrogenation, mesylation of the primary alcohol, and displacement of the resulting mesylate with sodium azide afforded the desired alkyl azide 9 in good yield over the three steps. After protection of the phenol, the alkyl azide was reduced to the amine and protected, prior to treatment with Lawesson's reagent to furnish thiolactam 10. Cyclo-dethionation of thiolactam 10 and subsequent TIPS deprotection delivered the desired imidazole containing analog, kb-NB165-15.

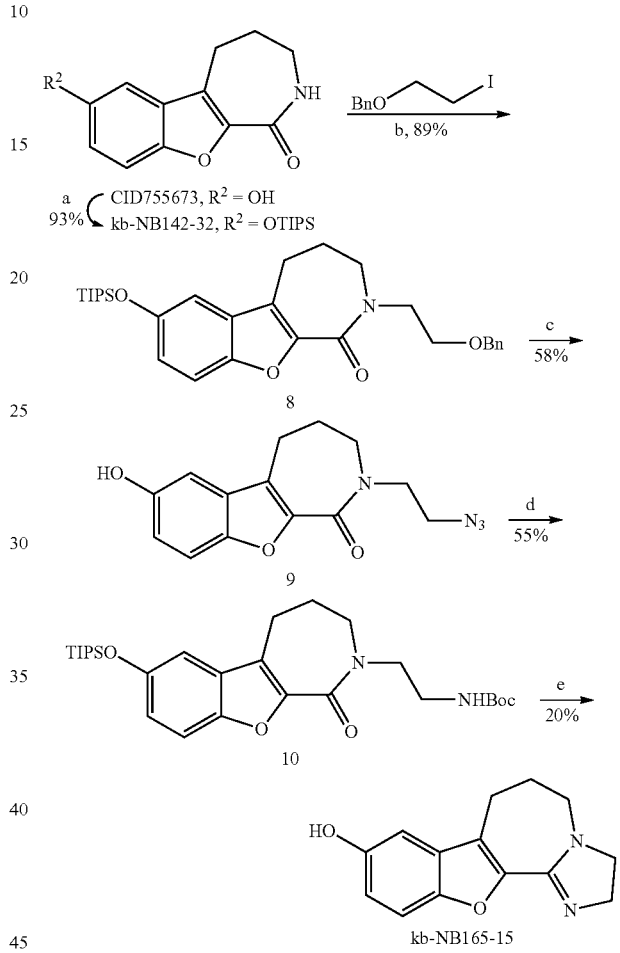

Scheme 6. Isosteric replacement of the amide moiety of CID755673 with an imidazole $^a$Reagents and conditions: (a) TIPSCl, Et$_3$N, DMAP, DMF, 50° C.. (b) n-BuLi, THF, -30° C. to reflux. (c) i) NH$_4$HCO$_2$, Pd/C, MeOH, reflux; ii) MsCl, Et$_3$N, DCM, 0° C. to rt; iii) NaN$_3$, DMF, 90° C.. (d) i) TIPSCl, Et$_3$N, DMAP, DMF, 50° C.; ii) H$_2$, Pd(OH)$_2$, Boc$_2$O, EtOAc, rt; iii) Lawesson's reagent, toluene, 100° C.. (e) i) MeI, rt; ii) TFA, DCM, 0° C.; then aq. NaOH, iii) CsF, MeCN, reflux.

The present inventors also explored the effect of functionalizing the azepinone methylene groups on binding (Scheme 7). Accordingly, functionalized azepinone Formula I compounds were synthesized by oxidation of the O-acetylated derivative kb-NB123-36 with PDC-TBHP in the presence of neutral alumina in order to install the desired ketone (11). The use of sonication proved to significantly improve both the yields and reproducibility of this oxidation. Subsequent acetyl deprotection in methanolic potassium carbonate solution provided kb-NB123-63. Access to further functionalized derivatives was achieved by acid-catalyzed condensation of kb-NB123-63 with O-benzylhydroxylamine or N-alkylated hydrazines (Scheme 7). The newly installed keto functionality was reduced using sodium borohydride to furnish the hydroxy derivative kb-NB123-89.

Scheme 7. Fuctionalization of the azepinone moiety of CID755673

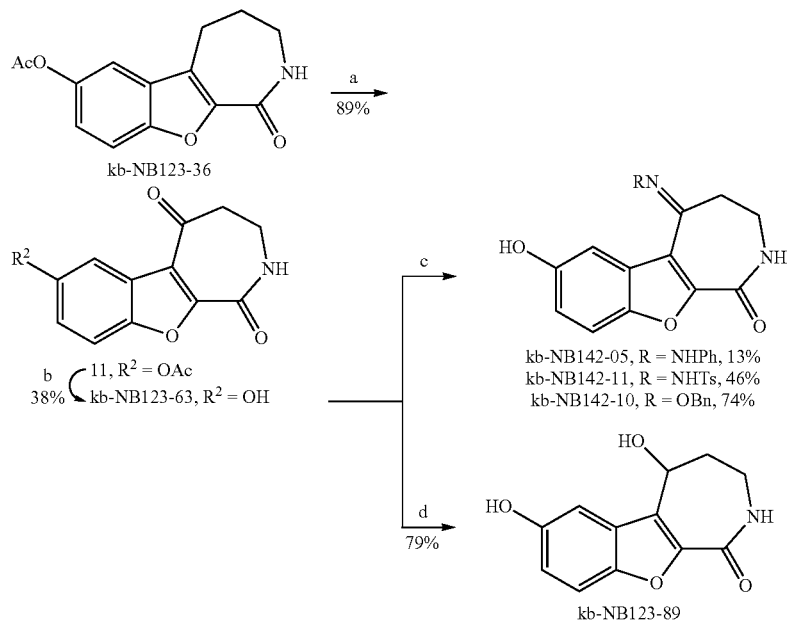

[a]Reagents and conditions: (a) PDC, TBHP, air, pyr/PhCl/MeCN, Al₂O₃, rt, sonication. (b) K₂CO₃, MeOH, rt. (c) RNH₂(•HCl), MeOH or EtOH, rt to reflux. (d) NaBH₄, THF/EtOH, rt.

The benzothienothiazepinones kb-NB142-70 and kb-NB165-09 were synthesized according to a literature protocol as as illustrated below in Scheme 8. Thus, protecting the hydroxyl group of commercially available 3-hydroxycinnamic acid as a benzyl ether followed by thionyl chloride-mediated Higa cyclization of acid 16 afforded a mixture of the benzo[b]thiophene acid chlorides, which were subsequently converted to methyl esters 17 and 18. The positional isomer 18 could be isolated as a byproduct from the thionyl chloride-mediated cyclization of 16. Treatment of the methyl esters with cysteamine hydrochloride in the presence of DBU resulted in formation of the desired benzothienothiazepinone core. Deprotection of the aryl benzyl ether with boron tribromide provided kb-NB142-70 in good yield. The corresponding methyl ether was obtained by reaction of the phenol with methyliodide give kb-NB165-09.

Scheme 8. Synthesis of benzothienothiazepinone analogs kb-NB142-70 and kb-NB165-09.

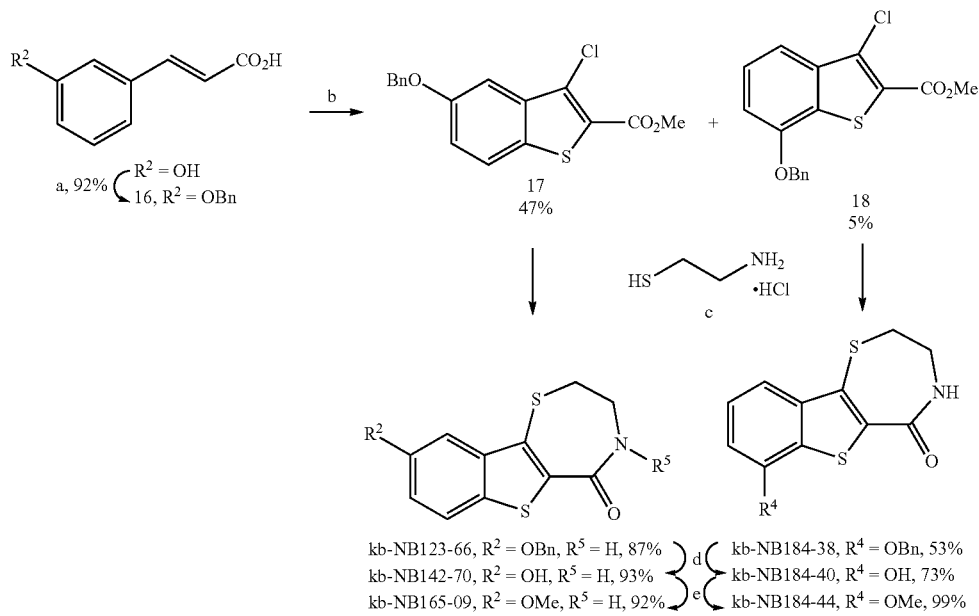

[a]Reagents and conditions: (a) BnBr, NaOH, EtOH, rt, 14 h. (b) (i) SOCl₂, pyr., DMF, PhCl, 120° C., 22 h; (ii) Et₃N, MeOH, reflux, 12 h. (c) DBU, DMF, rt, 1.5 h; then 70° C., 12 h. (d) BBr₃, DCM, -20 to 0° C., 2.5 h. (e) MeI, K₂CO₃, DMF, rt, 12 h.

Zone I modifications that involved halogenation of the aryl moiety were performed using standard iodination conditions to give analog kb-NB165-31 (Scheme 9 (a)). In contrast, the brominated analog kb-184-52 was synthesized from the corresponding sulfoxide kb-NB184-45 upon treatment with BBr$_3$ (Scheme 9 (b)).

to the modified Schotten-Baumann conditions reported by Nowick and co-workers (Table 9, entry 2). Lastly, treatment of mcf292-03 with chloroacetyl chloride in the presence of 2,6-lutidine provided the desired chloroacetyl analog mcf292-09 in modest yield over 2 steps (Table 9, entry 3).

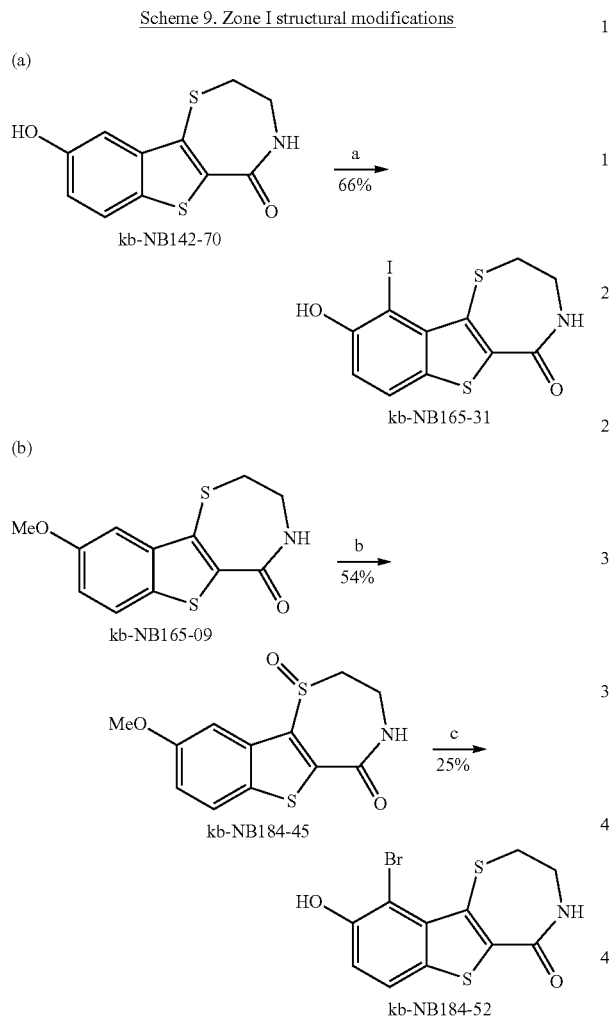

Scheme 9. Zone I structural modifications $^a$Reagents and conditions: (a) ICl, n-BuNH$_2$, THF, −40 to 0° C., (b) H$_2$O$_2$, TFA, DCM, 0° C. to rt. (c) BBr$_3$, DCM, −20° C. to rt.

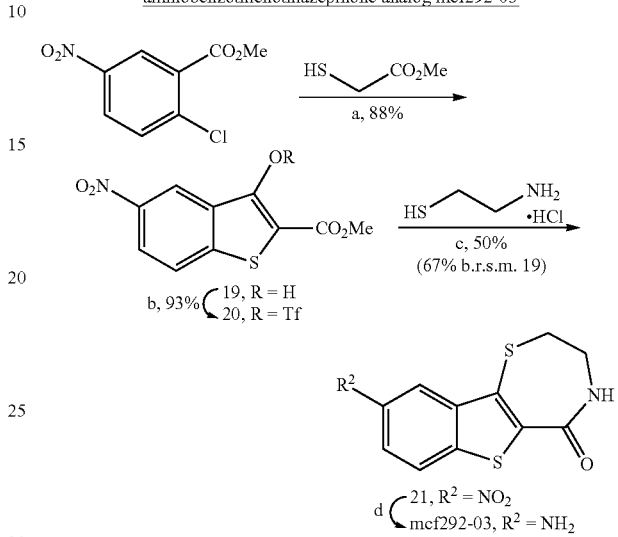

Scheme 10. Synthesis of the aminobenzothienothiazepinone analog mcf292-03

$^a$Reagents and conditions: (a) Et$_3$N, MeOH, 40-50° C.. (b) Tf$_2$O, Et$_3$N, DMAP, DCM, rt. (c) DBU, DMF, rt to 70° C.. (d) SnCl$_2$, EtOH, reflux.

Additional zone I modifications, which included replacement of the phenol group by nitrogen, required the development of an alternative route (Scheme 10 and Table 9). Nucleophilic aromatic substitution of methyl 2-chloro-5-nitrobenzoate by methyl thioglycolate anion followed by immediate Dieckman cyclization afforded the benzothiophene precursor 19. Cyclization of the corresponding triflate 20 with cysteamine hydrochloride provided the desired tricyclic core 21 in 50% yield (67% based on recovered starting material 19, Scheme 10). Subsequent reduction of the nitro group furnished aniline mcf292-03, which was further functionalized by treatment with t-butyl nitrite and TMS-azide using Moses' method to yield the aryl azide, mcf292-08 (Table 10, entry 1). The synthesis of the isothiocyanate mcf292-05 was realized by subjecting mcf292-03

TABLE 9

Zone I modifications based on mcf292-03.

| Entry | Conditions | Structure R$^2$ | Yield, % (from 21) | Product |
|---|---|---|---|---|
| 1 | tBuONO, TMSN$_3$, MeCN, rt | N$_3$ | 38% | mcf292-08 |
| 2 | CSCl$_2$, NaHCO$_3$, CHCl$_3$/H$_2$O, rt | NCS | 41% | mcf292-05 |
| 3 | ClCH$_2$COCl, 2,6-lutidine, DCM, rt | NHCOCH$_2$Cl | 46% | mcf292-09 |

Oxidation of the benzothiophene sulfur was carried out to evaluate the effect of a sulfoxide in Zone II of Formula I compounds. Thus, oxidation of ring sulfur atom of 17 (Scheme 11), with trifluoroperacetic acid to the 3-chlorobenzo[b]thiophene-1-oxide 22, followed by conversion to the corresponding benzyloxybenzothienothiazepinone-6-oxide 23, benzyl deprotection and methylation provided the desired sulfoxide analogs, kb-NB184-22 and kb-NB184-25, respectively (Scheme 11).

Scheme 11. Zone II structural modifications

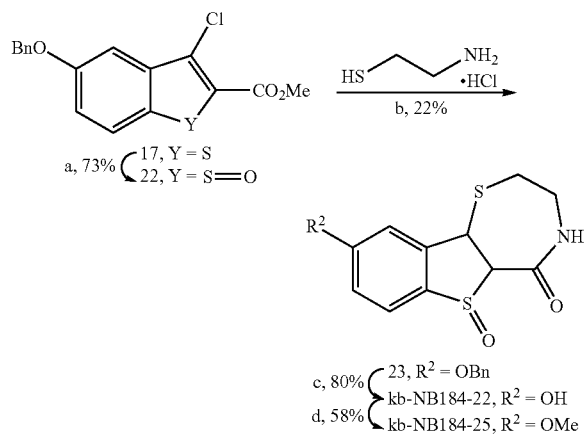

<sup>a</sup>Reagents and conditions: (a) H₂O₂, TFA, DCM, 0° C. to rt. (b) DBU, DMF, rt to 70° C.. (c) BBr₃, DCM, -20° C. to rt. (d) MeI, K₂CO₃, DMF, rt.

The eight member thiazocinone derivatives were synthesized using the protocol illustrated below in Scheme 12. The first step involved the synthesis of the aminopropanethiol hydrochloride 25 through a ring opening reaction of thiazinanethione 24, obtained in 2 steps from commercially available 3-amino-1-propanol (Scheme 12), using a published protocol. See Amir, N.; Motonishi, et al., *Eur. J. Inorg. Chem.* 2006, 1041-1049. The aminothiol 25 was isolated as an approximately 1:1.3 thiol/disulfide mixture and used directly in the cyclocondensation-deprotection sequence to yield the desired benzothienothiazocinones kb-NB165-92 and kb-NB184-02 respectively. Methylation of the phenolic hydroxyl group was carried out using methyliodide in the presence of a base, such as potassium carbonate.

Scheme 12. Synthesis of the benzothienothiazocinones kb-NB165-92 and kb-NB184-02

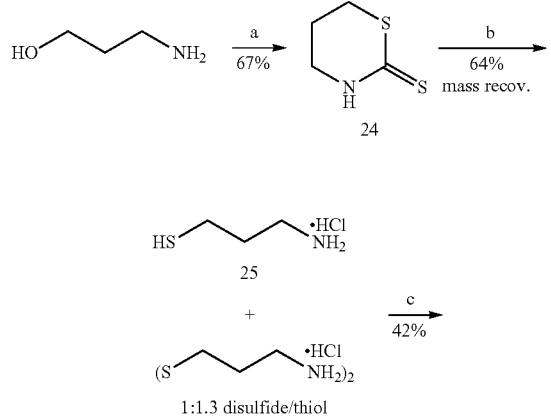

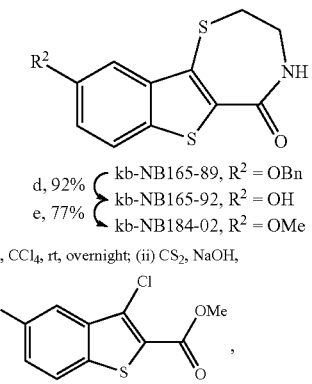

<sup>a</sup>Reagents and conditions: (a) (i) ClSO₃H, CCl₄, rt, overnight; (ii) CS₂, NaOH, EtOH/H₂O, 0° C. to reflux, 40 min. (b) conc. HCl, reflux, N₂, 14 d. (c) DBU, DMF, rt, 2 h; then 70° C., 18 h. (d) BBr₃, DCM, -20° C. to rt, 2 h. (e) MeI, K₂CO₃, DMF, rt, overnight.

The synthesis of the benzothiophene azide scaffold, however, required the development of an alternate synthetic route as illustrated below in Scheme 13. Thus, aromatic nucleophilic substitution of methyl 2-chloro-5-nitrobenzoate by the methyl thioglycolate anion followed immediately by Dieckman cyclization of the intermediate afforded the benzothiophene precursor a. See Dudova, K. et al., *Molecules* 2002, 7, 7-17 and Bertolasi, V. et al., *J. Mol. Struct.* 2003, 658, 33-42. Cyclization of the corresponding triflate b with cysteamine hydrochloride gave the desired tricyclic core c in 50% yield. Following reduction of the nitro group of the tricyclic scaffold, the corresponding aniline d was treated with tert-butyl nitrite and TMS-azide using the published protocol of Moses' et al., to give the desired aryl azide mcf292-08. See Moses, J. E. et al., *Org. Lett.* 2007, 9, 1809-1811.

Scheme 13. Synthesis of the azidobenzothienothiazepinone analog mcf292-08

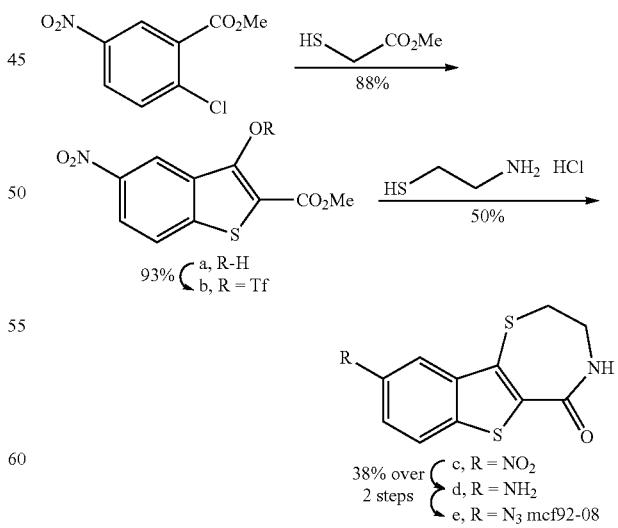

<sup>a</sup>Reagents and conditions: (a) Et₃N, MeOH, 40-50° C., 4 h. (b) Tf₂O, Et₃N, DMAP, DCM, rt, 2 h. (c) DBU, DMF, rt, 1.5 h; then 70° C., 13 h. (d) SnCl₂, EtOH, reflux, 5 h. (e) t-BuONO, TMSN₃, MeCN, rt, 1.5 h.

The azido analog, moreover, provides a valuable tool for photoaffinity studies aimed at elucidating key structural information about PKD's binding site, for example, information about which groups within PKD1's binding site interact with Formula I compounds and the nature of their interactions.

In an effort to further assess the SAR for zone III modifications, the present inventors investigated the synthesis of benzothiophene analogs linked to a three-carbon chain by an ether or amine function, instead of the thioether present in the lead compound. Key to accomplishing the synthesis of the ether analog kb-NB184-36 was the use of the activated chloride 22, which was obtained via oxidation of the benzothiophene sulfur to the corresponding sulfoxide according to Scheme 12. A DMAP-catalyzed nucleophilic displacement of the chlorine atom with alcohol 26 afforded the cyclization precursor 27, which upon N-Boc deprotection and subsequent tandem cyclization-deoxygenation led to the benzyloxybenzothienooxazocinone analog kb-NB184-36 (Scheme 14 (a)). The methoxy analog kb-NB184-57 was synthesized in a similar manner (Scheme 14 (b)).

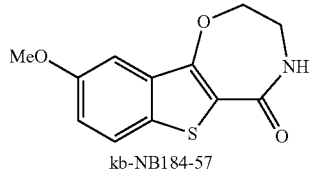

kb-NB184-57

[a]Reagents and conditions: (a) i) DMAP, DCE, rt; ii) 26, i-Pr$_2$NEt, DCE, 60° C..
(b) i) 4N HCl/dioxane, rt; ii) NaOMe, MeOH, reflux. (c) i) SOCl$_2$, pyr, DMF, PhCl, 120° C.; ii) Et$_3$N, MeOH, reflux, (d) H$_2$O$_2$, TFA, DCM, 0° C. to rt.
(e) i) 26, DMAP, i-Pr$_2$NEt, DCM, reflux; ii) 4M HCl/dioxane, rt; iii) NaOMe, MeOH, reflux.

In an analogous manner, the synthesis of diazepinone analog 31 was attempted; however, precursor 30 failed to undergo cyclization under both base- and Cu-mediated conditions (Scheme 15 (a). Therefore, the synthetic protocol was modified to include a nucleophilic displacement at the activated chlorine atom in 29 with aminopropanol, followed by a TMSI-mediated deoxygenation of 32 to provide kb-NB184-80 (Scheme 15 (b)).

Scheme 14. Zone III structural modifications

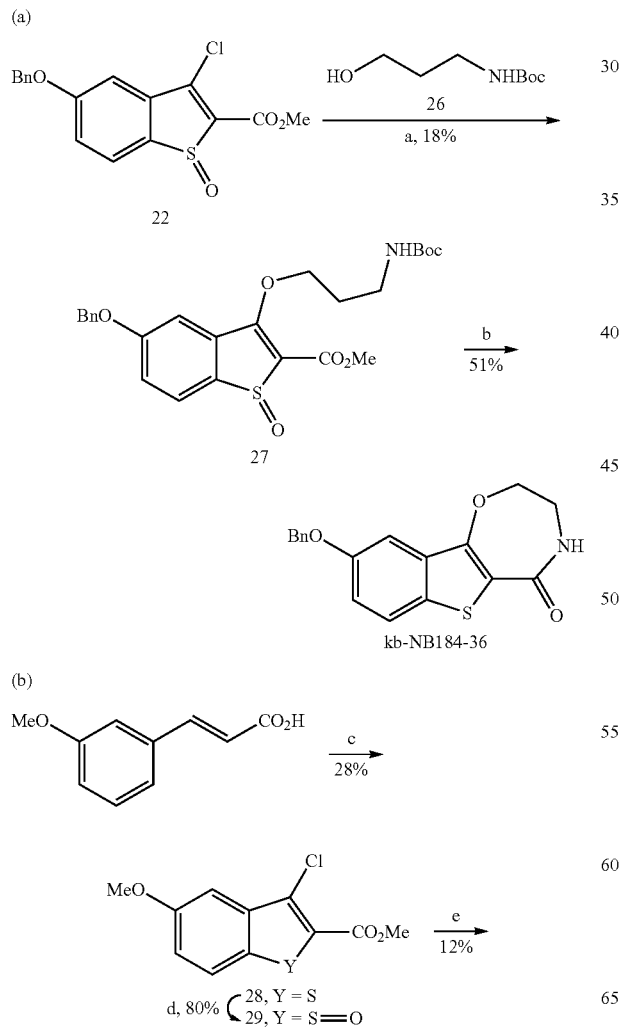

Scheme 15. Zone III structural modifications

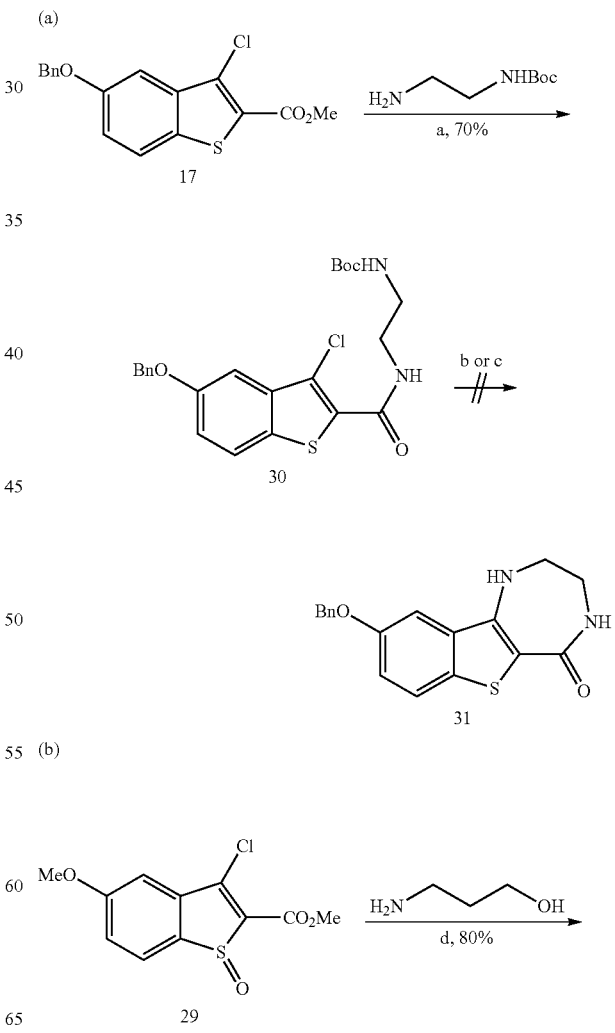

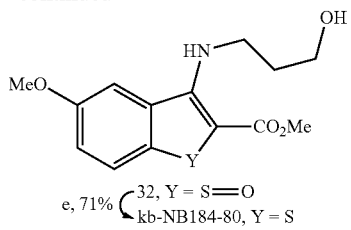

e, 71% ⌈ 32, Y = S═O
       ⌊ kb-NB184-80, Y = S

<sup>a</sup>Reagents and conditions: (a) TBD, 75° C.. (b) NaH. (c) i) acid; ii) Cu₂O, collidine. (d) NaH, THF/DMF, 0° C. to rt. (e) TMSCl, NaI, MeCN/THF, rt.

Finally, the inventors explored structural modifications of zone IV by alkylation of the amide nitrogen and reduction of the amide (Schemes 16 and 17, respectively). The N-methylated analog kb-NB165-17 was prepared from the benzyloxybenzothiazepinone kb-NB123-66 (Scheme 8) through an alkylation-deprotection sequence, while the dialkylated kb-NB165-16 was obtained in one step by treatment with NaH and MeI. The synthesis of kb-NB165-75 was accomplished via the N-alkylation of silyl protected kb-NB142-70 with the corresponding alkyliodide, followed by functional group interconversions and a final deprotection to furnish the desired analog kb-NB165-75. The amide reduction of thiolactam 36 proceeded poorly upon treatment with Raney-Nickel in THF due to a competitive cleavage of the other C—S bonds present in this system (Scheme 17). Nonetheless, we were able to isolate kb-NB165-81 in low yields and debenzylate it to afford the desired phenol kb-NB165-83 (Scheme 17).

Scheme 16. Zone IV structural modifications

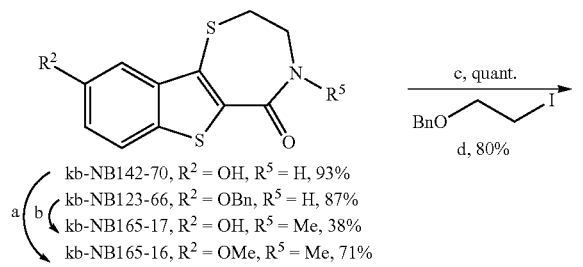

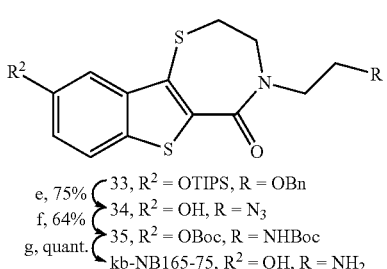

<sup>a</sup>Reagents and conditions: (a) NaH, MeI, DMF, 50° C.. (b) i) NaH, MeI, DMF, rt; ii) BBr₃, DCM, -20° C. to rt. (c) TIPSCl, Et₃N, DMAP, DMF, 50° C.. (d) n-BuLi, THF, -20° C. to reflux. (e) i) BBr₃, DCM, -20° C. to rt; ii) MsCl, Et₃N, DCM; iii) NaN₃, DMF, 90° C.. (f) i) PPh₃, THF, rt; then H₂O; ii) Boc₂O, Et₃N, DCM, rt. (g) 4N HCl/dioxane, MeOH, rt.

Scheme 17. Zone IV structural modifications (continued)

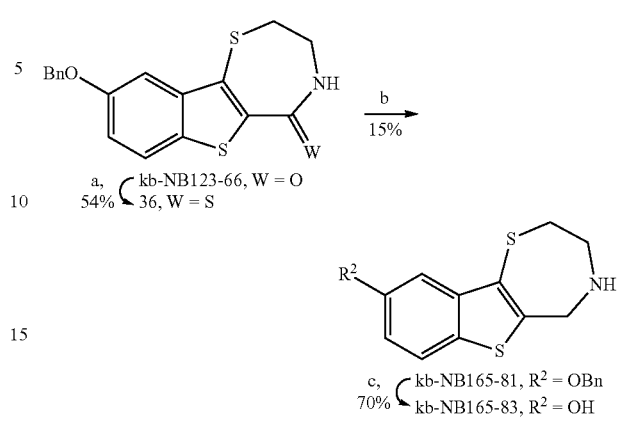

<sup>a</sup>Reagents and conditions: (a) Belleau's reagent, toluene, 100° C.. (b) H₂, Ra—Ni, THF, rt. (c) BBr₃, DCM, -20° C. to rt.

As stated above, SAR studies carried out by the present inventors have established that the benzothienothiazepinones more potent inhibitors of the protein kinase D-1 enzyme, compared to benzofuroazepinones. As shown by the $IC_{50}$ data in Table 2, benzothienothiazepinone kb-NB142-70 was the most potent analog with an in vitro $IC_{50}$ of 28 nM for PKD1. This compound is nearly 7-fold more potent than CID755673. An in vivo cell-based assay confirmed the potency of kb-NB142-70 which showed a cellular $IC_{50}$ of 2.2 µM. The cellular $IC_{50}$ of kb-NB142-70 is 5-fold lower than the cellular $IC_{50}$ for CID755673 (11.8 µM).

The benzothienothiazepinones suffer, however, from a short plasma half-life as shown by in vivo studies. See Wipf, P. et al., Manuscript in preparation. Without being bound by any theory, the plasma stability studies have shown that the short plasma half-life may be due to the active phase I and phase II metabolism of the phenolic moiety of benzothienothiazepinones.

To improve the plasma half-life of thiazepinone class of compounds, further studies were carried out to determine if groups other than phenol were more stable to metabolic degradation without any loss in binding potency to PKD1. SAR studies in this context have shown that the presence of an electron deficient moiety in place of the phenol increase metabolic stability and plasma half-life. In particular, replacing the phenol with an electron-deficient pyrimidine ring resulted in a new class of electron deficient thiazepinones as inhibitors of PKD1.

The synthetic route to arrive at this new thiazepinothiophenopyrimidinone scaffold is summarized in Scheme 18. Starting with commercially available methyl 3-aminothiophene-2-carboxylate, formation of the pyrimidine moiety using potassium cyanate and chlorination with POCl₃ provided dichloride 38. Regioselective palladium-catalyzed hydrogenolysis of 38 in the presence of Na₂CO₃ occurred exclusively at the C-4 position [75], and substitution of the remaining C-2 chloride with methoxide provided 40 in 79% yield over the two steps. Electrophilic bromination of 40 using bromine in acetic acid gave the desired C-7 bromo compound 41. Functionalization at C-6 was accomplished via selective metalation and trapping with Mander's reagent to provide the required cyclization precursor 42. Formation of the thiazepinone moiety was achieved by a one-pot nucleophilic displacement-condensation of 42 with cysteamine hydrochloride to provide the desired methoxypyrimidine kmg-NB4-23 in good yield. When kmg-NB4-23 was subjected to 4 M HCl in 1,4-dioxane, the desired hydroxypyrimidine kmg-NB4-69A was formed as the hydrochloride salt (Scheme 18).

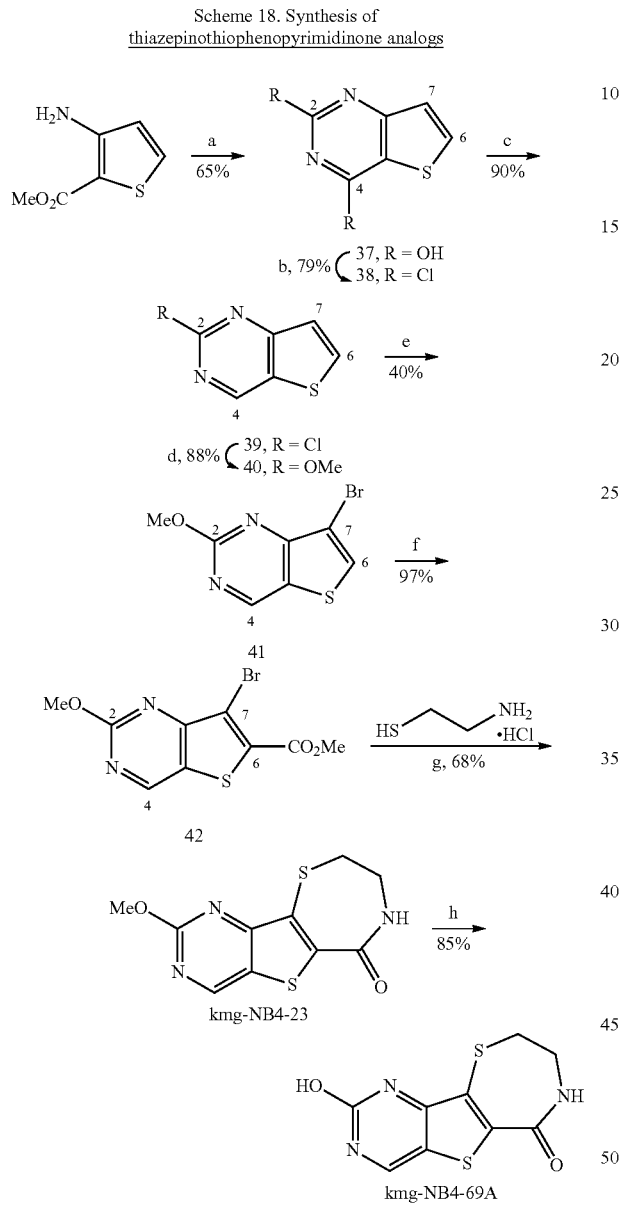

Scheme 18. Synthesis of thiazepinothiophenopyrimidinone analogs

<sup>a</sup>Reagenst and conditions: (a) i) KOCN, AcOH, H₂O, rt, 20 h; ii) 2M NaOH, rt. (b) POCl₃, MeCN, reflux. (c) H₂, Pd/C, EtOH, Na₂CO₃, rt. (d) NaOMe, MeOH, reflux. (e) AcOH, Br₂, 70° C.. (f) i) TMPMgCl•LiCl, -50° C.; ii) MeCO₂CN. (g) DBU, DMF, rt; then 70° C. (h) 4M HCl/dioxane, 80° C.

Pyrimidine kmg-NB4-23 is a potent nanomolar inhibitor of PKD, thus confirming the validity of other above design. In contrast, kmg-NB4-69A had only weak inhibitory effect against PKD. This lack of activity is attributed to the instability of the compound towards nucleophilic addition of H₂O at the C-4 position. Efforts to stabilize the C-4 position led to the design of compounds kmg-NB5-13 and kmg-NB5-15 (Scheme 19). These analogs were successfully synthesized in a similar manner to kmg-NB4-23 and kmg-NB4-69A (Scheme 18).

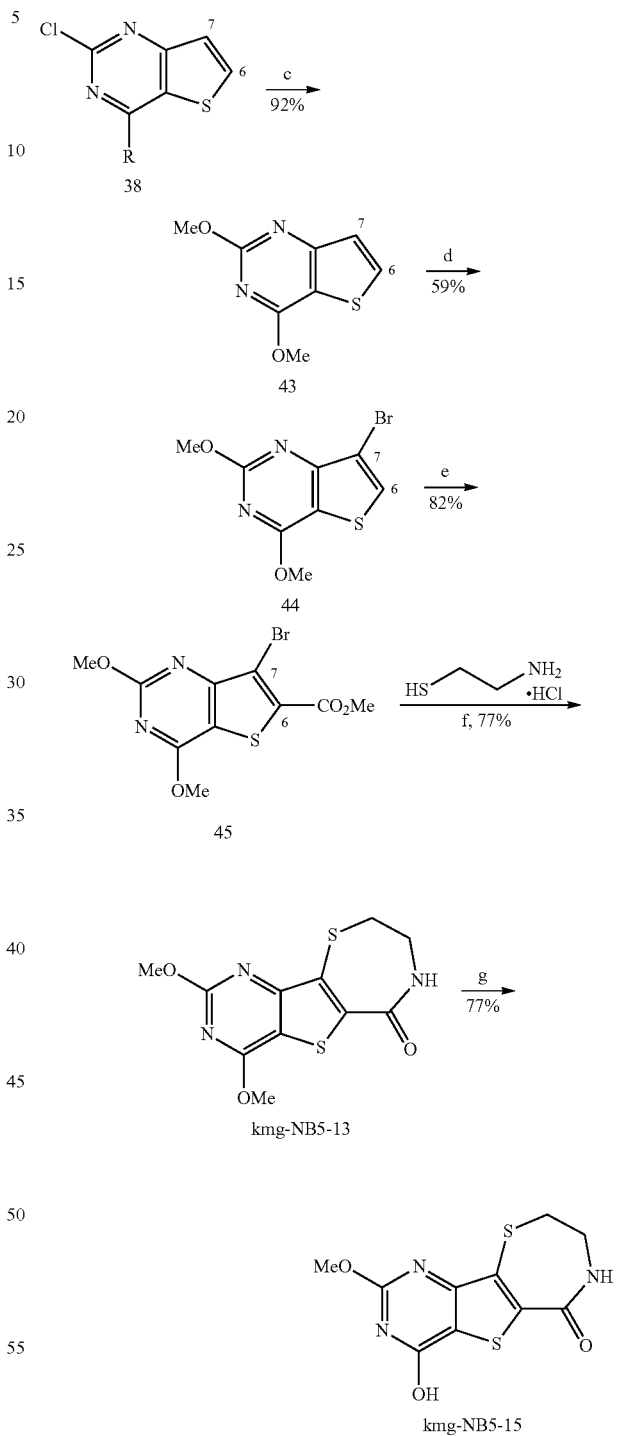

Scheme 19. Synthesis of thiazepinothiophenopyrimidinone analogs

<sup>a</sup>Reagenst and conditions: (a) i) KOCN, AcOH, H₂O, rt, 20 h; ii) 2M NaOH, rt. 2 h. (b) POCl₃, MeCN, reflux, 2 d. (c) NaOMe, MeOH, reflux, 48 h. (d) AcOH, Br₂, rt, 32 h. (e) i) TMPMgCl•LiCl, -50° C., 2 h; ii) MeCO₂CN. (f) DBU, DMF, rt, 3 h. (g) KOSiMe₃, THF, 80° C., 22 h.

The present invention also provides a synthetic route for making thienopyridine Formula I analogs as illustrated in Scheme 20.

Scheme 20. Synthesis of thienopyridine analogs.[a]

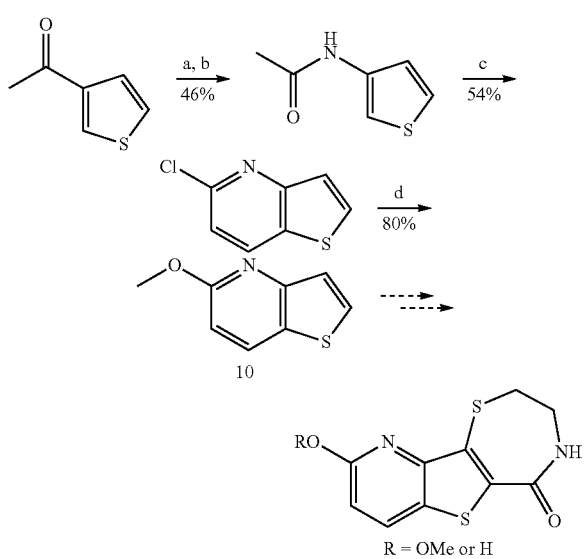

[a]Reagents and conditions: (a) NH$_2$OH•HCl, NaHCO$_3$, EtOH, H$_2$O, 60° C., 12 h. (b) PPA, 100° C., 1 h. (c) (i) POCl$_3$, DMF, DCE, reflux, 21 h. (ii) aq. NaOAc, reflux, 30 min. (d) NaOMe, MeOH, 80° C., 14 h.

Ex vivo protein inhibition studies show that the pyrimidine derivative kmg-NB4-23 exhibited an IC$_{50}$ of 124 nM, suggesting the PKD1 inhibitory activity of the pyrimidine derivative is only slightly lower than the parent compound kb-NB165-09. The results from inhibition studies confirms the present inventors hypothesis that decreased π-electron density is well tolerated in the zone I aryl region and has prompted the development of a new class of PKD1 inhibitors based on the thiazepinothiophenopyrimidinone scaffold.

Examples

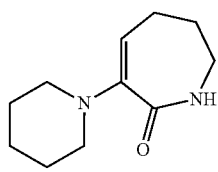

3-Piperidin-1-yl-1,5,6,7-tetrahydroazepin-2-one (1)

To a solution of ε-caprolactam (15.2 g, 133 mmol) in CHCl$_3$ (400 mL) cooled to 0-5° C. was added PCl$_5$ (55.2 g, 265 mmol) over the course of 30 min, followed by addition of anhydrous ZnI$_2$ (1.53 g, 4.79 mmol) under N$_2$. The reaction mixture was slowly allowed to reach room temperature as Br$_2$ (42.4 g, 265 mmol) was added dropwise over the course of 30 min. The mixture was stirred at room temperature for 6 h and then poured into ice-water (300 mL). The aqueous layer was extracted with CHCl$_3$ (3×100 mL) and the combined organic layers were washed with 0.50 M aq. NaHSO$_3$ (3×200 mL) and brine (1×400 mL), dried (MgSO$_4$) and concentrated to yield a yellow solid residue. The solid was suspended in water, filtered, and washed with water and Et$_2$O to give 3,3-dibromoazepan-2-one (27.5 g, 76%) as a white solid: $^1$H NMR (CDCl$_3$, 600 MHz) δ 6.91 (bs, 1H), 3.39 (app dd, 2H, J=10.3, 5.8 Hz), 2.77-2.72 (m, 2H), 2.02-1.94 (m, 2H), 1.73-1.67 (m, 2H); $^{13}$C NMR (CDCl$_3$, 150 MHz) δ 168.7, 69.7, 46.2, 42.8, 28.6, 28.5; HRMS (ESI) m/z calcd for C$_6$H$_9$Br$_2$NONa (M+Na) 291.8949, found 291.8973.

A solution of 3,3-dibromoazepan-2-one (15.7 g, 57.9 mmol) in piperidine (140 mL) was heated at reflux for 4.5 h under N$_2$. The solution was then allowed to reach room temperature and washed with 0.50 M aq. NaHSO$_3$ (200 mL). The aqueous phase was extracted with CHCl$_3$ (3×100 mL) and the combined organic layers were washed with brine (1×300 mL), dried (MgSO$_4$) and concentrated to afford a brown, oily solid, that crystallized upon standing. The resulting solid was suspended in water, filtered, and washed with water and Et$_2$O to give 1 (10.3 g, 91%) as a white solid: IR (ATR, neat) 3193, 2950, 2935, 2923, 2855, 1655, 1605 cm$^{-1}$; $^1$H NMR (CDCl$_3$, 600 MHz) δ 6.51 (bs, 1H), 5.06 (t, 1H, J=7.6 Hz), 3.22 (q, 2H, J=6.5 Hz), 2.78 (app t, 4H, J=5.3 Hz), 2.15 (q, 2H, J=7.2 Hz), 1.76 (app quint, 2H, J=6.8 Hz), 1.69-1.62 (m, 4H), 1.54-1.48 (m, 2H); $^{13}$C NMR (CDCl$_3$, 150 MHz) δ 171.5, 147.6, 105.4, 50.1, 39.5, 30.2, 25.5, 24.5, 21.5; HRMS (EI) m/z calcd for C$_{11}$H$_{18}$N$_2$O 194.1419, found 194.1422.

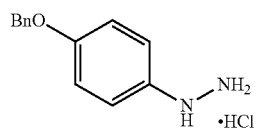

(4-(Benzyloxy)phenyl)hydrazine hydrochloride (2)

Note: The reaction mixture and all added solutions were maintained at 0° C. during this procedure. 4-Benzyloxyaniline hydrochloride (3.00 g, 12.5 mmol) was added to conc. aq. HCl (25 mL) and stirred for 10 min at 0° C., followed by dropwise addition of a solution of NaNO$_2$ (852 mg, 12.3 mmol) in water (6 mL) over the course of 15 min. The mixture was stirred for an additional 15 min-period and then a solution of SnCl$_2$ (6.40 g, 33.1 mmol) in conc. aq. HCl (7.5 mL) was added dropwise. The reaction mixture was stirred for 1 h and filtered to yield an off-white precipitate, which was washed with water and triturated with Et$_2$O, to yield 2 (3.01 g, 96%): IR (ATR, neat) 3232, 2906 (br), 2693, 1568, 1508, 1242, 1177 cm$^{-1}$; $^1$H NMR (DMSO-d$_6$, 600 MHz) δ 10.11 (bs, 3H), 7.44-7.40 (m, 2H), 7.40-7.35 (m, 2H), 7.33-7.29 (m, 1H), 7.01-6.93 (m, 4H), 5.05 (s, 2H); $^{13}$C NMR (DMSO-d$_6$, 150 MHz) δ 153.7, 139.1, 137.3, 128.5, 128.4, 128.3, 127.9, 127.7, 127.5, 117.1, 116.9, 115.5, 115.3, 69.5; HRMS (EI) m/z calcd for C$_{13}$H$_{14}$N$_2$O 214.1106, found 214.1110.

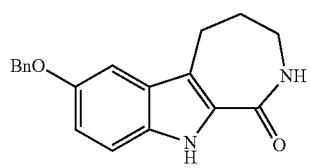

3,4,5,10-Tetrahydro-7-benzyloxy-azepino[3,4-b]indol-1(2H)-one (3)

A mixture of 2 (632 mg, 2.52 mmol) and 1 (390 mg, 2.01 mmol) in anhydrous EtOH (3 mL) and $H_2SO_4$ (0.30 mL) was heated at reflux for 5 h. The reaction was allowed to reach room temperature and the resulting black solid was filtered, washed with water and $Et_2O$, preadsorbed on $SiO_2$ and purified by chromatography on $SiO_2$ (7:3, DCM/acetone) to yield 3 (328 mg, 53%) as a light orange solid: IR (ATR, neat) 3227, 3194, 3033, 2920, 1623, 1543, 1478, 1453, 1276, 1197 $cm^{-1}$; $^1H$ NMR (DMSO-$d_6$, 600 MHz) δ 11.03 (s, 1H), 7.95 (bs, 1H), 7.50-7.42 (d, 2H), 7.41-7.33 (m, 2H), 7.32-7.29 (m, 2H), 7.11 (bs, 1H), 6.97-6.91 (m, 1H), 5.10 (s, 2H), 3.38-3.34 (m, 2H), 2.96 (bs, 2H), 2.02 (bs, 2H); $^{13}C$ NMR (DMSO-$d_6$, 150 MHz) δ 164.1, 152.2, 137.6, 131.2, 128.4, 127.8, 127.7, 127.6, 116.4, 115.6, 113.0, 102.2, 69.7, 41.6, 26.8, 25.4; HRMS (EI) m/z calcd for $C_{19}H_{18}N_2O_2$ 306.1368, found 306.1366.

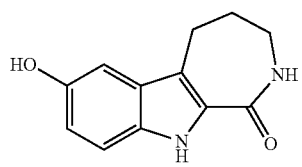

kb-NB123-57

3,4,5,10-Tetrahydro-7-hydroxy-azepino[3,4-b]indol-1(2H)-one (kb-NB123-57)

To a solution of 3 (30.0 mg, 0.0979 mmol) in MeOH (4 mL) was added ammonium formate (100 mg, 1.59 mmol) and 10% Pd/C (20.0 mg, 0.0188 mmol), and the reaction mixture was heated at reflux for 1.5 h under $N_2$. After cooling to room temperature, the mixture was filtered through Celite® and the filtrate was concentrated under reduced pressure to yield a solid residue, which was dissolved in a minimum amount of MeOH, preadsorbed on $SiO_2$ and purified by chromatography on $SiO_2$ (1:1, DCM/acetone) to yield kb-NB123-57 (18.9 mg, 89%) as a light orange solid: IR (ATR, neat) 3362, 3276, 1600, 1545, 1484, 1362 $cm^{-1}$; $^1H$ NMR (DMSO-$d_6$, 300 MHz) δ 10.82 (s, 1H), 8.78 (s, 1H), 7.86 (t, 1H, J=4.5 Hz), 7.19 (d, 1H, J=8.7 Hz), 6.79 (d, 1H, J=1.8 Hz), 6.73 (dd, 1H, J=8.7, 2.3 Hz), 3.30-3.22 (m, 2H), 2.91 (t, 2H, J=6.3 Hz), 2.07-1.94 (m, 2H); $^{13}C$ NMR (DMSO-$d_6$, 150 MHz) δ 164.2, 150.5, 130.5, 128.1, 127.6, 115.7, 115.2, 112.7, 102.8, 41.6, 26.9, 25.4; HRMS (EI) m/z calcd for $C_{12}H_{12}N_2O_2$ 216.0899, found 216.0898.

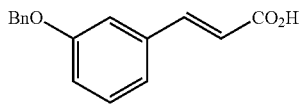

4

(E)-3-(3-(Benzyloxy)phenyl)prop-2-enoic acid (4).[3]

To a stirred suspension of 3-hydroxycinnamic acid (5.00 g, 30.5 mmol) in EtOH (100 mL) was added 1 M aq. NaOH (65 mL) and the reaction mixture was stirred for 5 min, then treated with benzyl bromide (3.72 mL, 31.1 mmol) and stirred for 14 h at room temperature under $N_2$. The mixture was concentrated under reduced pressure to yield a white solid, which was suspended in water (400 mL) and acidified with conc. aq. HCl. The mixture was filtered and the resulting solid was washed with water and $Et_2O$, then dried under high vacuum to give 4 (7.10 g, 92%) as a white solid: IR (ATR, neat) 3400-2500 (br), 1691, 1629, 1577, 1260 $cm^{-1}$; $^1H$ NMR (DMSO-$d_6$, 600 MHz) δ 7.49 (d, 1H, J=16.0 Hz), 7.46 (app d, 2H, J=7.4 Hz), 7.39 (t, 2H, J=7.6 Hz), 7.35-7.29 (m, 3H), 7.22 (d, 1H, J=7.6 Hz), 7.03 (dd, 1H, J=8.2, 2.3 Hz), 6.56 (d, 1H, J=16.0 Hz), 5.14 (s, 2H); $^{13}C$ NMR (DMSO-$d_6$, 150 MHz) δ 168.1, 158.7, 142.7, 137.0, 136.1, 130.0, 128.5, 128.0, 127.9, 121.2, 120.9, 116.8, 113.7, 69.3; HRMS (EI) m/z calcd for $C_{16}H_{14}O_3$ 254.0943, found 254.0950.

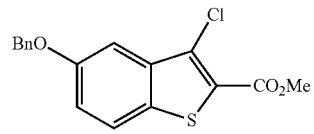

5

Methyl 5-(benzyloxy)-3-chlorobenzo[b]thiophene-2-carboxylate (5)

To a mixture of 4 (8.80 g, 34.6 mmol) in chlorobenzene (50 mL), anhydrous pyridine (0.26 mL, 3.29 mmol) and anhydrous DMF (2.60 mL) was added dropwise $SOCl_2$ (12.6 mL, 173 mmol) at room temperature. The reaction mixture was heated at 120° C. for 22 h under $N_2$. The solution was concentrated by rotary evaporation and traces of pyridine were removed by azeotropic distillation with toluene. The resulting brown oil was dried under high vacuum overnight to yield a brown solid, which was suspended in $Et_2O$, filtered and dried under high vacuum to yield 3-chloro-5-(benzyloxy)-benzo[b]thiophene-2-carbonyl chloride (5.87 g). Upon cooling the filtrate, a second crop of product (1.25 g) was collected by filtration (7.12 g, 61% combined yield). Representative experimental data are as follows: Mp 138-143° C. (lit Mp 139-142° C.);[3] IR (ATR, neat) 1745, 1602, 1483, 1284, 1158 $cm^{-1}$; $^1H$ NMR (DMSO-$d_6$, 600 MHz) δ 8.01 (d, 1H, J=8.8 Hz), 7.50 (d, 2H, J=7.3 Hz), 7.44 (d, 1H, J=2.3 Hz), 7.41 (t, 2H, J=7.3 Hz), 7.37-7.33 (m, 2H), 5.25 (s, 2H); MS (EI) m/z 338 (90), 336 ($M^+$, 100), 303 (40), 301 ($[M-Cl]^+$, 88).

To a suspension of the precursor 3-chloro-5-(benzyloxy)-benzo[b]thiophene-2-carbonyl chloride (516 mg, 1.53 mmol) in anhydrous MeOH (30 mL) was added anhydrous $Et_3N$ (0.43 mL, 3.06 mmol) and the reaction mixture was heated at reflux for 12 h under $N_2$. The solution was concentrated under reduced pressure and the residue was purified by chromatography on ($SiO_2$, hexanes to 9:1, hexanes/EtOAc) to yield 5 (392 mg, 77%) as a light yellow solid. Representative experimental data are as follows: IR (ATR, neat) 1682, 1602, 1509, 1305, 1192 $cm^{-1}$; $^1H$ NMR (DMSO-$d_6$, 600 MHz) δ 8.03 (d, 1H, J=8.9 Hz), 7.50 (d, 2H, J=7.6 Hz), 7.46 (s, 1H), 7.41 (t, 2H, J=7.6 Hz), 7.39-7.33 (m, 2H), 5.25 (s, 2H), 3.89 (s, 3H); $^{13}C$ NMR (DMSO-$d_6$, 150 MHz) δ 160.8, 157.3, 137.3, 136.6, 130.6, 128.5, 128.0, 127.9, 126.4, 125.2, 124.7, 120.3, 105.4, 69.7, 52.8; HRMS (EI) m/z calcd for $C_{17}H_{13}ClO_3S$ 332.0274, found 332.0268.

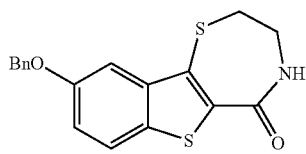

3,4-Dihydro-9-benzyloxy-[1]benzothieno[2,3-f]-1,4-thiazepin-5(2H)-one (6)

To a solution of 5 (390 mg, 1.17 mmol) in anhydrous DMF (8 mL) was added cysteamine.HCl (533 mg, 4.69 mmol) and DBU (1.42 mL, 9.38 mmol) at room temperature under $N_2$. The reaction mixture was stirred at room temperature for 1.5 h and heated to 70° C. for 12 h, then diluted with EtOAc (15 mL) and washed with 2 M aq. HCl (15 mL) to give a white precipitate, which was filtered, triturated with water and $Et_2O$, and dried under high vacuum to yield 6 (260 mg) as a white solid. The layers of the filtrate were separated and the aqueous phase was extracted with EtOAc (3×30 mL). The combined organic layers were washed with brine (1×100 mL), dried ($MgSO_4$) and concentrated to give a yellow precipitate, which was suspended in hexanes/EtOAc (1:1), filtered, triturated with $Et_2O$ and dried under high vacuum to yield a second crop of 6 (90.0 mg) as an off-white solid. The overall amount obtained was 350 mg (87%). Representative experimental data are as follows: Mp 247-249° C.; IR (ATR, neat) 3165, 3037, 1650, 1500, 1282 cm$^{-1}$; $^1$H NMR (DMSO-$d_6$, 600 MHz) δ 8.47 (t, 1H, J=5.6 Hz), 7.90 (d, 1H, J=8.8 Hz), 7.49 (d, 2H, J=7.5 Hz), 7.40 (t, 2H, J=7.7 Hz), 7.36-7.32 (m, 1H), 7.29-7.27 (m, 1H), 7.26-7.23 (m, 1H), 5.20 (s, 2H), 3.64-3.60 (m, 2H), 3.41-3.37 (m, 2H); $^{13}$C NMR (DMSO-$d_6$, 150 MHz) δ 165.1, 156.4, 139.4, 136.9, 133.3, 131.2, 128.5, 127.9, 127.8, 123.8, 118.0, 105.8, 69.6, 42.4, 33.4; HRMS (EI) m/z calcd for $C_{18}H_{15}NO_2S_2$ 341.0544, found 341.0543.

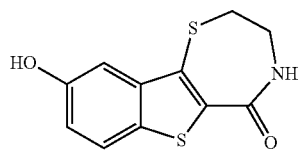

kb-NB142-70

3,4-Dihydro-9-hydroxy-[1]benzothieno[2,3-f]-1,4-thiazepin-5(2H)-one (kb-NB142-70)

To a solution of 6 (250 mg, 0.732 mmol) in anhydrous DCM (20 mL) at −20° C. was added a 1.0 M solution of $BBr_3$ in DCM (1.10 mL, 1.10 mmol) under $N_2$. The reaction mixture was stirred at −20° C. for 0.5 h, then slowly warmed to 0° C. and stirred for 2 h. The solution was warmed to room temperature, diluted with DCM (20 mL) and poured into ice-water (30 mL) to give a white precipitate, which was filtered, triturated with water and DCM and dried under high vacuum to yield kb-NB142-70 (172 mg, 93%) as a light green solid. Representative experimental data are as follows: Mp 218-220° C. (dec., dark brown), 235-238° C. (dec., melts); IR (ATR, neat) 3269, 1633, 1597, 1496, 1432, 1197 cm$^{-1}$; $^1$H NMR (DMSO-$d_6$, 600 MHz) δ 9.73 (s, 1H), 8.42 (t, 1H, J=5.5 Hz), 7.77 (d, 1H, J=8.7 Hz), 7.11 (d, 1H, J=1.9 Hz), 7.01 (dd, 1H, J=8.7, 1.6 Hz), 3.64-3.59 (m, 2H), 3.40-3.36 (m, 2H); $^{13}$C NMR (DMSO-$d_6$, 150 MHz) δ 165.2, 155.3, 139.6, 132.8, 129.3, 127.1, 123.6, 117.8, 107.0, 42.5, 33.3; HRMS (EI) m/z calcd for $C_{11}H_9NO_2S_2$ 251.0075, found 251.0080.

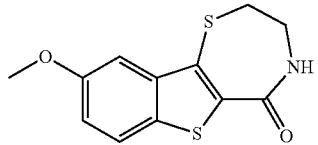

kb-NB165-09

3,4-Dihydro-9-methoxy-[1]benzothieno[2,3-f]-1,4-thiazepin-5(2H)-one (kb-NB165-09).[4]

To a solution of kb-NB142-70 (30.0 mg, 0.119 mmol) in anhydrous DMF (1 mL) was added $K_2CO_3$ (165 mg, 1.19 mmol) followed by MeI (8.0 μL, 0.128 mmol). The reaction mixture was stirred at room temperature for 12 h, excess $K_2CO_3$ was filtered off and the solution was concentrated under reduced pressure. The residue was purified by preparative thin-layer chromatography on $SiO_2$ (1000 μm, EtOAc to 10% MeOH in EtOAc) to yield kb-NB165-09 (29.0 mg, 92%) as a white solid: Mp 202-204° C. (lit. 209-209.5° C.);[4] IR (ATR, neat) 3156, 3018, 2916, 1633, 1499, 1403, 1284 cm$^{-1}$; $^1$H NMR (DMSO-$d_6$, 600 MHz) δ 8.47 (t, 1H, J=5.3 Hz), 7.89 (d, 1H, J=8.3 Hz), 7.19-7.15 (m, 2H), 3.84 (s, 3H), 3.65-3.60 (m, 2H), 3.42-3.38 (m, 2H); $^{13}$C NMR (DMSO-$d_6$, 150 MHz) δ 165.2, 157.4, 139.4, 133.4, 130.9, 127.7, 123.8, 117.5, 104.4, 55.4, 42.4, 33.4; HRMS (EI) m/z calcd for $C_{12}H_{11}NO_2S_2$ 265.0231, found 265.0232.

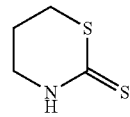

1,3-Thiazinane-2-thione (7).[5]

To a solution of 3-amino-1-propanol (7.61 mL, 100 mmol) in $CCl_4$ (20 mL) at 0° C. was added dropwise chlorosulfonic acid (6.70 mL, 101 mmol) through an addition funnel. Warning: Reaction is very exothermic! The reaction mixture was stirred at room temperature overnight and then concentrated under reduced pressure to yield a solid residue, which was suspended in MeOH (40 mL), filtered, triturated with MeOH, and dried under high vacuum to yield 3-aminopropyl hydrogen sulfate (12.5 g, 80%) as a white powder:[5] IR (ATR, neat) 3128, 3069, 2979, 1198, 1172, 925 cm$^{-1}$; $^1$H NMR (DMSO-$d_6$, 600 MHz) δ 7.65 (bs, 3H), 3.81 (t, 2H, J=6.1 Hz), 2.86 (app dq, 2H, J=12.8, 6.0 Hz), 1.83-1.77 (m, 2H); $^{13}$C NMR (DMSO-$d_6$, 150 MHz) δ 62.9, 36.6, 27.2.

To a suspension of the precursor 3-aminopropyl hydrogen sulfate (12.0 g, 77.3 mmol) and $CS_2$ (5.60 mL, 92.8 mmol) in 50% aq. (v/v) EtOH (33 mL) at 0° C. was slowly added a solution of NaOH (6.80 g, 170 mmol) in 50% aq. (v/v) EtOH (15.0 mL). The reaction mixture was heated at reflux for 40 min and then cooled down to room temperature, resulting in the formation of off-white crystals, which were filtered, washed with ice-cold water and dried under high vacuum to yield the first crop of 7 (7.85 g). Upon cooling the filtrate to 0° C., more crystals formed, and they were filtered, washed with ice-cold water and dried under high vacuum to yield the second crop of 7 (0.790 g). The overall amount of 7 was 8.64 g (84%) obtained as an off-white crystalline solid: IR (ATR, neat) 3128, 3039, 2917, 1539, 1326 cm$^{-1}$; $^1$H NMR (DMSO-d$_6$, 600 MHz) δ 10.22 (s, 1H), 3.29 (t, 2H, J=4.9 Hz), 2.97-2.93 (m, 2H), 1.99-1.94 (m, 2H); $^{13}$C NMR (DMSO-d$_6$, 150 MHz) δ 191.7, 43.5, 29.7, 20.2; MS (EI) m/z 133 (M$^+$, 100), 134 (6), 135 (9); HRMS (EI) m/z calcd for C$_4$H$_7$NS$_2$ 133.0020, found 133.0016.

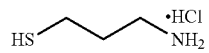

3-Aminopropanethiol hydrochloride (8).$^5$

A suspension of 7 (7.70 g, 57.8 mmol) in conc. aq. HCl (50 mL) was heated at reflux for 2 weeks under N$_2$. After cooling to room temperature, the residual aq. HCl was removed by vacuum distillation (P=5 mmHg) under mild heating (60° C.) for 1 h. The solid residue was suspended in a degassed solution of Et$_2$O/EtOH (9:1, 50 mL) and stirred for 10 min at room temperature under argon, then poured into a coarse fitted Schlenk filter under argon and thoroughly washed with a degassed solution of Et$_2$O/EtOH (9:1), to give a white solid, which was dried in the Schlenk filter under high vacuum overnight to yield the first crop of solid as a mixture of 8 and the corresponding disulfide (4.35 g). A second crop of solid was collected by filtration into a regular coarse fritted funnel under air to yield pure disulfide (38.0 mg). The overall yield based on mass recovery was 64% (4.73 g) of a white, highly hygroscopic solid that requires storage in a vacuum dessicator containing drierite: Spectroscopic data for crop 1 [disulfide (57%)+8 (43%)]: IR (ATR, neat) 2894 (br), 2965 (br), 1607, 1493 cm$^{-1}$; major product (disulfide): $^1$H NMR (D$_2$O, 600 MHz) δ 3.14-3.10 (m, 2H), 2.81 (t, 2H, J=7.1 Hz), 2.14-2.07 (m, 2H); $^{13}$C NMR (D$_2$O, 150 MHz) δ 40.9, 36.5, 28.8; minor product (8): $^1$H NMR (D$_2$O, 600 MHz) δ 3.14-3.10 (m, 2H), 2.63 (t, 2H, J=7.0 Hz), 2.00-1.94 (m, 2H); $^{13}$C NMR (DMSO-d$_6$, 150 MHz) δ 40.9, 33.4, 23.4.

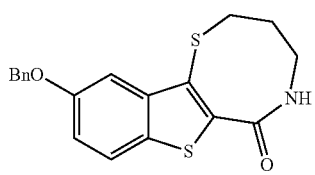

2,3,4,5-Tetrahydro-10-benzyloxybenzo[b]thieno[2,3-f]-1,5-thiazocin-6-one (9). To a solution of 5 (300 mg, 0.901 mmol) in anhydrous, degassed DMF (7.5 mL) was added hydrochloride salt 8 (1.15 g, 3.88 mmol, 43% purity) followed by degassed DBU (1.50 mL, 9.93 mmol) under argon. The reaction mixture was stirred at room temperature for 2 h, then warmed to 70° C. and stirred for 18 h. After cooling to room temperature, the solution was diluted with EtOAc (30 mL) and washed with 2 M aq. HCl (30 mL). The aqueous phase was extracted with EtOAc (3×30 mL) and the combined organic layers were washed with brine (1×150 mL), dried (MgSO$_4$) and concentrated to yield a yellow oil, which was dried under high vacuum to remove residual DMF. The residue was preloaded on SiO$_2$ and purified by chromatography on SiO$_2$ (hexanes to 5% MeOH in EtOAc) to give a yellow solid, which was suspended in Et$_2$O/MeOH (9:1), filtered, triturated with Et$_2$O and dried under high vacuum to yield 9 (133 mg, 42%) as a white solid: Mp 198-199° C.; IR (ATR, neat) 3162, 3033, 2937, 1644, 1619, 1600, 1497, 1384, 1274, 1193 cm$^{-1}$; $^1$H NMR (DMSO-d$_6$, 600 MHz) δ 8.02 (bs, 1H), 7.90-7.84 (m, 1H), 7.51-7.45 (m, 2H), 7.43-7.37 (m, 2H), 7.36-7.31 (m, 1H), 7.26-7.19 (m, 2H), 5.20 (s, 2H), 3.50-3.43 (m, 2H), 3.30-3.24 (m, 2H), 1.92-1.89 (m, 2H); $^{13}$C NMR (DMSO-d$_6$, 150 MHz) δ 164.8, 156.4, 138.7, 136.9, 130.3, 128.5, 128.5, 127.9, 127.7, 127.4, 123.6, 117.3, 105.8, 69.6, 30.5, 27.4; MS (EI) m/z, 355 (M$^+$, 100), 356 (23), 357 (12); HRMS (EI) m/z calcd for C$_{19}$H$_{17}$NO$_2$S$_2$ 355.0701, found 355.0689.

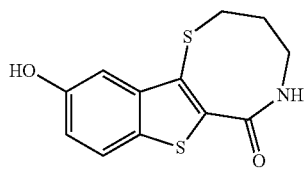

2,3,4,5-Tetrahydro-10-hydroxybenzo[b]thieno[2,3-f]-1,5-thiazocin-6-one (kb-NB165-92). To a suspension of 9 (54.0 mg, 0.152 mmol) in anhydrous DCM (5 mL) at −20° C. was added a 1 M solution of BBr$_3$ in DCM (0.30 mL, 0.300 mmol) under N$_2$. The reaction mixture was stirred at −20° C. for 30 min, warmed to 0° C. and stirred for 1 h, and finally warmed to room temperature and stirred for another 30 min. The solution was diluted with DCM (5 mL) and quenched with cold water (10 mL), resulting in the formation of a white solid, which was filtered, triturated with water, DCM and Et$_2$O, and dried under high vacuum to yield kb-NB165-92 (23.5 mg) as an off-white solid. The filtrate was concentrated and purified by preparative thin-layer chromatography on SiO$_2$ (1000 μm, 5% to 15% MeOH in DCM) to yield kb-NB165-92 (13.5 mg). The overall amount of kb-NB165-92 was 37.0 mg (92%) obtained as an off-white solid: Mp 139-142° C.; IR (ATR, neat) 3256 (br), 3169 (br), 1615, 1492, 1444, 1182 cm$^{-1}$; $^1$H NMR (DMSO-d$_6$, 600 MHz) δ 9.71 (s, 1H), 7.97 (t, 1H, J=7.8 Hz), 7.74 (d, 1H, J=8.6 Hz), 7.09 (s, 1H), 6.98 (d, 1H, J=8.6 Hz), 3.50-3.43 (m, 2H), 3.30-3.23 (m, 2H), 1.92-1.85 (m, 2H); $^{13}$C NMR (DMSO-d$_6$, 150 MHz) δ 164.9, 155.3, 139.0, 128.4, 127.0, 123.4, 117.1, 106.8, 30.5, 27.3; MS (EI) m/z 265 (M$^+$, 100), 266 (15), 267 (11); HRMS (EI) m/z calcd for C$_{12}$H$_{11}$NO$_2$S$_2$ 265.0231, found 265.0230.

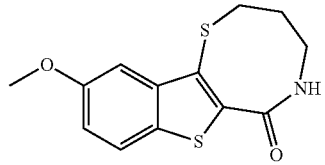

2,3,4,5-Tetrahydro-10-methoxybenzo[b]thieno[2,3-f]-1,5-thiazocin-6-one (kb-NB184-02). To a solution of kb-NB165-92 (19.0 mg, 0.0716 mmol) in anhydrous DMF (1.5 mL) was added K$_2$CO$_3$ (0.100 g, 0.724 mmol) followed by MeI (4.5 µL, 0.0720 mmol). The reaction mixture was stirred at room temperature overnight, quenched with water (15 mL) and extracted with EtOAc (15 mL). The aqueous phase was further extracted with EtOAc (3×15 mL) and the combined organic layers were washed with brine (1×50 mL), dried (MgSO$_4$), concentrated and purified by preparative thin-layer chromatography on SiO$_2$ (1000 µm, 5% to 15% MeOH in EtOAc) to yield kb-NB184-02 (15.5 mg, 77%) as a white solid: Mp 185-188° C.; IR (ATR, neat) 3152, 3026, 2939, 1636, 1498, 1395, 1209 cm$^{-1}$; $^1$H NMR (DMSO-d$_6$, 600 MHz) δ 8.02 (t, 1H, J=7.1 Hz), 7.87 (d, 1H, J=9.4 Hz), 7.16-7.13 (m, 2H), 3.84 (s, 3H), 3.50-3.44 (m, 2H), 3.30-3.26 (m, 2H), 1.92-1.87 (m, 2H); $^{13}$C NMR (DMSO-d$_6$, 150 MHz) δ 164.8, 157.4, 138.7, 130.1, 127.4, 123.6, 116.8, 104.3, 55.4, 30.5, 27.4; MS (EI) m/z 279 (M$^+$, 100), 280 (16); HRMS (EI) m/z calcd for C$_{13}$H$_{13}$NO$_2$S$_2$ 279.0388, found 279.0379.

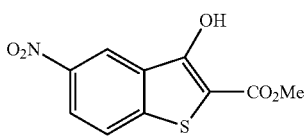

Methyl 3-hydroxy-5-nitrobenzo[b]thiophene-2-carboxylate (10)

Methyl thioglycolate (2.6 mL, 27.3 mmol) was added to a solution of methyl 2-chloro-5-nitrobenzoate (5.00 g, 22.7 mmol) in dry MeOH (100 mL), followed by addition of Et$_3$N (9.6 mL, 68.2 mmol) with stirring over a period of ca. 5 min. The resulting yellow solution was vigorously stirred at room temperature under N$_2$, becoming rapidly red then dark red. A precipitate formed after 30 min. The mixture was heated to 40-50° C. and stirred for 4 h, then poured into a stirred mixture of ice and 1 N aq. HCl (300 mL). The resulting pale yellow precipitate was filtered, rinsed with water and dried by forming an azeotrope with toluene. Recrystallization from toluene (ca. 200 mL) afforded 10 (5.08 g, 88%) as a yellow crystalline powder. Representative experimental data are as follows: Mp 221.4-222.0° C. (softening point: 220° C., toluene); IR (ATR, neat) 3241 (br), 3083, 2963, 1674, 1596, 1582, 1540, 1504, 1437, 1355, 1338, 1318, 1195, 1167, 1139, 1094, 1079, 1049, 978, 915, 911, 828, 783, 770, 738, 671 cm$^{-1}$; $^1$H NMR (DMSO-d$_6$, 300 MHz) δ 11.21 (bs, 1H), 8.80 (d, 1H, J=2.1 Hz), 8.31 (dd, 1H, J=9.0, 2.4 Hz), 8.21 (d, 1H, J=9.0 Hz), 3.86 (s, 3H); $^{13}$C NMR (DMSO-d$_6$, 100 MHz) δ 163.2, 155.2, 145.2, 143.4, 132.0, 125.1, 122.4, 118.7, 107.3, 52.6; MS (EI) m/z 253 (M$^+$, 36), 221 ([M-MeOH]$^+$, 100), 119 (60); HRMS (EI) m/z calcd for C$_{10}$H$_7$NO$_5$S 253.0045, found 253.0040.

Methyl 5-nitro-3-(trifluoromethylsulfonyloxy)benzo[b]thiophene-2-carboxylate (11)

To a suspension of 10 (500 mg, 1.97 mmol) in dry DCM (10 mL) at 0° C. were added DMAP (12.3 mg, 0.0987 mmol), Et$_3$N (0.39 mL, 2.76 mmol) and Tf$_2$O (0.47 mL, 2.76 mmol). The resulting solution was stirred at room temperature under argon for 2 h. The reaction mixture was then quenched with sat. aq. NaHCO$_3$ and extracted twice with DCM. The combined organic layers were dried (Na$_2$SO$_4$), filtered and concentrated in vacuo. Chromatography of the residue on SiO$_2$ (8:2 to 7:3, hexanes/EtOAc) afforded 11 (705 mg, 93%) as a pale yellow crystalline powder: Mp 106.7-107.0° C. (softening point: 106.0° C.); IR (ATR, neat) 3098, 2960, 1722, 1603, 1581, 1538, 1517, 1420, 1405, 1344, 1316, 1279, 1230, 1210, 1150, 1124, 1111, 1088, 1062, 1034, 966, 954, 919, 904, 848, 828, 811, 781, 768, 757, 740, 732, 656 cm$^{-1}$; $^1$H NMR (CDCl$_3$, 300 MHz) δ 8.74 (d, 1H, J=1.5 Hz), 8.43 (dd, 1H, J=9.0, 2.1 Hz), 8.04 (d, 1H, J=9.0 Hz), 4.05 (s, 3H); $^{13}$C NMR (CDCl$_3$, 100 MHz) δ 160.1, 146.7, 142.3, 140.0, 131.2, 127.0, 124.7, 122.7, 118.8 (q, J=319.0 Hz), 118.3 (d, J=1.2 Hz), 53.6; MS (EI) m/z 385 (M$^+$, 28), 252 (99), 196 (100), 68 (76); HRMS (EI) m/z calcd for C$_{11}$H$_6$F$_3$NO$_7$S$_2$ 385.9538, found 385.9534.

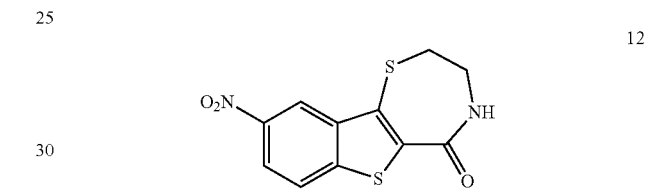

3,4-Dihydro-9-nitro-[1]benzothieno[2,3-f]-1,4-thiazepin-5(2H)-one (12)

To a solution of triflate 11 (632 mg, 1.64 mmol) in dry DMF (9.2 mL) were added cysteamine.HCl (745 mg, 6.56 mmol) and then DBU (2.0 mL, 13.1 mmol). The resulting dark red mixture was stirred at room temperature under argon for 1.5 h. The slurry was then heated at 70° C. for 13 h, then diluted with EtOAc and 2 N aq. HCl was added. The resulting yellow mixture was filtered, and the solid boiled in toluene, filtered immediately over a hot filter, rinsed with toluene and dried to afford 12 (231 mg, 50%, 67% b.r.s.m.) as a yellow powder. An additional 105 mg (25%) of 10 was recovered from the filtrate. Representative experimental data for 12 are as follows: Mp 294-296° C. (dec.); IR (ATR, neat) 3262, 3150, 3020, 2915, 1640, 1597, 1567, 1515, 1495, 1467, 1454, 1439, 1418, 1402, 1346, 1327, 1286, 1258, 1245, 1232, 1189, 1139, 1096, 1081, 1016, 965, 923, 885, 878, 829, 811, 734 cm$^{-1}$; $^1$H NMR (DMSO-d$_6$, 300 MHz) δ 8.71 (bt, 1H, J=5.4 Hz), 8.53 (t, 1H, J=1.5 Hz), 8.32 (d, 2H, J=1.5 Hz), 3.73-3.63 (m, 2H), 3.52-3.43 (m, 2H); $^{13}$C NMR (DMSO-d$_6$, 100 MHz) δ 164.4, 145.2, 144.8, 138.2, 135.6, 129.4, 124.5, 120.9, 118.1, 42.3, 33.4; MS (EI) m/z 280 (M$^+$, 100); HRMS (EI) m/z calcd for C$_{11}$H$_8$N$_2$O$_3$S$_2$ 279.9976, found 279.9974.

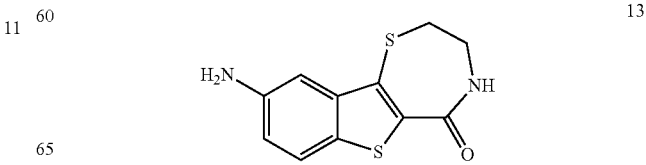

3,4-Dihydro-9-amino-[1]benzothieno[2,3-f]-1,4-thiazepin-5(2H)-one (13, or mcf292-03)

To a suspension of 12 (250 mg, 0.892 mmol) in degassed EtOH (9 mL) was added SnCl$_2$ (1.73 g, 8.92 mmol). The resulting suspension was heated at reflux for 5 h under argon, then quenched with 2.5 N aq. NaOH and extracted with hot 8:2 CHCl$_3$/i-PrOH (9×50 mL). The combined organic layers were washed with water (2×), brine (2×), dried (Na$_2$SO$_4$), filtered and concentrated in vacuo to afford crude 13 (158 mg, 71%) as a dark orange powder. A sample (ca. 30 mg) was further purified by chromatography on SiO$_2$ (5:5 hexanes/EtOAc to EtOAc) to afford pure 13 (28.2 mg) as a yellow powder: Mp 198.6-199.0° C.; IR (ATR, neat) 3370, 3254, 3146, 3008, 2915, 1623, 1599, 1556, 1491, 1454, 1430, 1403, 1346, 1333, 1312, 1286, 1243, 1204, 1184, 1129, 1083, 975, 887, 837, 798, 766, 749, 719, 691, 677, 663 cm$^{-1}$; $^1$H NMR (CD$_3$OD, 400 MHz) δ 7.58 (dd, 1H, J=8.8, 0.4 Hz), 7.15 (dd, 1H, J=2.4, 0.4 Hz), 6.98 (dd, 1H, J=8.8, 2.0 Hz), 3.77-3.71 (m, 2H), 3.42-3.37 (m, 2H); $^{13}$C NMR (CD$_3$OD, 100 MHz) δ 169.3, 147.0, 141.5, 132.4, 130.8, 130.7, 124.0, 119.7, 108.4, 44.3, 35.1; MS (EI) m/z 250 (M$^+$, 100); HRMS (EI) m/z calcd for C$_{11}$H$_{10}$N$_2$OS$_2$ 250.0235, found 250.0225.

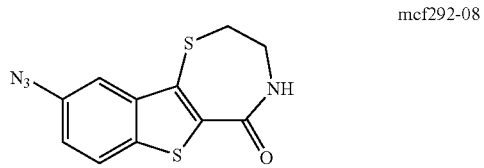 [SMILES: [N-]=[N+]=Nc1ccc2sc3c(c2c1)SCCNC3=O]

mcf292-08

3,4-Dihydro-9-azido-[1]benzothieno[2,3-f]-1,4-thiazepin-5(2H)-one (mcf292-08)

To a suspension of crude aniline 13 (50.0 mg, 0.200 mmol) in MeCN (0.5 mL) were added t-BuONO (53 μL, 0.399 mmol) and then TMSN$_3$ (45 μA, 0.320 mmol) dropwise at 0° C. The reaction mixture was stirred at room temperature in the dark for 1.5 h, then diluted in CHCl$_3$ (ca. 60 mL) and stirred with 2.5 N aq. NaOH (ca. 50 mL) for 1 h. The layers were then separated, the organic layer washed with water (20 mL), dried (K$_2$CO$_3$), filtered and concentrated in vacuo. Chromatography of the residue on SiO$_2$ (CHCl$_3$ to 98:2 CHCl$_3$/MeOH) afforded a fraction that was dissolved in CHCl$_3$ and stirred with 2.5 N aq. NaOH for 2 h. The layers were then separated, and the organic layer was stirred with 2.5 N aq. NaOH for 1 h. The procedure was repeated 4 times (1×30 min and 3×15 min stirring). The layers were then separated, the organic layer was washed with water, dried (K$_2$CO$_3$), filtered and concentrated in vacuo to yield mcf292-08 (29.4 mg, 53%, 38% over 2 steps, 96% purity estimated by $^1$H NMR) as a beige powder: Mp 193° C. (dec.); IR (ATR, neat) 3260, 3154, 3016, 2922, 2115, 1631, 1592, 1495, 1467, 1441, 1422, 1400, 1340, 1284, 1252, 1234, 1215, 1198, 1144, 1113, 975, 889, 835, 809, 792, 751, 721 cm$^{-1}$; $^1$H NMR (DMSO-d$_6$, 400 MHz) δ 8.53 (bt, 1H, J=5.6 Hz), 8.06 (d, 1H, J=8.8 Hz), 7.39 (d, 1H, J=1.6 Hz), 7.31 (dd, 1H, J=8.6, 2.2 Hz), 3.68-3.60 (m, 2H), 3.45-3.38 (m, 2H); $^{13}$C NMR (DMSO-d$_6$, 100 MHz) δ 164.9, 139.4, 136.9, 135.2, 134.2, 127.7, 124.6, 119.2, 112.0, 42.4, 33.4; MS (EI) m/z 276 (M$^+$, 14), 248 ([M−N$_2$]$^+$, 50), 68 (100); HRMS (EI) m/z calcd for C$_{11}$H$_8$N$_4$OS$_2$ 276.0140, found 276.0137.

14

Thieno[3,2-d]pyrimidine-2,4-diol (14)

To a solution of methyl 3-aminothiophene-2-carboxylate (5.00 g, 31.8 mmol) in glacial AcOH (35.0 mL) and H$_2$O (31 mL) was added KOCN (8.06 g, 95.4 mmol) in H$_2$O (18.0 mL) dropwise. The resulting slurry was stirred at room temperature for 20 h, and filtered. The solid was placed in a flask, flushed with N$_2$, treated with 2 N aq. NaOH (85 mL), and stirred at room temperature for 3 h. The slurry was filtered to remove any undissolved material. The solution was acidified with conc. aq. HCl until a pH of 5-6 was obtained. The precipitate was filtered and the solid was dried at 50° C. to provide 14 (3.49 g, 65%) as a white solid: $^1$H NMR (DMSO-d$_6$, 300 MHz) δ 11.56 (s, 1H), 11.21 (s, 1H), 8.05 (d, 1H, J=5.3 Hz), 6.90 (d, 1H, J=5.3 Hz).

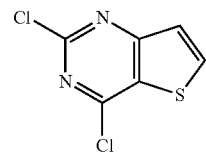

15

2,4-Dichlorothieno[3,2-d]pyrimidine (15)

To a solution of 14 (500 mg, 2.97 mmol) and N,N-dimethylaniline (0.29 mL, 2.23 mmol) in MeCN (2.5 mL) cooled to 0° C. was slowly added POCl$_3$ (1.4 mL, 14.9 mmol). The purple slurry was heated to 80-85° C. and stirred for 48 h. A second portion of POCl$_3$ (1.0 mL) was added after 24 h. The resulting clear purple solution was poured into ice and water and stirred for 5 min. The slurry was filtered, and the solid was dried at 45° C. The solid was dissolved in EtOAc, washed with sat. aq. NaHCO$_3$, and stirred with activated charcoal. The solution was filtered through Celite® and concentrated to provide 15 (482 mg, 79%) as a yellow solid: Mp 138.8-139.3° C. (H$_2$O); IR (ATR, neat) 3066, 3088, 1545, 1508, 1307, 1204, 798 cm$^{-1}$; $^1$H NMR (DMSO-d$_6$, 300 MHz) δ 8.70 (d, 1H, J=5.4 Hz), 7.74 (d, 1H, J=5.4 Hz); $^{13}$C NMR (DMSO-d$_6$, 75 MHz) δ 163.6, 154.8, 154.7, 142.4, 129.3, 124.1; HRMS (EI) m/z calcd for C$_6$H$_2$N$_2$SCl$_2$ 203.9316, found 203.9312.

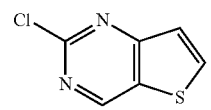

16

2-Chlorothieno[3,2-d]pyrimidine (16)

To a solution of 15 (44.0 mg, 0.022 mmol) and NaHCO$_3$ (27.0 mg, 0.32 mmol) in EtOH (2.0 mL) was added 10%

Pd/C (8.90 mg, 20% by wt). The suspension was stirred at room temperature under an atmosphere of H$_2$ for 23 h. A second portion of 10% Pd/C (8.90 mg, 20% by wt) was added after 12 h. The reaction mixture was filtered through Celite® with EtOAc washings. The filtrate was washed with H$_2$O/brine (4:1), dried (MgSO$_4$), and concentrated under reduced pressure to provide 16 (33.0 mg, 90%) as white solid: Mp 164.9-165.5° C. (EtOAc); IR (ATR, neat) 3105, 3051, 2924, 1543, 1515, 1456, 1420, 1334, 1349, 1301, 1159, 794 cm$^{-1}$; $^1$H NMR (DMSO-d$_6$, 300 MHz) δ 9.50 (s, 1H), 8.64 (d, 1H, J=5.4 Hz), 7.64 (d, 1H, J=5.4 Hz); $^{13}$C NMR (DMSO-d$_6$, 75 MHz) δ 162.7, 156.3, 155.3, 142.2, 130.1, 122.9; MS (EI) m/z 170 (M$^+$, 100), 135 (72); HRMS (EI) m/z calcd for C$_6$H$_3$N$_2$SCl 169.9705, found 169.9700.

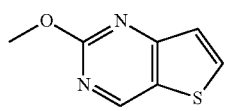

2-Methoxythieno[3,2-d]pyrimidine (17)

To a solution of 16 (146 mg, 0.86 mmol) in MeOH (20 mL) was added NaOMe (130 mg, 2.41 mmol). The solution was heated at reflux for 37 h. An additional 1.4 equiv of NaOMe (65.0 mg) was added after 24 h (Note: The reaction was complete in 7 h with comparable yields when 4.2 equiv of NaOMe were added at the start of the reaction). The reaction mixture was cooled to room temperature, quenched with 1 N aq. HCl (2.0 mL), and extracted with DCM (4×10 mL). The combined organic layers were washed with H$_2$O (10 mL), dried (MgSO$_4$), and concentrated under reduced pressure to provide 17 (125 mg, 88%) as an off-white solid: Mp 167.0-168.5° C. (DCM); IR (ATR, neat) 3071, 3025, 2917, 1558, 1528, 1478, 1379, 1295, 1249, 1031, 796, 677 cm$^{-1}$; $^1$H NMR (DMSO-d$_6$, 300 MHz) δ 9.30 (d, 1H, J=0.6 Hz), 8.45 (d, 1H, J=5.4 Hz), 7.47 (dd, 1H, J=5.4, 0.7 Hz), 3.96 (s, 3H); $^{13}$C NMR (DMSO-d$_6$, 75 MHz) δ 163.4, 162.4, 154.8, 139.9, 124.8, 122.9, 54.6; MS (EI) m/z 166 (M$^+$, 29), 84 (100); HRMS (EI) m/z calcd for C$_7$H$_6$N$_2$OS 166.0201, found 166.0201.

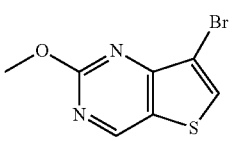

7-Bromo-2-methoxythieno[3,2-d]pyrimidine (18)

To a reaction vial containing 17 (100 mg, 0.602 mmol) and AcOH (1.5 mL) under an atmosphere of N$_2$ was added Br$_2$ (0.093 mL, 1.81 mmol). The reaction vial was sealed and heated to 70° C. for 24 h. The mixture was cooled to room temperature, quenched with sat. aq. NaHCO$_3$, and extracted with EtOAc. The combined organic layers were washed with sat. aq. Na$_2$S$_2$O$_3$, sat. aq. NaHCO$_3$, and brine, dried (MgSO$_4$) and concentrated under reduced pressure to give a white solid. The solid was adsorbed onto SiO$_2$ and purified by chromatography on SiO$_2$ (1:20 EtOAc/hexanes, 1:10 EtOAc/hexanes, 3:20 EtOAC/hexanes, 100% EtOAc) to provide 18 (58.3 mg, 40%) as a white solid: Mp 115.3-115.9° C. (EtOAc); IR (ATR, neat) 3090, 3019, 2956, 1567, 1524, 1474, 1463, 1370, 1312, 1271 cm$^{-1}$; $^1$H NMR (DMSO-d$_6$, 300 MHz) δ 9.34 (s, 1H), 8.61 (s, 1H), 4.01 (s, 3H); $^{13}$C NMR (DMSO-d$_6$, 75 MHz) δ 163.9, 158.4, 155.8, 136.7, 124.0, 106.8, 54.8; HRMS (EI) m/z calcd for C$_7$H$_5$N$_2$OSBr 243.9306, found 243.9304.

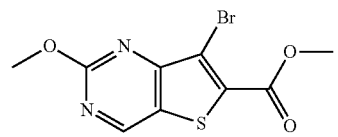

Methyl 7-bromo-2-methoxythieno[3,2-d]pyrimidine-6-carboxylate (19)

To a reaction vial containing 18 (40.0 mg, 0.16 mmol) and THF (0.6 mL) cooled to −55 to −60° C. under an atmosphere of argon was added TMPMgCl.LiCl$^6$ (0.17 mL, 0.22 mmol) dropwise. The white slurry became a clear yellow solution after the addition of TMPMgCl.LiCl and was stirred for 2 h at −55 to −60° C., turning into a pale yellow slurry at the end of this time. Methyl cyanoformate (0.016 mL, 0.20 mmol) in THF (0.10 mL) was added dropwise at −50° C. and the solution was stirred for 2 h while warming to 0° C. The pale yellow slurry turned pale yellow-orange as it warmed to 0° C. The reaction was quenched at 0° C. with sat. aq. NH$_4$Cl (0.5 mL). The mixture was diluted with EtOAc and the organic layer was washed with sat. aq. NH$_4$Cl (2×5 mL). The combined aqueous layers were extracted with EtOAc (2×5 mL). The combined organic layers were washed with brine (5 mL), dried (MgSO$_4$), and concentrated under reduced pressure to provide 19 (48.0 mg, 97%) as a yellow solid: Mp 180.9-181.4° C. (EtOAc); IR (ATR, neat) 2956, 2915, 2848, 1735, 1569, 1472, 1382, 1213, 1031, 788 cm$^{-1}$; $^1$H NMR (DMSO-d$_6$, 300 MHz) δ 9.49 (s, 1H), 4.04 (s, 3H), 3.95 (s, 3H); $^{13}$C NMR (DMSO-d$_6$, 75 MHz) δ 164.1, 160.6, 158.3, 157.4, 136.3, 124.8, 113.9, 55.0, 53.3; MS (EI) m/z 302 (M$^{-1}$, 100), 274 (45); HRMS (ESI) m/z calcd for C$_9$H$_8$BrN$_2$O$_3$S (M+H) 302.9439, found 302.9418.

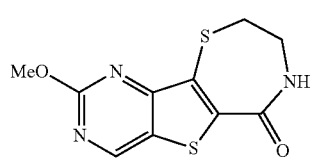

2-Methoxy-7H,8H,9H-1,4-thiazepino[7',6'-5,4]thiopheno[3,2-d]pyrimidin-6-one (kmg-NB4-23)

To a solution of 19 (41.0 mg, 0.14 mmol) in DMF (1.3 mL) under an atmosphere of N$_2$ was added cysteamine.HCl (63.0 mg, 0.54 mmol) in one portion and DBU (0.17 mL, 1.1 mmol) dropwise. The reaction mixture turned dark blue upon addition of DBU and after stirring for 20 min, the mixture was a pale purple colored slurry. The reaction mixture was stirred at room temperature for 1.5 h, and then heated to 70° C. for 9 h 50 min. The resulting yellow slurry was diluted with EtOAc, washed with 2 N aq. HCl, and filtered (H₂O and EtOAc washings). Residual DMF was removed by azeotropic distillation with heptane to provide kmg-NB4-23 (25.0 mg, 68%) as a pale yellow solid: Mp 308° C. (dec.); IR (ATR, neat) 3260, 3153, 3015, 1636, 1554, 1495, 1467, 1374, 1269, 1353, 1323 cm⁻¹; ¹H NMR (DMSO-d₆, 300 MHz) δ 9.36 (s, 1H), 8.70 (t, 1H, J=5.4 Hz), 3.98 (s, 1H), 3.68 (app dd, 2H, J=6.0 Hz), 3.40-3.36 (m, 2H); ¹³C NMR (DMSO-d₆, 75 MHz) δ 164.2, 163.1, 159.6, 155.9, 138.5, 129.7, 124.1, 54.8, 42.7, 31.9; HRMS (ESI) m/z calcd for C₁₀H₁₀N₃O₂S₂ (M+H) 268.0214, found 268.0237.

Moreover, the following Formula I compounds were synthesized using synthetic protocols described above.

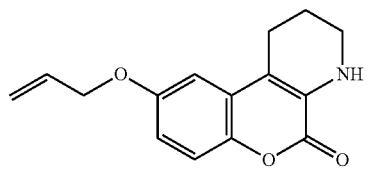 [SMILES: C=CCOc1ccc2oc(=O)c3c(c2c1)CCCN3]

9-Allyloxy-1,2,3,4-tetrahydrochromeno[3,4-b]pyridin-5-one (kb-NB77-83)

Yield: 68%; Mp 90-91° C.; IR (ATR, neat) 3419, 3394, 2917, 2864, 1702, 1599, 1510, 1189 cm⁻¹; ¹H NMR (CDCl₃, 600 MHz) δ 7.20 (d, 1H, J=9.0 Hz), 6.86 (d, 1H, J=3.0 Hz), 6.84 (dd, 1H, J=9.0, 3.0 Hz), 6.11-6.04 (m, 1H), 5.44 (d, 1H, J=16.8 Hz), 5.32 (d, 1H, J=10.2 Hz), 4.74 (bs, 1H), 4.57 (d, 2H, J=5.4 Hz), 3.41-3.37 (m, 2H), 2.79 (t, 2H, J=6.6 Hz), 2.08-2.03 (m, 2H); ¹³C NMR (CDCl₃, 150 MHz) δ 158.8, 155.4, 142.5, 133.3, 129.7, 122.6, 118.0, 117.1, 115.9, 113.0, 106.0, 69.5, 40.6, 21.6, 20.8; HRMS (ES) m/z calcd for C₁₅H₁₅NO₃ ([M+H]⁺) 258.1130, found 258.1138.

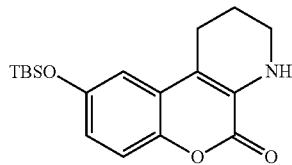 [SMILES: CC(C)(C)[Si](C)(C)Oc1ccc2oc(=O)c3c(c2c1)CCCN3]

9-(tert-Butyldimethylsilyloxy)-1,2,3,4-tetrahydrochromeno[3,4-b]pyridin-5-one (kb-NB77-78)

Yield: 94%; Mp 117-119° C.; IR (ATR, neat) 3418, 2929, 2856, 1721, 1699, 1602, 1508, 1430, 1251, 1172 cm⁻¹; ¹H NMR (CDCl₃, 600 MHz) δ 7.14 (d, 1H, J=9.0 Hz), 6.78 (d, 1H, J=3.0 Hz), 6.73 (dd, 1H, J=9.0, 3.0 Hz), 4.72 (bs, 1H), 3.41-3.35 (m, 2H), 2.67 (t, 2H, J=6.6 Hz), 2.09-2.02 (m, 2H), 1.00 (s, 9H), 0.21 (s, 6H); ¹³C NMR (DMSO-d₆, 150 MHz) δ 157.5, 151.7, 141.9, 129.5, 122.6, 117.1, 116.63, 116.57, 113.9, 111.0, 25.6 (3C), 21.1, 20.0, 18.0, −4.5 (2C); HRMS (ES) m/z calcd for C₁₈H₂₅NO₃Si ([M+H]⁺) 332.1682, found 332.1678.

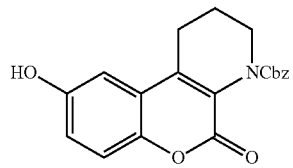 [SMILES: O=C(OCc1ccccc1)N1CCCc2c1c(=O)oc1ccc(O)cc21]

Phenylmethyl 9-hydroxy-5-oxo-1,2,3,4-tetrahydrochromeno[3,4-b]pyridine-4-carboxylate (kb-NB77-91)

Yield: 65%; Mp 235-237° C.; IR (ATR, neat) 3887, 1724, 1679, 1404, 1308, 1261, 1160 cm⁻¹; ¹H NMR (DMSO-d₆, 600 MHz) δ 9.73 (s, 1H), 7.38-7.33 (m, 4H), 7.33-7.28 (m, 1H), 7.23 (d, 1H, J=9.0 Hz), 6.98-6.95 (m, 2H), 5.11 (s, 2H), ~3.30-3.50 (m, 2H), 2.85 (t, 2H, J=6.6 Hz), 1.98-1.88 (m, 2H); ¹³C NMR (DMSO-d₆, 150 MHz) δ 156.2, 154.03, 153.99, 144.8, 138.7, 136.1, 128.4 (2C), 128.0, 127.7 (2C), 125.0, 119.6, 118.4, 117.1, 108.5, 67.4, 44.2, 22.5, 22.1; HRMS (ES) m/z calcd for C₂₀H₁₇NO₅ ([M+Na]⁺) 374.1004, found 374.0991.

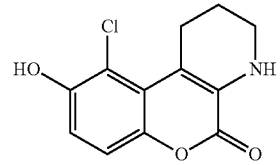 [SMILES: O=c1oc2ccc(O)c(Cl)c2c2c1NCCC2]

10-Chloro-9-hydroxy-1,2,3,4-tetrahydrochromeno[3,4-b]pyridin-5-one (kb-NB96-47-1)

Yield: 6%; Mp 211-213° C.; IR (ATR, neat) 3434, 3225 (br), 2971, 2906, 1666, 1589, 1509, 1339, 1235 cm⁻¹; ¹H NMR (DMSO-d₆, 600 MHz) δ 10.02 (s, 1H), 7.10 (d, 1H, J=9.0 Hz), 6.85 (d, 1H, J=9.0 Hz), 6.24 (bs, 1H), 3.25-3.20 (m, 2H), 3.15 (t, 2H, J=6.6 Hz), 1.80-1.74 (m, 2H); ¹³C NMR (DMSO-d₆, 150 MHz) 156.8, 151.0, 140.9, 130.4, 120.7, 115.5, 113.4, 113.1, 112.4, 26.8, 20.9; HRMS (EI) m/z calcd for C₁₂H₁₀Cl NO₃ (M⁺) 251.0349, found 251.0349.

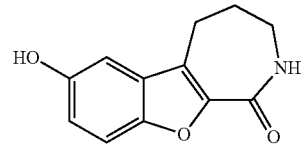 [SMILES: O=C1NCCCc2c1oc1ccc(O)cc21]

7-Hydroxy-2,3,4,5-tetrahydro-[1]benzoxolo[2,3-c]azepin-1-one (CID755673)

Yield: 83%; Mp (i-PrOH) 245-247° C. (lit. 244-247° C.); IR (ATR, neat) 3187 (br), 3059, 2921, 1680, 1579, 1472, 1435, 1339, 1166 cm⁻¹; ¹H NMR (DMSO-d₆, 600 MHz) δ 9.36 (s, 1H), 8.09 (t, 1H, J=4.8 Hz), 7.41 (d, 1H, J=9.0 Hz), 6.92 (d, 1H, J=2.4 Hz), 6.90 (dd, 1H, J=9.0, 2.4 Hz), 3.24 (dd, 2H, J=9, 4.8 Hz), 2.89 (t, 2H, J=6.6 Hz), 2.02-1.98 (m, 2H); ¹³C NMR (DMSO-d₆, 150 MHz) δ 161.9, 153.9, 148.1, 144.3, 129.6, 123.5, 116.9, 112.4, 105.1, 41.2, 26.8, 24.3; HRMS (ESI) m/z calcd for $C_{12}H_{11}NO_3$ ([M+H]$^+$) 218.0817, found 218.0832.

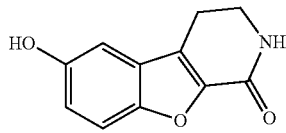

6-Hydroxy-2,3,4-trihydrobenzo[b]pyridino[4,3-d]furan-1-one (kb-NB123-23A). Yield: 77%; Mp 265-268° C.; IR (ATR, neat) 3404, 3158 (bs), 1661, 1588, 1479, 1451, 1339, 1228, 1208, 1184 cm$^{-1}$; $^1$H NMR (DMSO-d$_6$, 600 MHz) δ 9.43 (s, 1H), 7.74 (bs, 1H), 7.47 (d, 1H, J=9.0 Hz), 6.98 (d, 1H, J=2.4 Hz), 6.91 (dd, 1H, J=9.0, 2.4 Hz), 3.50 (td, 2H, J=7.2, 2.4 Hz), 2.88 (t, 2H, J=7.2 Hz); $^{13}$C NMR (DMSO-d$_6$, 150 MHz) δ 159.4, 153.8, 149.0, 144.5, 126.6, 124.6, 116.4, 112.6, 105.1, 40.3, 20.0; HRMS (ES) m/z calcd for $C_{11}H_9NO_3$ ([M+H]$^+$) 203.0582, found 203.0588.

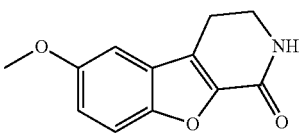 [SMILES: COc1ccc2oc3c(c2c1)CCNC3=O]

7-Methoxy-3,4-dihydrobenzofuro[2,3-c]pyridin-1(2H)-one (kb-NB123-32)

Yield: 94%; Mp 237-241° C.; IR (ATR, neat) 3197, 3088, 2895, 1672, 1585, 1480, 1432, 1329, 1214, 1192 cm$^{-1}$; $^1$H NMR (DMSO-d$_6$, 600 MHz) δ 7.78 (s, 1H), 7.58 (d, 1H, J=9.0 Hz), 7.26 (d, 1H, J=2.4 Hz), 7.06 (dd, 1H, J=9.0, 2.4 Hz), 3.81 (s, 3H), 3.52 (td, 2H, J=7.2, 2.4 Hz), 2.94 (t, 2H, J=7.2 Hz); $^{13}$C NMR (DMSO-d$_6$, 150 MHz) δ 159.3, 156.0, 149.7, 144.7, 126.4, 125.0, 116.5, 112.9, 103.1, 55.7, 40.4, 20.1; HRMS (EI) m/z calcd for $C_{12}H_{11}NO_3$ (M$^+$) 217.0739, found 217.0743.

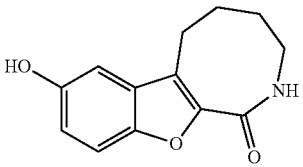

8-Hydroxy-2H,3H,4H,5H,6H-azocino[6,7-d]benzo[b]furan-1-one (kb-NB96-53)

Yield: 77%; Mp 225-232° C.; IR (ATR, neat) 3348, 3166 (br), 2927, 1639, 1578, 1465, 1433, 1216, 1153 cm$^{-1}$; $^1$H NMR (DMSO-d$_6$, 600 MHz) δ 9.33 (s, 1H), 7.98 (t, 1H, J=6.7 Hz), 7.36 (d, 1H, J=8.8 Hz), 6.87 (d, 1H, J=2.2 Hz), 6.85 (dd, 1H, J=8.8, 2.4 Hz), 3.32-3.27 (m, 2H), 2.79-2.74 (m, 2H), 1.92-1.86 (m, 2H), 1.67-1.62 (m, 2H); $^{13}$C NMR (DMSO-d$_6$, 150 MHz) δ 162.9, 153.5, 147.4, 142.6, 129.1, 122.2, 115.4, 111.7, 104.5, 30.2, 22.9, 20.5; HRMS (ES) m/z calcd for $C_{13}H_{13}NO_3$ ([M+Na]$^+$) 254.0793, found 254.0773.

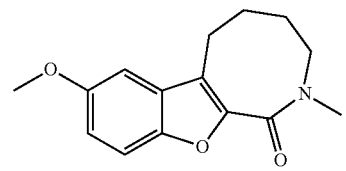

8-Methoxy-2H,3H,4H,5H,6H-azocino[6,7-d]benzo[b]furan-1-one (kb-NB96-59)

Yield: 58%; Mp 261-264° C.; IR (ATR, neat) 3168, 3038, 2928, 1651, 1581, 1478, 1435, 1210, 1152 cm$^{-1}$; $^1$H NMR (DMSO-d$_6$, 600 MHz) δ 8.01 (s, 1H), 7.47 (d, 1H, J=9.0 Hz), 7.12 (s, 1H), 7.00 (d, 1H, J=9.0 Hz), 3.33-3.28 (m, 2H), 3.80 (s, 3H), 2.86-2.81 (m, 2H), 1.93-1.86 (m, 2H), 1.69-1.61 (m, 2H); $^{13}$C NMR (DMSO-d$_6$, 150 MHz) δ 162.9, 155.8, 148.2, 142.9, 128.9, 122.7, 115.5, 112.1, 102.6, 55.7, 30.2, 23.0, 20.5; HRMS (ES) m/z calcd for $C_{14}H_{15}NO_3$ ([M+Na]$^+$) 268.0950, found 268.0970.

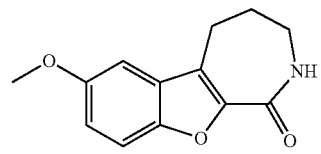 [SMILES: COc1ccc2oc3c(c2c1)CCCNC3=O]

7-Methoxy-2,3,4,5-tetrahydro-[1]benzoxolo[2,3-c]azepin-1-one (kb-NB77-56)

Yield: 74%; Mp 261-263; ° C.; IR (ATR, neat) 3200, 3063, 2936, 1642, 1580, 1474, 1434, 1207, 1163 cm$^{-1}$; $^1$H NMR (DMSO-d$_6$, 600 MHz) δ 8.13 (t, 1H, J=4.8 Hz), 7.53 (d, 1H, J=9.0 Hz), 7.18 (d, 1H, J=2.4 Hz), 7.05 (dd, 1H, J=9.0, 2.4 Hz), 3.81 (s, 3H), 3.27 (dd, 2H, J=9.0, 5.4 Hz), 2.96 (t, 2H, J=6.6 Hz), 2.06-2.00 (m, 2H); $^{13}$C NMR (DMSO-d$_6$, 150 MHz) δ 161.4, 155.7, 148.4, 144.1, 129.0, 123.5, 116.4, 112.3, 102.8, 55.7, 40.8, 26.3, 24.0; HRMS (ES) m/z calcd for $C_{13}H_{14}NO_3$ ([M+H]$^+$) 232.0974, found 232.0966.

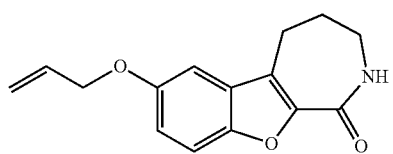 [SMILES: C=CCOc1ccc2oc3c(c2c1)CCCNC3=O]

7-Allyloxy-2,3,4,5-tetrahydro-[1]benzoxolo[2,3-c]azepin-1-one (kb-NB77-84). Yield: 69%; Mp 198-200° C.; IR (ATR, neat) 3189, 3072, 2968, 2912, 1650, 1602, 1585, 1459, 1422, 1201, 1170 cm$^{-1}$; $^1$H NMR (DMSO-d$_6$, 600 MHz) δ 8.13 (t, 1H, J=4.8 Hz), 7.53 (d, 1H, J=9.0 Hz), 7.20 (d, 1H, J=2.4 Hz), 7.08 (dd, 1H, J=9.0, 2.4 Hz), 6.11-6.04 (m, 1H), 5.43 (dd, 1H, J=18, 1.8 Hz), 5.27 (dd, 1H, J=8.4, 1.8 Hz), 4.61 (d, 2H, J=5.22), 3.29-3.24 (m, 2H), 2.94 (t, 2H, J=6.6 Hz), 2.06-1.98 (m, 2H); $^{13}$C NMR (DMSO-d$_6$, 150 MHz) δ 161.4, 154.6, 148.4, 144.1, 133.8, 129.0, 123.5, 117.5, 116.8, 112.3, 104.1, 68.9, 40.8, 26.3, 23.9; HRMS (ES) m/z calcd for $C_{15}H_{15}NO_3$ ([M+Na]$^+$) 280.0950, found 280.0959.

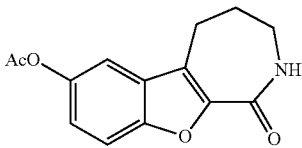 [SMILES: CC(=O)Oc1ccc2oc3c(c2c1)CCCNC3=O]

7-Acetoxy-2,3,4,5-tetrahydro-[1]benzoxolo[2,3-c]azepin-1-one (kb-NB123-36) Yield: 91%; Mp 196-197° C.; IR (ATR, neat) 3193, 3083, 2935, 1750, 1663, 1583, 1207, 1157, 1063 cm$^{-1}$; $^1$H NMR (DMSO-d$_6$, 600 MHz) δ 8.21 (bs, 1H), 7.66 (d, 1H, J=9.0 Hz), 7.47 (d, 1H, J=2.4 Hz), 7.22 (dd, 1H, J=9.0, 2.4 Hz), 3.27 (dd, 2H, J=8.4, 4.8 Hz), 2.94 (t, 2H, J=6.6 Hz), 2.29 (s, 3H), 2.06-1.99 (m, 2H); $^{13}$C NMR (DMSO-d$_6$, 150 MHz) δ 169.7, 161.2, 151.0, 146.3, 144.6, 129.0, 123.5, 122.6, 113.9, 112.3, 40.8, 26.3, 23.8, 20.9; HRMS (EI) m/z calcd for C$_{14}$H$_{13}$NO$_4$ (M$^+$) 259.0845, found 259.0850.

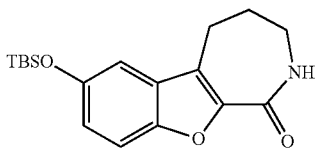 [SMILES: CC(C)(C)[Si](C)(C)Oc1ccc2oc3c(c2c1)CCCNC3=O]

7-(tert-Butyldimethylsilyloxy)-2,3,4,5-tetrahydro-[1]benzoxolo[2,3-c]azepin-1-one (kb-NB77-77). Yield: 91%; Mp 209-212° C.; IR (ATR, neat) 3194, 3085, 2952, 2927, 1655, 1579, 1467, 1252, 1202, 1170 cm$^{-1}$; $^1$H NMR (DMSO-d$_6$, 600 MHz) δ 8.14 (bs, 1H), 7.50 (d, 1H, J=9.0 Hz), 7.06 (d, 1H, J=1.8 Hz), 6.96 (dd, 1H, J=8.4, 2.4 Hz), 3.28-3.23 (m, 2H), 2.93 (t, 2H, J=6.6 Hz), 2.04-1.97 (m, 2H), 0.97 (s, 9H), 0.19 (s, 6H); $^{13}$C NMR (DMSO-d$_6$, 150 MHz) δ 161.3, 151.0, 148.8, 144.2, 129.3, 123.3, 120.4, 112.2, 110.3, 40.8, 26.3, 25.6 (3C), 23.9, 18.0, -4.6 (2C); HRMS (ES) m/z calcd for C$_{18}$H$_{25}$NO$_3$Si ([M+Na]$^+$) 354.1501, found 354.1472.

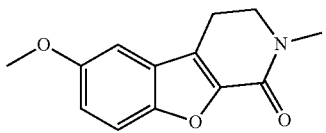

6-Methoxy-2-methyl-2,3,4-trihydrobenzo[b]pyridino[4,3-d]furan-1-one (kb-NB123-37). Yield: 83%; Mp 168-172° C.; IR (ATR, neat) 2920, 1661, 1602, 1485, 1454, 1329, 1212, 1179 cm$^{-1}$; $^1$H NMR (DMSO-d$_6$, 600 MHz) δ 7.57 (d, 1H, J=9.0 Hz), 7.25 (d, 1H, J=2.4 Hz), 7.05 (dd, 1H, J=9.0, 2.4 Hz), 3.81 (s, 3H), 3.69 (t, 2H, J=7.2 Hz), 3.01 (t, 2H, J=7.2 Hz), 2.98 (s, 3H); $^{13}$C NMR (DMSO-d$_6$, 150 MHz) δ 158.5, 156.0, 149.9, 144.5, 123.8, 116.4, 112.9, 103.0, 55.7, 48.6, 33.5, 19.3; HRMS (EI) m/z calcd for C$_{13}$H$_{13}$NO$_3$ (M$^+$) 231.0895, found 231.0899.

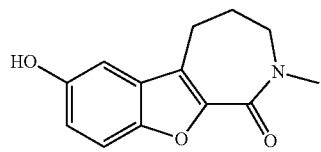 [SMILES: CN1CCCc2c(oc3ccc(O)cc23)C1=O]

7-Hydroxy-2-methyl-3,4,5-trihydro-[1]benzoxolo[2,3-c]azepin-1-one (kb-NB142-25). Yield: 36%; Mp 282-284° C.; IR (ATR, neat) 3186, 1615, 1577, 1452, 1407, 1364, 1325, 1187 cm$^{-1}$; $^1$H NMR (DMSO-d$_6$, 600 MHz) δ 9.36 (s, 1H), 7.41 (d, 1H, J=9.0 Hz), 6.92 (d, 1H, J=2.4 Hz), 6.90 (dd, 1H, J=9.0, 2.4 Hz), 3.52-3.49 (m, 2H), 3.06 (s, 3H), 2.86 (t, 2H, J=6.6 Hz), 2.03-2.09 (m, 2H); $^{13}$C NMR (DMSO-d$_6$, 150 MHz) δ 160.0, 153.5, 147.5, 144.0, 129.0, 122.4, 116.3, 111.9, 104.6, 49.3, 36.2, 25.5, 23.3; HRMS (EI) m/z calcd for C$_{13}$H$_{13}$NO$_3$ (M$^+$) 231.0895, found 231.0899.

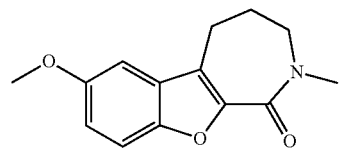

7-Methoxy-2-methyl-3H,4H,5H-azepino[5,6-d]benzo[b]furan-1-one (kb-NB96-04). Yield: 34%; Mp 150-151° C.; IR (ATR, neat) 3008, 2919, 1629, 1579, 1478, 1440, 1428, 1217, 1177 cm$^{-1}$; $^1$H NMR (DMSO-d$_6$, 600 MHz) δ 7.53 (d, 1H, J=9.0 Hz), 7.16 (d, 1H, J=2.4 Hz), 7.05 (dd, 1H, J=9.0, 2.4 Hz), 3.81 (s, 3H), 3.54-3.50 (m, 2H), 3.07 (s, 3H), 2.93 (t, 2H, J=6.6 Hz), 2.11-2.05 (m, 2H); $^{13}$C NMR (DMSO-d$_6$, 150 MHz) δ 159.9, 155.7, 148.3, 144.3, 128.9, 122.9, 116.3, 112.3, 102.7, 55.7, 49.3, 36.2, 25.5, 23.4; HRMS (ES) m/z calcd for C$_{14}$H$_{15}$NO$_3$ ([M+Na]$^+$) 268.0950, found 268.0935.

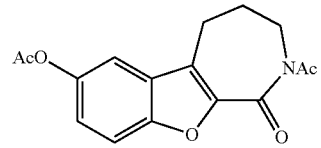

2-Acetyl-1-oxo-3H,4H,5H-azepino[5,6-d]benzo[b]furan-7-yl acetate (kb-NB123-45-1). Yield: 33%; Mp 155-157° C.; IR (ATR, neat) 3069, 2949, 1753, 1699, 1669, 1570, 1402, 1363, 1213, 1168 cm$^{-1}$; $^1$HNMR (DMSO-d$_6$, 600 MHz) δ 7.75 (d, 1H, J=9.0 Hz), 7.61 (s, 1H J=2.4 Hz), 7.31 (dd, 1H, J=9.0, 2.4 Hz), 3.96-3.92 (m, 2H), 3.03 (t, 2H, J=6.0 Hz), 2.45 (s, 3H), 2.30 (s, 3H), 2.08-2.03 (m, 2H); $^{13}$C NMR (DMSO-d$_6$, 150 MHz) δ 171.3, 169.6, 162.3, 151.7, 146.6, 144.5, 128.4, 127.1, 123.1, 114.5, 112.7, 40.9, 26.2, 25.1, 21.6, 20.9; HRMS (EI) m/z calcd for C$_{16}$H$_{15}$NO$_5$ (M$^+$) 301.0950, found 301.0964.

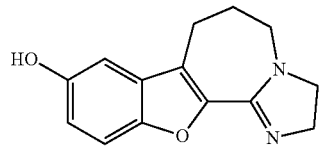 [SMILES: Oc1ccc2oc3c(c2c1)CCCN1CCN=C31]

5H,6H,7H-Benzo[b]2-imidazolino[1',2'-7,1]azepino[5,6-d]furan-9-ol (kb-NB165-15). Yield: 40%; Mp 230-232° C. (dec., brown), 268-270° C. (dec., melts); IR (ATR, neat) 2918, 2871, 2528, 1624, 1590, 1550, 1445, 1392, 1285, 1195 cm$^{-1}$; $^1$H NMR (CD$_3$OD, 600 MHz) δ 7.34 (d, 1H, J=9.6 Hz), 6.92-6.90 (m, 2H), 3.81 (t, 2H, J=10.2 Hz), 3.63 (t, 2H, J=10.2 Hz), 3.44-3.41 (t, 2H, J=4.8 Hz), 2.95 (t, 2H, J=6.0 Hz), 2.22-2.17 (m, 2H); $^{13}$C NMR (CD$_3$OD, 150 MHz) δ 159.8, 155.6, 150.3, 142.4, 130.6, 125.8, 117.9, 112.8, 105.6, 55.0, 52.0, 49.4, 26.5, 25.1; HRMS (EI) m/z calcd for $C_{14}H_{14}N_2O_2$ (M$^+$) 242.1055, found 242.1052.

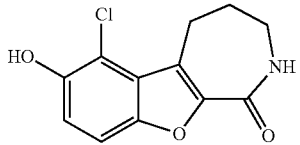 [SMILES: O=C1NCCCc2c1oc1ccc(O)c(Cl)c21]

6-Chloro-7-hydroxy-2,3,4,5-tetrahydro-[1]benzoxolo[2,3-c]azepin-1-one (kb-NB77-88). Yield: 86%; Mp>300° C.; IR (ATR, neat) 3886, 3036 (br), 2928, 1629, 1566, 1428, 1340, 1174 cm$^{-1}$; $^1$H NMR (DMSO-d$_6$, 600 MHz) δ 10.0 (s, 1H), 8.22 (t, 1H, J=4.8 Hz), 7.43 (d, 1H, J=9.0 Hz), 7.10 (d, 1H, J=9.0 Hz), 3.26-3.20 (m, 4H), 2.04-1.98 (m, 2H); $^{13}$C NMR (DMSO-d$_6$, 150 MHz) δ 161.1, 149.5, 147.9, 144.6, 126.0, 123.4, 116.8, 111.4, 110.8, 40.2, 27.0, 26.3; HRMS (ES) m/z calcd for $C_{12}H_{10}ClNO_3$ [M+Na]$^+$, 274.0247, found 274.0226.

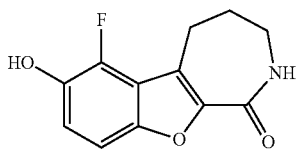 [SMILES: O=C1NCCCc2c1oc1ccc(O)c(F)c21]

6-Fluoro-7-hydroxy-2,3,4,5-tetrahydro-[1]benzoxolo[2,3-c]azepin-1-one (kb-NB96-21). Yield: 29%; Mp>300° C.; IR (ATR, neat) 3197 (br), 2925, 2385, 1625, 1577, 1477, 1437, 1345, 1032 cm$^{-1}$; $^1$H NMR (DMSO-d$_6$, 600 MHz) δ 9.67 (bs, 1H), 8.19 (t, 1H, J=4.2 Hz), 7.26 (d, 1H, J=9.0 Hz), 7.08 (dd, 1H, J=8.6 Hz, $J_{HF}$=8.6 Hz), 3.25 (dd, 2H, J=8.4, 4.8 Hz), 3.09 (t, 2H, J=6.6 Hz), 2.05-1.97 (m, 2H); $^{13}$C NMR (DMSO-d$_6$, 150 MHz) δ 161.1, 147.8 (d, $J_{CF}$=7.5 Hz), 144.3 (d, $J_{CF}$=244 Hz), 143.9, 139.8 (d, $J_{CF}$=10.3 Hz), 121.8 (d, $J_{CF}$=3.5 Hz), 118.3 (d, $J_{CF}$=4.5 Hz), 118.1, 107.4 (d, $J_{CF}$=4.2 Hz), 40.5, 26.7, 25.4; $^{19}$F NMR (DMSO-d$_6$, 400 MHz) δ 149.09 (d, $J_{FH}$=8.4 Hz); HRMS (ES) m/z calcd for $C_{12}H_{10}FNO_3$ ([M+Na]$^+$) 258.0542, found 258.0566.

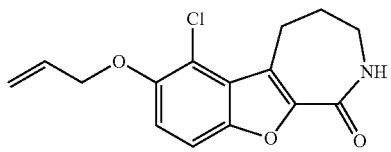 [SMILES: C=CCOc1ccc2oc3c(c2c1Cl)CCCNC3=O]

7-Allyloxy-6-chloro-2,3,4,5-tetrahydro-[1]benzoxolo[2,3-c]azepin-1-one (kb-NB96-50). Yield: 83%; representative experimental data: Mp 192-194° C.; IR (ATR, neat) 3200, 3075, 2928, 1674, 1650, 1573, 1464, 1422, 1259, 1173, 1065 cm$^{-1}$; $^1$H NMR (DMSO-d$_6$, 600 MHz) δ 8.28 (t, 1H, J=4.2 Hz), 7.58 (d, 1H, J=9.0 Hz), 7.33 (d, 1H, J=9.0 Hz), 6.10-6.02 (m, 1H), 5.44 (dd, 1H, J=17.4, 1.8 Hz), 5.28 (dd, 1H, J=9, 1.8 Hz), 4.69 (s, 2H), 3.28-3.21 (m, 4H), 2.05-1.97 (m, 2H); $^{13}$C NMR (DMSO-d$_6$, 150 MHz) δ 160.9, 150.1, 148.9, 145.1, 133.5, 126.2, 123.4, 117.7, 115.2, 115.2, 110.8, 70.4, 30.7, 26.9, 26.8; HRMS (ES) m/z calcd for $C_{15}H_{14}ClNO_3$ ([M+Na]$^+$) 314.0560, found 314.0540.

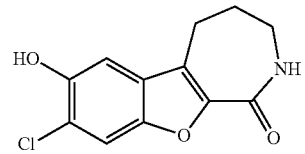 [SMILES: O=C1NCCCc2c1oc1cc(Cl)c(O)cc21]

8-Chloro-7-hydroxy-2,3,4,5-tetrahydro-[1]benzoxolo[2,3-c]azepin-1-one (kb-NB96-47-5). Yield: 5%; representative experimental data: Mp 327-332° C.; IR (ATR, neat) 3293, 3196 (br), 2938, 1652, 1578, 1464, 1437, 1233, 1141 cm$^{-1}$; $^1$H NMR (DMSO-d$_6$, 600 MHz) δ 10.12 (s, 1H), 8.15 (bs, 1H), 7.73 (s, 1H), 7.11 (s, 1H), 3.28-3.22 (m, 2H), 2.89 (t, J=6.6 Hz, 2H), 2.03-1.98 (m, 2H); $^{13}$C NMR (DMSO-d$_6$, 150 MHz) 161.2, 149.4, 147.0, 144.3, 128.0, 123.0, 120.9, 112.7, 105.7, 40.7, 26.3, 23.7; HRMS (ES) m/z calcd for $C_{12}H_{10}ClNO_3$ ([M+Na]$^+$) 274.0247, found 274.0224.

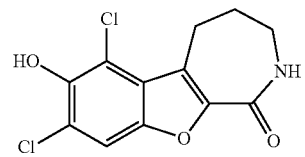

6,8-Dichloro-7-hydroxy-2,3,4,5-tetrahydro-[1]benzoxolo[2,3-c]azepin-1-one (kb-NB96-43). Yield: 73%; Mp 298-301° C.; $^1$H NMR (DMSO-d$_6$, 600 MHz) δ 9.91 (s, 1H), 8.29 (bs, 1H), 7.83 (s, 1H), 3.25-3.20 (m, 4H), 2.04-1.99 (m, 2H); $^{13}$C NMR (DMSO-d$_6$, 150 MHz) δ 160.8, 147.2, 145.7, 145.1, 125.1, 123.4, 123.1, 114.8, 111.7, 40.1, 26.9, 26.1; IR (ATR, neat) 3377, 3077 (br), 2969, 1643, 1568, 1428, 1327, 1233, 1171 cm$^{-1}$; HRMS (ES) m/z calcd for $C_{12}H_9Cl_2NO_3$ [M+Na]$^+$, 307.9857, found 307.9882.

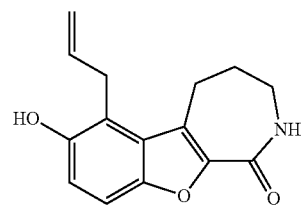 [SMILES: C=CCc1c(O)ccc2oc3c(c12)CCCNC3=O]

6-Allyl-7-hydroxy-2,3,4,5-tetrahydro-[1]benzoxolo[2,3-c]azepin-1-one (kb-NB96-02). Yield: 87%; Mp 255-257° C.; IR (ATR, neat) 3174 (br), 3056, 2920, 1641, 1571, 1476, 1426, 1358, 1343, 1272, 1118 cm$^{-1}$; $^1$H NMR (DMSO-d$_6$, 600 MHz) δ 9.19 (s, 1H), 8.12 (t, 1H, J=4.8 Hz), 7.28 (d, 1H, J=9.0 Hz), 6.98 (d, 1H, J=9.0 Hz), 6.00 (ddt, 1H, J=17.4, 10.2, 5.4 Hz), 4.97 (dd, 1H, J=10.2, 1.2 Hz), 4.79 (dd, 1H, J=17.4, 1.2 Hz), 3.64 (d, 2H, J=5.4 Hz), 3.20 (dd, 2H, J=9.0, 5.4 Hz), 3.14 (t, 2H, J=6.6 Hz), 2.02-1.95 (m, 2H); $^{13}$C NMR (DMSO-d$_6$, 150 MHz) δ 161.6, 150.9, 148.1, 143.8, 137.5, 127.5, 124.0, 118.4, 116.1, 114.8, 109.7, 40.3, 29.1, 27.3, 25.9; HRMS (ES) m/z calcd for $C_{15}H_{15}NO_3$ [M+Na]$^+$, 280.0950, found 280.0960.

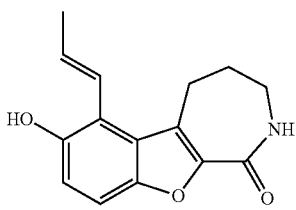 [SMILES: C/C=C/c1c(O)ccc2oc3c(c12)CCCNC3=O]

6-[(E)-2-(Prop-1-enyl)]-7-hydroxy-2,3,4,5-tetrahydro-[1]benzoxolo[2,3-c]azepin-1-one (kb-NB96-30). Yield: 37%; Mp>300° C.; IR (ATR, neat) 3147 (br), 2908, 1644, 1568, 1477, 1417, 1245, 1165 cm$^{-1}$; $^1$H NMR (CD$_3$OD, 600 MHz) δ 7.23 (d, 1H, J=9.0 Hz), 6.97 (d, 1H, J=9.0 Hz), 6.69 (dd, 1H, J=15.6, 1.2 Hz), 6.22 (dq, 1H, J=15.6, 6.6 Hz), 3.40-3.37 (m, 2H), 3.15 (t, 2H, J=6.6 Hz), 2.15-2.10 (m, 2H), 1.95 (dd, 3H, J=6.6, 1.8 Hz); $^{13}$C NMR (CD$_3$OD, 150 MHz) δ 165.42, 152.0, 150.5, 144.4, 133.8, 128.0, 127.9, 124.8, 120.7, 118.2, 111.0, 42.4, 29.5, 28.3, 19.3; HRMS (ES) m/z calcd for C$_{15}$H$_{15}$NO$_3$ ([M+Na]$^+$) 280.0950, found 280.0950.

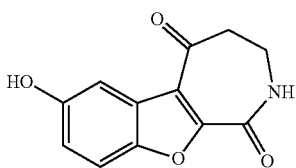 [SMILES: O=C1NCCC(=O)c2c1oc1ccc(O)cc21]

7-Hydroxy-2H,3H,4H-azepino[5,6-d]benzo[b]furan-1,5-dione (kb-NB123-63). Yield: 38%; Mp>300° C.; IR (ATR, neat) 3189 (br), 3072, 2919, 1674, 1645, 1544, 1461, 1349, 1262, 1223 cm$^{-1}$; $^1$H NMR (DMSO-d$_6$, 600 MHz) δ 8.85 (t, 1H, J=4.8 Hz), 7.59 (d, 1H, J=9.0 Hz), 7.58 (d, 1H, J=2.4 Hz), 6.97 (dd, 1H, J=9.0, 2.4 Hz), 3.51-3.46 (m, 2H), 2.93-2.87 (m, 2H); $^{13}$C NMR (DMSO-d$_6$, 150 MHz) δ 195.7, 159.8, 155.4, 151.3, 147.9, 125.5, 119.1, 117.1, 112.4, 107.2, 44.0, 36.0; HRMS (EI) m/z calcd for C$_{12}$H$_9$NO$_4$ (M$^+$) 231.0532, found 231.0530.

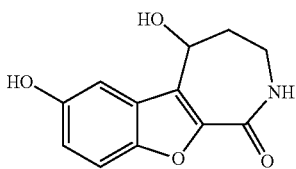

5,7-Dihydroxy-2H,3H,4H,5H-azepino[5,6-d]benzo[b]furan-1-one (kb-NB123-89). Yield: 79%; Mp 280-282° C.; IR (ATR, neat) 3189 (br), 3074, 2918, 1646, 1577, 1455, 1436, 1337, 1178 cm$^{-1}$; $^1$H NMR (CD$_3$OD, 600 MHz) δ 7.39 (d, 1H, J=9.0 Hz), 7.23 (d, 1H, J=2.4 Hz), 6.97 (dd, 1H, J=9.0, 2.4 Hz), 5.14 (d, 1H, J=4.2 Hz), 3.58 (dd, 1H, J=15.0, 10.2 Hz), 3.37-3.32 (m, 1H), 2.32-2.26 (m, 1H), 2.21-2.14 (m, 1H); $^{13}$C NMR (CD$_3$OD, 150 MHz) δ 164.4, 155.0, 150.4, 144.2, 130.1, 127.5, 118.2, 113.0, 107.3, 64.6, 37.3, 37.1; HRMS (EI) m/z calcd for C$_{12}$H$_{11}$NO$_4$ (M$^+$) 233.0688, found 233.0691.

7-Hydroxy-5-[(phenylamino)azamethylene]-2H,3H,4H-azepino[5,6-d]benzo[b]furan-1-one (kb-NB142-05). Yield: 13%; Mp 234-236° C.; IR (ATR, neat) 3218 (br), 2924, 1643, 1600, 1553, 1447, 1341, 1250, 1144 cm$^{-1}$; $^1$H NMR (CD$_3$OD, 600 MHz) δ 7.93 (d, 1H, J=2.4 Hz), 7.41 (d, 1H, J=8.4 Hz), 7.34-7.27 (m, 4H), 7.01 (dd, 1H, J=9, 2.4 Hz), 6.87 (tt, 1H, J=6.0, 1.2 Hz), 3.60-3.57 (m, 2H), 3.00-2.97 (m, 2H); $^{13}$C NMR (CD$_3$OD, 150 MHz) δ 165.7, 155.4, 150.8, 146.8, 144.6, 139.2, 130.2 (2C), 127.5, 124.8, 121.3, 118.1, 114.5 (2C), 112.8, 110.6, 39.0, 32.4; HRMS (EI) m/z calcd for C$_{18}$H$_{15}$N$_3$O$_3$ (M$^+$) 321.1113, found 321.1110.

7-Hydroxy-5-({[(4-methylphenyl)sulfonyl]amino}azamethylene)-2H,3H,4H-azepino[5,6-d]benzo[b]furan-1-one (kb-NB142-11). Yield: 46%; Mp 220-224° C.; IR (ATR, neat) 3212 (br), 1648, 1559, 1448, 1334, 1161 cm$^{-1}$; $^1$H NMR (DMSO-d$_6$, 600 MHz) δ 10.69 (s, 1H), 9.53 (s, 1H), 8.48 (bs, 1H), 7.91 (d, 2H, J=7.2 Hz), 7.55 (s, 1H), 7.45 (d, 1H, J=9.0 Hz), 7.35 (d, 2H, J=7.80 Hz), 6.94 (d, 1H, J=8.4 Hz), 3.33-3.28 (m, 2H), 2.76-2.83 (m, 2H), 2.33 (s, 3H); $^{13}$C NMR (CD$_3$OD, 150 MHz) δ 164.6, 155.8, 151.2, 150.6, 147.0, 145.6, 137.3, 130.6 (2C), 129.2 (2C), 127.0, 122.3, 118.3, 112.7, 110.8, 38.6, 32.9, 21.5; HRMS (EI) m/z calcd for C$_{19}$H$_{17}$N$_3$O$_5$S [M]$^+$, 422.0787, found 422.0817.

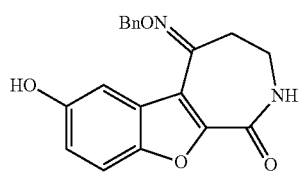

7-Hydroxy-5-[(phenylmethoxy)azamethylene]-2H,3H,4H-azepino[5,6-d]benzo[b]furan-1-one (kb-NB142-10). Yield: 74%; Mp 103-110° C.; IR (ATR, neat) 3217 (br), 2925, 1648, 1552, 1467, 1448, 1351, 1334, 1209, 1185 cm$^{-1}$; $^1$H NMR (CD$_3$OD, 600 MHz) δ 7.66 (t, 1H, J=1.8 Hz), 7.47 (dd, 2H, J=7.8, 0.6 Hz), 7.41 (dd, 1H, J=9.0, 1.2 Hz), 7.37 (dt, 2H, J=7.8, 7.2 Hz), 7.31 (td, 1H, J=7.2, 0.6 Hz), 6.98 (ddd, 1H, J=9, 2.4, 1.8 Hz), 5.33 (s, 2H), 3.45-3.42 (m, 2H), 3.11-3.07 (m, 2H); $^{13}$C NMR (CD$_3$OD, 150 MHz) δ 164.7, 155.7, 153.7, 150.7, 146.9, 139.0, 129.5 (2C), 129.5 (2C), 129.1, 126.8, 120.7, 118.3, 112.9, 110.7, 78.1, 38.7, 31.2.

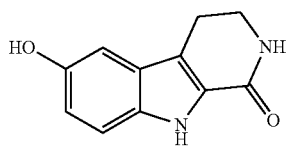 [SMILES: O=C1NCCc2c1[nH]c1ccc(O)cc21]

2,3,4,9-Tetrahydro-6-hydroxy-1H-pyrido[3,4-b]indol-1-one (kb-NB123-59). Yield: 95%; Mp 244-247° C.; IR (ATR, neat) 3391, 3267, 1650, 1618, 1498, 1335, 1207 cm$^{-1}$; $^1$H NMR (DMSO-d$_6$, 600 MHz) δ 11.26 (s, 1H), 8.85 (d, 1H, J=2.4 Hz), 7.47 (s, 1H), 7.18 (dd, 1H, J=8.4, 3.0 Hz), 6.83 (d, 1H, J=2.4 Hz), 6.74 (dd, 1H, J=8.4, 2.4 Hz), 3.50-3.43 (m, 2H), 2.84-2.79 (m, 2H); $^{13}$C NMR (DMSO-d$_6$, 150 MHz) δ 162.0, 150.9, 131.8, 127.5, 125.5, 117.1, 115.1, 113.0, 103.0, 41.2, 20.4; HRMS (EI) m/z calcd for C$_{11}$H$_{10}$N$_2$O$_2$ (M$^+$) 202.0742, found 202.0752.

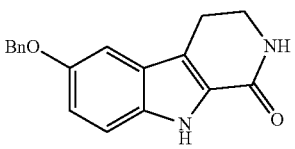

2,3,4,9-Tetrahydro-6-benzyloxy-1H-pyrido[3,4-b]indol-1-one (kb-NB123-52). Yield: 52%; Mp 208-210° C.; IR (ATR, neat) 3233, 2905, 2691, 1567, 1508, 1379, 1242 cm$^{-1}$; $^1$H NMR (DMSO-d$_6$, 600 MHz) δ 11.45 (s, 1H), 7.53 (s, 1H), 7.47 (d, 2H, J=7.2 Hz), 7.39 (t, 2H, J=7.8 Hz), 7.32 (t, 1H, J=7.2 Hz), 7.29 (d, 1H, J=9.0 Hz), 7.17 (d, 1H, J=1.8 Hz), 6.94 (dd, 1H, J=9.0, 1.8 Hz), 5.10 (s, 2H), 3.48 (td, 2H, J=6.6, 1.8 Hz), 2.87 (t, 2H, J=6.6 Hz); $^{13}$C NMR (DMSO-d$_6$, 150 MHz) δ 161.9, 152.6, 137.6, 132.25, 128.4 (2C), 127.3, 127.8, 127.7 (2C), 125.1, 117.7, 115.6, 113.4, 102.4, 69.7, 41.2, 20.5; HRMS (EI$^+$) m/z calcd for C$_{18}$H$_{16}$N$_2$O$_2$ (M$^+$) 292.1212, found 292.1223.

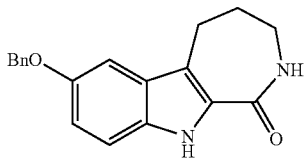 [SMILES: O=C1NCCCc2c1[nH]c1ccc(OCc3ccccc3)cc21]

3,4,5,10-Tetrahydro-7-benzyloxy-azepino[3,4-b]indol-1(2H)-one (kb-NB123-53). Yield: 53%; representative experimental data: IR (ATR, neat) 3227, 3194, 3033, 2920, 1623, 1543, 1478, 1453, 1276, 1197 cm$^{-1}$; $^1$H NMR (DMSO-d$_6$, 600 MHz) δ 11.03 (s, 1H), 7.95 (bs, 1H), 7.50-7.42 (d, 2H), 7.41-7.33 (m, 2H), 7.32-7.29 (m, 2H), 7.11 (bs, 1H), 6.97-6.91 (m, 1H), 5.10 (s, 2H), 3.38-3.34 (m, 2H), 2.96 (bs, 2H), 2.02 (bs, 2H); $^{13}$C NMR (DMSO-d$_6$, 150 MHz) δ 164.1, 152.3, 137.6, 131.3, 128.4, 127.8, 127.7, 127.6, 116.4, 115.6, 113.0, 102.2, 69.7, 41.6, 26.8, 25.4; HRMS (EI) m/z calcd for C$_{19}$H$_{18}$N$_2$O$_2$ (M) 306.1368, found 306.1366.

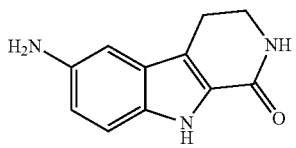 [SMILES: Nc1ccc2[nH]c3c(c2c1)CCNC3=O]

6-Amino-2,3,4,9-tetrahydro-1H-pyrido[3,4-b]indol-1-one (kb-NB142-08). Yield: 69%; Mp 280-282° C. (lit. 280-282° C.) [65]; IR (ATR, neat) 3356, 3230, 1653, 1501, 1327, 1225 cm$^{-1}$; $^1$H NMR (CD$_3$OD, 600 MHz) δ 7.25 (d, 1H, J=8.4 Hz), 6.93 (s, 1H), 6.86 (d, 1H, J=8.4 Hz), 3.61 (t, 2H, J=7.2 Hz), 2.94 (t, 2H, J=7.2 Hz); $^{13}$C NMR (CD$_3$OD, 150 MHz) δ 165.2, 141.1, 134.4, 127.6, 127.2, 120.0, 118.5, 113.9, 105.9, 42.8, 21.6; HRMS (EI) m/z calcd for C$_{11}$H$_{11}$N$_3$O (M$^+$) 201.0902, found 201.0901.

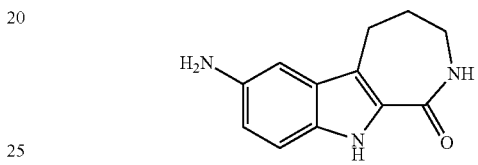

6-Amino-3,4,5,10-tetrahydro-1H-azepino[3,4-b]indol-1(2H)-one (kb-NB142-01). Yield: 68% Mp 202-207° C.; IR (ATR, neat) 3208, 2921, 1618, 1542, 1479, 1450, 1335, 1296 cm$^{-1}$; $^1$H NMR (DMSO-d$_6$, 600 MHz) δ 10.85 (s, 1H), 7.93-7.85 (m, 1H), 7.22-7.17 (m, 1H), 6.86-6.83 (m, 1H), 6.78-6.74 (m, 1H), 6.39 (bs, 2H), 3.30-3.24 (m, 2H), 2.94-2.88 (m, 2H), 2.04-1.98 (m, 2H); $^{13}$C NMR (DMSO-d$_6$, 150 MHz) δ 164.3, 140.7, 130.0, 128.3, 127.0, 115.8, 115.1, 112.4, 101.9, 41.6, 27.0, 25.5; HRMS (EI) m/z calcd for C$_{12}$H$_{13}$N$_3$O (M$^+$) 215.1059, found 215.1062.

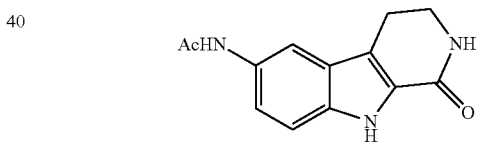

N-(2,3,4,9-Tetrahydro-1-oxo-1H-pyrido[3,4-b]indol-6-yl)-acetamide (kb-NB123-93). Yield: 24%; Mp>300° C. (lit>320° C.) [65]; IR (ATR, neat) 3206, 1642, 1588, 1542, 1484, 1437, 1270 cm$^{-1}$; $^1$H NMR (DMSO-d$_6$, 600 MHz) δ 11.50 (s, 1H), 9.80 (s, 1H), 7.91 (s, 1H), 7.54 (s, 1H), 7.32-7.22 (m, 2H), 3.52-3.45 (m, 2H), 2.89-2.83 (m, 2H), 2.03 (s, 3H); $^{13}$C NMR (DMSO-d$_6$, 150 MHz) δ 167.8, 161.8, 133.8, 131.9, 127.8, 124.6, 118.0, 117.9, 112.4, 109.8, 41.1, 23.9, 20.4; HRMS (EI$^+$) m/z calcd for C$_{13}$H$_{13}$N$_3$O$_2$ (M$^+$) 243.1008, found 243.1009.

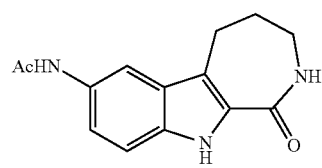 [SMILES: CC(=O)Nc1ccc2[nH]c3c(c2c1)CCCNC3=O]

N-(3,4,5,10)-Tetrahydro-1-oxo-1H-azepino[3,4-b]indol-7-yl)-(2H)-acetamide (kb-NB123-94). Yield: 75%;

Mp>300° C.; IR (ATR, neat) 3270, 1618, 1547, 1477, 1453, 1267 cm$^{-1}$; $^1$H NMR (DMSO-d$_6$, 600 MHz) δ 11.06 (s, 1H), 9.80 (s, 1H), 7.95 (t, 1H, J=4.5 Hz), 7.88 (s, 1H), 7.32-7.25 (m, 2H), 3.30-3.26 (m, 2H), 2.95 (t, J=6.6 Hz, 2H), 2.00-2.06 (m, 5H); $^{13}$C NMR (DMSO-d$_6$, 150 MHz) δ 167.7, 164.1, 132.6, 131.5, 127.8, 127.2, 118.1, 116.6, 112.0, 109.7, 41.5, 26.9, 25.3, 23.9; HRMS (EI) m/z calcd for C$_{14}$H$_{15}$N$_3$O$_2$ (M$^+$) 257.1164, found 257.1166.

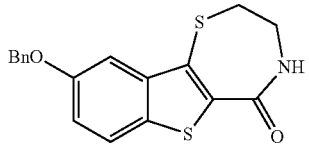

3,4-Dihydro-9-benzyloxy-[1]benzothieno[2,3-f]-1,4-thiazepin-5(2H)-one (kb-NB123-66). Yield: 87%; representative experimental data: Mp 247-249° C.; IR (ATR, neat) 3165, 3037, 1650, 1500, 1282 cm$^{-1}$; $^1$H NMR (DMSO-d$_6$, 600 MHz) δ 8.47 (t, 1H, J=5.6 Hz), 7.90 (d, 1H, J=8.8 Hz), 7.49 (d, 2H, J=7.5 Hz), 7.40 (t, 2H, J=7.7 Hz), 7.36-7.32 (m, 1H), 7.29-7.27 (m, 1H), 7.26-7.23 (m, 1H), 5.20 (s, 2H), 3.64-3.60 (m, 2H), 3.41-3.37 (m, 2H); $^{13}$C NMR (DMSO-d$_6$, 150 MHz) δ 165.1, 156.4, 139.4, 136.9, 133.3, 131.2, 128.5, 127.9, 127.8, 123.8, 118.0, 105.8, 69.6, 42.4, 33.4; HRMS (EI) m/z calcd for C$_{18}$H$_{15}$NO$_2$S$_2$ (M$^+$) 341.0544, found 341.0543.

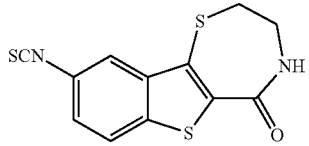

3,4-Dihydro-9-isothiocyanato-[1]benzothieno[2,3-f]-1,4-thiazepin-5(2H)-one (mcf292-05). Yield: 58%; Mp 253.0-253.3° C. (softening point: 251.6° C.); IR (neat) 3260, 3155, 3025, 2922, 2067 (broad), 1633, 1590, 1497, 1469, 1457, 1441, 1420, 1400, 1340, 1321, 1282, 1254, 1241, 1141, 941, 900, 852, 807, 792, 744 cm$^{-1}$; $^1$H NMR (DMSO-d$_6$, 400 MHz) δ 8.56 (bt, 1H, J=5.8 Hz), 8.11 (dd, 1H, J=8.8, 0.4 Hz), 7.80 (dd, 1H, J=2.0, 0.4 Hz), 7.58 (dd, 1H, J=8.8, 2.0 Hz), 3.68-3.61 (m, 2H), 3.46-3.39 (m, 2H); $^{13}$C NMR (DMSO-d$_6$, 100 MHz) δ 164.7, 139.0, 137.7, 134.4, 128.2, 127.2, 124.9, 124.5, 119.7, 42.4, 33.3; EI-MS m/z 292 (M$^+$, 47), 113 (57), 95 (86), 83 (96), 81 (100); HRMS (EI) m/z calcd for C$_{12}$H$_8$N$_2$OS$_3$ 291.9799, found 291.9795.

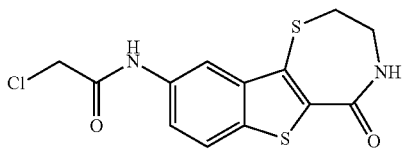 [SMILES: O=C(CCl)Nc1ccc2sc3c(c2c1)SCCNC3=O]

3,4-Dihydro-9-(2-chloroacetamido)-[1]benzothieno[2,3-f]-1,4-thiazepin-5(2H)-one (mcf292-09). Yield: 65%; Mp 229-230° C. (dec.); IR (neat) 3381, 3262, 3155, 3010, 2928, 1668, 1649, 1635, 1571, 1523, 1495, 1467, 1446, 1403, 1338, 1277, 1266, 1243, 1187, 1144, 986, 891, 876, 816, 790, 773, 734, 729 cm$^{-1}$; $^1$H NMR (DMSO-d$_6$, 300 MHz) δ 8.48 (bt, 1H, J=5.8 Hz), 8.25 (d, 1H, J=1.5 Hz), 7.95 (d, 1H, J=8.7 Hz), 7.63 (dd, 1H, J=8.7, 2.1 Hz), 4.29 (s, 2H), 3.70-3.58 (m, 2H), 3.45-3.38 (m, 2H); $^{13}$C NMR (DMSO-d$_6$, 100 MHz) δ 165.0, 164.8, 138.7, 135.9, 133.7, 132.9, 128.2, 123.2, 119.8, 112.4, 43.6, 42.5, 33.2; MS (EI) m/z 328 (40), 326 (M$^+$, 100); HRMS (EI) m/z calcd for C$_{13}$H$_{11}$ClN$_2$O$_2$S$_2$ (M$^+$) 325.9950, found 325.9952.

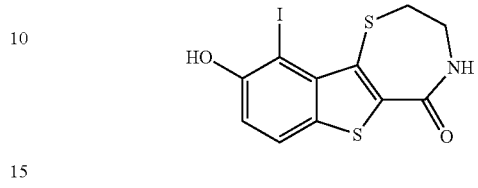

3,4-Dihydro-9-hydroxy-10-iodo-[1]benzothieno[2,3-f]-1,4-thiazepin-5(2H)-one (kb-NB165-31). Yield: 66%; Mp 128° C. (dec.); IR (ATR, neat) 3335, 3071 (br), 1595, 1485, 1387, 1292 cm$^{-1}$; $^1$H NMR (DMSO-d$_6$, 600 MHz) δ 10.52 (s, 1H), 8.54 (t, 1H, J=5.4 Hz), 7.80 (d, 1H, J=8.4 Hz), 7.11 (d, 1H, J=8.4 Hz), 3.47 (q, 2H, J=5.4 Hz), 3.30-3.26 (m, 2H); $^{13}$C NMR (DMSO-d$_6$, 150 MHz) δ 165.1, 155.2, 138.6, 138.3, 132.0, 128.7, 123.9, 115.4, 78.7, 42.2, 35.5; HRMS (EI) m/z calcd for C$_{11}$H$_8$INO$_2$S$_2$ (M$^+$) 376.9041, found 376.9045.

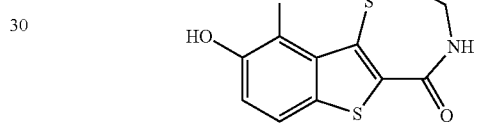

3,4-Dihydro-9-hydroxy-10-bromo-[1]benzothieno[2,3-f]-1,4-thiazepin-5(2H)-one (kb-NB184-52). Yield: 25%; Mp 235-238° C. (dec., brown); IR (ATR, neat) 3350, 3083, 2918, 1595, 1492, 1396, 1303 cm$^{-1}$; $^1$H NMR (DMSO-d$_6$, 600 MHz) δ 10.38 (s, 1H), 8.52 (t, 1H, J=5.4 Hz), 7.78 (d, 1H, J=8.4 Hz), 7.16 (d, 1H, J=8.4 Hz), 3.53 (q, 2H, J=5.4 Hz), 3.31-3.27 (m, 2H); $^{13}$C NMR (DMSO-d$_6$, 150 MHz) δ 164.8, 152.5, 136.5, 136.4, 132.0, 129.1, 122.8, 117.1, 103.3, 42.6, 34.8; HRMS (EI) m/z calcd for C$_{11}$H$_8$BrNO$_2$S$_2$ (M$^+$) 328.9149 found 328.9164.

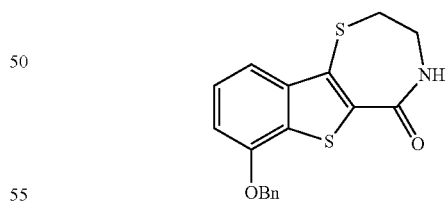

3,4-Dihydro-7-benzyloxy-[1]benzothieno[2,3-f]-1,4-thiazepin-5(2H)-one (kb-NB184-38). Yield: 53%; Mp 213-215° C.; IR (ATR, neat) 3159, 3036, 2923, 1647, 1462, 1257 cm$^{-1}$; $^1$H NMR (DMSO-d$_6$, 600 MHz) δ 8.47 (t, 1H, J=5.4 Hz), 7.49 (d, 2H, J=7.2 Hz), 7.22-7.31 (m, 5H), 7.19 (d, 1H, J=3.0 Hz), 5.35 (s, 2H), 3.68-3.62 (m, 2H), 3.42-3.38 (m, 2H); $^{13}$C NMR (DMSO-d$_6$, 150 MHz) δ 165.0, 152.7, 140.0, 136.6, 132.1, 129.0, 128.6 (2C), 128.0, 127.9, 127.4 (2C), 126.6, 115.4, 18.7, 69.6, 42.6, 33.1; HRMS (EI) m/z calcd for C$_{18}$H$_{15}$NO$_2$S$_2$ (M$^+$) 341.0544, found 341.0543.

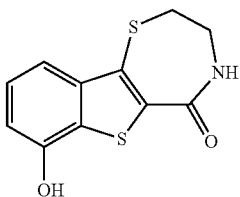 [SMILES: O=C1NCCSc2c1sc1c(O)cccc21]

3,4-Dihydro-7-hydroxy-[1]benzothieno[2,3-f]-1,4-thiazepin-5(2H)-one (kb-NB184-40). Yield: 73%; Mp 269-272° C. (dec., dark brown), 278-281° C. (dec.); IR (ATR, neat) 3255, 3155, 3015, 1620, 1439, 1285 cm$^{-1}$; $^1$H NMR (DMSO-d$_6$, 600 MHz) δ 10.55 (s, 1H), 8.45 (t, 1H, J=5.4 Hz), 7.29 (t, 1H, J=7.8 Hz), 7.24 (d, 1H, J=7.9 Hz), 6.89 (d, 1H, J=7.5 Hz), 3.65-3.60 (m, 2H), 3.40-3.36 (m, 2H); $^{13}$C NMR (DMSO-d$_6$, 150 MHz) δ 165.2, 152.1, 140.3, 131.8, 128.8, 126.65, 126.61, 113.7, 110.8, 42.5, 33.2; HRMS (EI) m/z calcd for C$_{11}$H$_9$NO$_2$S$_2$ (M$^+$) 251.0075, found 251.0066.

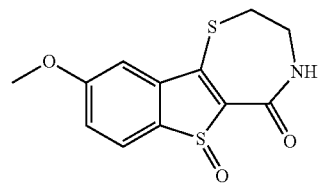

3,4-Dihydro-9-methoxy-6-oxide-[1]benzothieno[2,3-f]-1,4-thiazepin-5(2H)-one (kb-NB184-25). Yield: 58%; Mp 284-287° C.; IR (ATR, neat) 3340, 1506, 1477, 1337, 1248 cm$^{-1}$; $^1$H NMR (DMSO-d$_6$, 600 MHz) δ 7.93 (bs, 1H), 7.60 (d, 1H, J=2.4 Hz), 7.46 (d, 1H, J=9.0 Hz), 7.18 (dd, 1H, J=9.0, 2.4 Hz), 3.86 (s, 3H), 3.75-3.69 (m, 2H), 3.00-2.95 (m, 2H); $^{13}$C NMR (DMSO-d$_6$, 150 MHz) δ 175.7, 158.1, 146.5, 127.5, 123.7, 123.2, 117.3, 107.4, 102.0, 55.8, 42.6, 22.7; MS (ESI) m/z 282 ([M+H]$^+$); HRMS (EI) m/z calcd for C$_{12}$H$_{11}$NO$_3$S$_2$ (M)$^+$ 281.0180, found 281.0180.

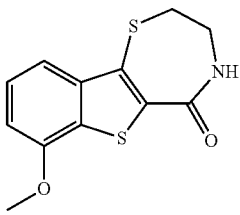 [SMILES: COc1cccc2c3c(sc12)C(=O)NCCS3]

3,4-Dihydro-7-methoxy-[1]benzothieno[2,3-f]-1,4-thiazepin-5(2H)-one (kb-NB184-44). Yield: 99%; Mp 220-224° C.; IR (ATR, neat) 3163, 3032, 2932, 1634, 1467, 1261 cm$^{-1}$; $^1$H NMR (DMSO-d$_6$, 600 MHz) δ 8.48 (t, 1H, J=4.8 Hz), 7.44 (t, 1H, J=7.8 Hz), 7.37 (d, 1H, J=7.8 Hz), 7.09 (d, 1H, J=7.8 Hz), 3.96 (s, 3H), 3.66-3.61 (m, 2H), 3.42-3.37 (m, 2H); $^{13}$C NMR (DMSO-d$_6$, 150 MHz) δ 165.0, 153.8, 139.9, 132.0, 128.9, 127.4, 126.7, 115.1, 107.2, 55.9, 42.5, 33.1; HRMS (ES) m/z calcd for C$_{12}$H$_{11}$NO$_2$S$_2$ ([M+Na]$^+$) 288.0129, found 288.0102.

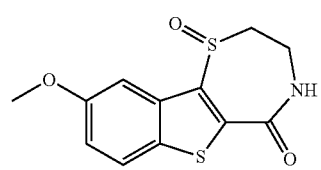

3,4-Dihydro-9-methoxy-1-oxide-[1]benzothieno[2,3-f]-1,4-thiazepin-5(2H)-one (kb-NB184-45). Yield: 54%; Mp 215-217° C.; IR (ATR, neat) 3156, 3020, 2915, 1638, 1507 cm$^{-1}$; $^1$H NMR (DMSO-d$_6$, 600 MHz) δ 8.99 (bs, 1H), 8.03 (d, 1H, J=9.0 Hz), 7.59 (d, 1H, J=2.4 Hz), 7.25 (dd, 1H, J=8.4, 2.4 Hz), 3.94-3.87 (m, 1H), 3.87 (s, 3H), 3.59-3.51 (m, 3H); $^{13}$C NMR (DMSO-d$_6$, 150 MHz) δ 162.3, 157.7, 141.9, 140.1, 133.6, 131.4, 124.0, 117.9, 104.6, 55.5, 50.4, 32.6; HRMS (EI) m/z calcd for C$_{12}$H$_{11}$NO$_3$S$_2$ (M$^+$) 281.0180, found 281.0177.

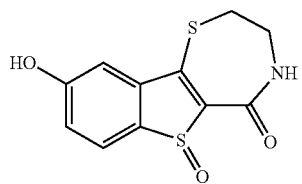 [SMILES: O=C1NCCSC2=C1S(=O)c1ccc(O)cc12]

3,4-Dihydro-9-hydroxy-6-oxide-[1]benzothieno[2,3-f]-1,4-thiazepin-5(2H)-one (kb-NB184-22). Yield: 80%; Mp 160-163° C. (dec., brown) 280-282° C. (dec., melts); IR (ATR, neat) 3369 (br), 1648, 1608, 1577, 1452, 1335, 1245, 998 cm$^{-1}$; $^1$H NMR (DMSO-d$_6$, 600 MHz) δ 9.90 (bs, 1H), 7.80 (bs, 1H), 7.47 (s, 1H), 7.33 (d, 1H, J=9.0 Hz), 7.04 (d, 1H, J=9.0 Hz), 3.73-3.63 (m, 2H), 3.00-2.90 (m, 2H); $^{13}$C NMR (DMSO-d$_6$, 150 MHz) δ 175.8, 156.2, 146.6, 127.3, 123.5, 121.7, 118.1, 109.5, 101.7, 42.6, 22.7; MS (ESI) m/z 268 ([M+H]$^+$).

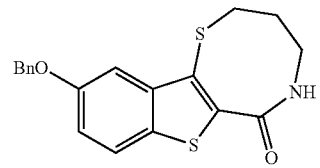

2,3,4,5-Tetrahydro-10-benzyloxybenzo[b]thieno[2,3-f]-1,5-thiazocin-6-one (kb-NB165-89). Yield: 42%; Mp 198-199° C.; IR (ATR, neat) 3162, 3033, 2937, 1644, 1619, 1600, 1497, 1384, 1274, 1193 cm$^{-1}$; $^1$H NMR (DMSO-d$_6$, 600 MHz) δ 8.02 (bs, 1H), 7.90-7.84 (m, 1H), 7.51-7.45 (m, 2H), 7.43-7.37 (m, 2H), 7.36-7.31 (m, 1H), 7.26-7.19 (m, 2H), 5.20 (s, 2H), 3.50-3.43 (m, 2H), 3.30-3.24 (m, 2H), 1.92-1.89 (m, 2H); $^{13}$C NMR (DMSO-d$_6$, 150 MHz) δ 164.8, 156.4, 138.7, 136.9, 130.3, 128.5, 128.5, 127.9, 127.7, 127.4, 123.6, 117.3, 105.8, 69.6, 30.5, 27.4; MS (EI) m/z 356 (23), 355 (M$^+$, 100), 357 (12); HRMS (EI) m/z calcd for C$_{19}$H$_{17}$NO$_2$S$_2$ (M$^+$) 355.0701, found 355.0689.

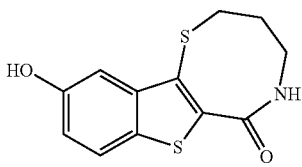 [SMILES: O=C1NCCCSc2c1sc1ccc(O)cc21]

2,3,4,5-Tetrahydro-10-hydroxybenzo[b]thieno[2,3-f]-1,5-thiazocin-6-one (kb-NB165-92). Yield: 92%; Mp 139-142° C.; IR (ATR, neat) 3256 (br), 3169 (br), 1615, 1492, 1444, 1182 cm$^{-1}$; $^1$H NMR (DMSO-d$_6$, 600 MHz) δ 9.71 (s, 1H), 7.97 (t, 1H, J=7.8 Hz), 7.74 (d, 1H, J=8.6 Hz), 7.09 (s, 1H), 6.98 (d, 1H, J=8.6 Hz), 3.50-3.43 (m, 2H), 3.30-3.23 (m, 2H), 1.92-1.85 (m, 2H); $^{13}$C NMR (DMSO-d$_6$, 150 MHz) δ 164.9, 155.3, 139.0, 128.4, 127.0, 123.4, 117.1, 106.8, 30.5, 27.3; MS (EI) m/z 266 (15), 265 (M$^+$, 100), 267 (11); HRMS (EI) m/z calcd for C$_{12}$H$_{11}$NO$_2$S$_2$ (M$^+$) 265.0231, found 265.0230.

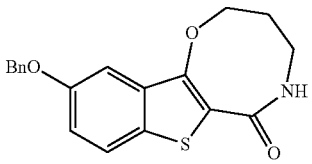 [SMILES: O=C1NCCCOc2c1sc1ccc(OCc3ccccc3)cc21]

2,3,4,5-Tetrahydro-10-benzyloxybenzo[b]thieno[2,3-f]-1,5-oxazocin-6-one (kb-NB184-36). Yield: 51%; Mp 195-200° C.; IR (ATR, neat) 2912 (br), 2298, 1637, 1607, 1528, 1455, 1422, 1222 cm$^{-1}$; $^1$H NMR (DMSO-d$_6$, 600 MHz) δ 8.00 (t, 1H, J=7.2 Hz), 7.75 (d, 1H, J=8.4 Hz), 7.47 (d, 2H, J=7.8 Hz), 7.40 (t, 2H, J=7.8 Hz), 7.37-7.32 (m, 1H), 7.26 (d, 1H, J=2.4 Hz), 7.18 (dd, 1H, J=8.4, 2.4 Hz), 5.17 (s, 2H), 4.49 (t, 2H, J=5.4 Hz), 3.40-3.35 (m, 2H), 1.87 (quint, 2H, J=5.4 Hz); $^{13}$C NMR (DMSO-d$_6$, 150 MHz) δ 165.1, 156.2, 149.2, 137.0, 133.5, 129.2, 128.5 (2C), 127.9, 127.6 (2C), 123.8, 118.3, 112.0, 104.7, 69.5, 68.6, 37.8, 29.2; HRMS (ESI) m/z calcd for C$_{19}$H$_{17}$NO$_3$S ([M+Na]$^+$) 362.0827, found 362.0809.

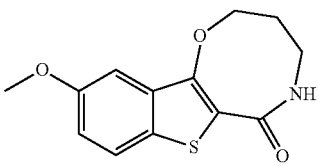 [SMILES: COc1ccc2sc3c(c2c1)OCCCNC3=O]

2,3,4,5-Tetrahydro-10-methoxybenzo[b]thieno[2,3-f]-1,5-oxazocin-6-one (kb-NB184-57). Yield: 35%; Mp 233-237° C.; IR (ATR, neat) 3154, 3027, 2919, 1631, 1467, 1422, 1220 cm$^{-1}$; $^1$H NMR (DMSO-d$_6$, 600 MHz) δ 8.00 (t, 1H, J=6.6 Hz), 7.73 (d, 1H, J=9.0 Hz), 7.15 (d, 1H, J=2.4 Hz), 7.09 (dd, 1H, J=9.0, 2.4 Hz), 4.50 (t, 2H, J=5.4 Hz), 3.81 (s, 3H), 3.42-3.32 (m, 2H), 1.92-1.84 (m, 2H); $^{13}$C NMR (DMSO-d$_6$, 150 MHz) δ 165.1, 157.2, 149.2, 133.5, 128.9, 123.7, 117.9, 112.0, 103.3, 68.6, 55.3, 37.8, 29.2; HRMS (ESI) m/z calcd for C$_{13}$H$_{13}$NO$_3$S ([M+Na]$^+$) 286.0514, found 286.0510.

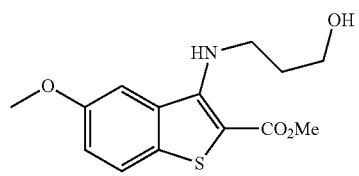 [SMILES: COC(=O)c1sc2ccc(OC)cc2c1NCCCO]

Methyl 3-(3-hydroxypropylamino)-5-methoxybenzo[b]thiophene-2-carboxylate (kb-NB184-80). Yield: 71%; Mp 116-120° C.; IR (ATR, neat) 3481, 2921, 1627, 1578, 1440, 1224 cm$^{-1}$; $^1$H NMR (CDCl$_3$, 600 MHz) δ 7.60 (d, 1H, J=8.4 Hz), 7.57 (d, 1H, J=2.4 Hz), 7.11 (dd, 1H, J=8.4, 2.4 Hz), 3.87 (s, 3H), 3.87 (s, 3H), 3.90-3.87 (m, 2H), 3.84 (t, 1H, J=6.6 Hz), 1.99 (quint., 2H, J=6.6 Hz), 1.25 (s, 2H); $^{13}$C NMR (CDCl$_3$, 150 MHz) δ 166.4, 157.0, 151.8, 133.3, 133.0, 124.4, 118.1, 107.5, 101.9, 60.5, 55.8, 51.7, 43.7, 33.6; HRMS (ESI) m/z calcd for C$_{14}$H$_{17}$NO$_4$S (M$^+$) 295.0878, found 295.0879.

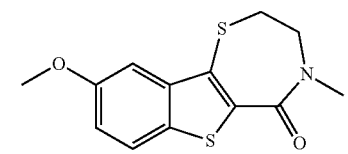

2,3-Dihydro-4-Methyl-9-methoxy-[1]benzothieno[2,3-f]-1,4-thiazepin-5(2H)-one (kb-NB165-16). Yield: 71%; Mp 160-161° C.; IR (ATR, neat) 2928, 1625, 1598, 1497, 1397, 1207 cm$^{-1}$; $^1$H NMR (CD$_3$OD, 600 MHz) δ 7.77 (d, 1H, J=9.0 Hz), 7.33 (d, 1H, J=2.4 Hz), 7.14 (dd, 1H, J=9.0, 2.4 Hz), 3.88 (s, 3H), 3.86-3.83 (m, 2H), 3.53-3.50 (m, 2H), 3.22 (s, 3H); $^{13}$C NMR (CD$_3$OD, 150 MHz) δ 167.5, 159.6, 141.2, 136.0, 133.2, 129.2, 124.5, 118.9, 105.7, 56.0, 51.3, 35.8, 35.0; HRMS (EI) m/z calcd for C$_{13}$H$_{13}$NO$_2$S$_2$ (M$^+$) 279.0388, found 279.0386.

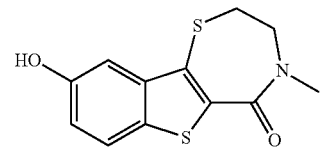 [SMILES: CN1CCSc2c(sc3ccc(O)cc23)C1=O]

2,3-Dihydro-4-methyl-9-hydroxy-[1]benzothieno[2,3-f]-1,4-thiazepin-5-one (kb-NB165-17). Yield: 56%; Mp 265-268° C.; IR (ATR, neat) 3193 (br), 2384, 1610, 1587, 1494, 1401 cm$^{-1}$; $^1$H NMR (CD$_3$OD, 600 MHz) δ 7.69 (d, 1H, J=9.0 Hz), 7.26 (d, 1H, J=2.4 Hz), 7.03 (dd, 1H, J=9.0, 2.4 Hz), 3.85 (t, 2H, J=5.4 Hz), 3.50 (t, 2H, J=5.4 Hz), 3.21 (s, 3H); $^{13}$C NMR (CD$_3$OD, 150 MHz) δ 167.6, 156.9, 141.5, 135.5, 131.9, 128.9, 124.4, 118.8, 108.5, 51.4, 35.8, 34.9; HRMS (EI) m/z calcd for C$_{12}$H$_{11}$NO$_2$S$_2$ (M$^+$) 265.0231, found 265.0235.

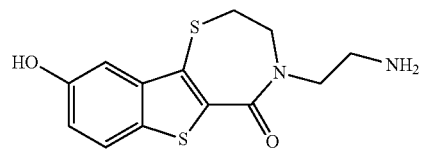 [SMILES: NCCN1CCSc2c(sc3ccc(O)cc23)C1=O]

2,3-Dihydro-4-(2-aminoethyl)-9-hydroxy-[1]benzothieno[2,3-f]-1,4-thiazepin-5-one (kb-NB165-75). Yield: quant.; Mp 250-254° C.; IR (ATR, neat) 3251 (br), 2918 (br), 1579, 1500, 1427, 1178 cm$^{-1}$; $^1$H NMR (DMSO-d$_6$, 600 MHz) δ 9.82 (s, 1H), 7.99 (bs, 2H), 7.79 (d, 1H, J=9.0 Hz), 7.18 (d, 1H, J=2.4 Hz), 7.04 (dd, 1H, J=9.0, 2.4 Hz), 3.85 (t, 2H, J=4.8 Hz), 3.73 (t, 2H, J=6.0 Hz), 3.48 (t, 2H, J=4.8 Hz), 3.10-3.03 (m, 2H); $^{13}$C NMR (DMSO-d$_6$, 150 MHz) δ 165.2, 155.5, 139.5, 133.6, 129.3, 127.0, 123.7, 117.9, 107.1, 48.3, 45.7, 37.3, 32.8; HRMS (EI) m/z calcd for C$_{13}$H$_{14}$N$_2$O$_2$S$_2$ [M]$^+$ 294.0497, found 294.0492.

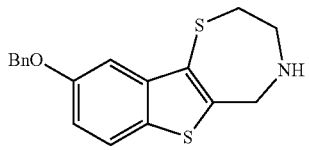 [SMILES: c1ccc(COc2ccc3sc4c(c3c2)SCCNC4)cc1]

2,3,4,5-Tetrahydro-9-benzyloxy-[1]benzothieno[2,3-f]-1,4-thiazepine (kb-NB165-81). Yield: 15%; Mp 144-145° C.; IR (ATR, neat) 2915, 1596, 1443, 1270, 1192 cm$^{-1}$; $^1$H NMR (CD$_3$OD, 600 MHz) δ 7.67 (d, J=9.0 Hz, 1H), 7.48 (d, 2H, J=7.2 Hz), 7.38 (t, 2H, J=7.2 Hz), 7.37-7.30 (m, 2H), 7.06 (dd, 1H, J=9.0, 2.4 Hz), 5.14 (s, 2H), 4.14 (s, 2H), 3.44-3.41 (m, 2H), 2.82-2.79 (m, 2H); $^{13}$C NMR (CD$_3$OD, 150 MHz) δ 158.4, 145.0, 142.6, 138.7, 131.3, 129.5 (2C), 128.9, 128.7 (2C), 128.0, 124.2, 116.5, 107.2, 71.3, 55.3, 35.5; MS (EI) m/z 327 (M$^+$); HRMS (EI) m/z calcd for C$_{18}$H$_{17}$NOS$_2$ (M$^+$) 327.0752, found 327.0749.

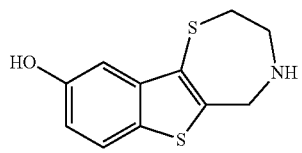 [SMILES: Oc1ccc2sc3c(c2c1)SCCNC3]

2,3,4,5-Tetrahydro-9-hydroxy-[1]benzothieno[2,3-f]-1,4-thiazepine (kb-NB165-83). Yield: 70%; Mp 182-184° C. (dec., dark brown); IR (ATR, neat) 2947 (br), 2920, 1598, 1436, 1183 cm$^{-1}$; $^1$H NMR (CD$_3$OD, 600 MHz) δ 7.59 (d, 1H, J=9.0 Hz), 7.16 (d, 1H, J=2.4 Hz), 6.88 (dd, 1H, J=9.0, 2.4 Hz), 4.18 (s, 2H), 3.49-3.45 (m, 2H), 2.86-2.81 (m, 2H); $^{13}$C NMR (CD$_3$OD, 150 MHz) δ 156.5, 143.9, 142.8, 130.1, 127.9, 124.1, 116.1, 108.4, 55.2, 35.1; MS (EI) m/z 238 (14), 237 (M$^+$, 100), 239 (10); HRMS (EI) m/z calcd for C$_{11}$H$_{11}$NOS$_2$ (M$^+$) 237.0282, found 237.0289.

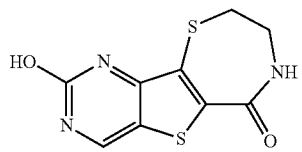 [SMILES: O=C1NCCSc2c1sc1cnc(O)nc21]

2-Hydroxy-7H,8H,9H-1,4-thiazepino[7',6'-5,4]thiopheno[3,2-d]pyrimidin-6-one (hydrochloride salt, kmg-NB4-69A). Yield: 85%; Mp 335.9° C. (dec); IR (ATR) cm$^{-1}$ 3452, 3267, 3176, 2591, 2032, 1912, 1700, 1623, 1463, 1240; $^1$H NMR (DMSO-d$_6$, 400 MHz) δ 9.20 (s, 1H), 8.74 (t, 1H, J=6.2 Hz), 7.79 (bs, 1H), 3.68-3.60 (m, 2H), 3.39-3.32 (m, 2H); $^{13}$C NMR (DMSO-d$_6$, 100 MHz) δ 164.0, 161.0, 159.7, 153.6, 140.9, 128.4, 119.6, 42.6, 32.2; HRMS (ESI) m/z calcd for C$_9$H$_8$N$_3$O$_2$S$_2$ ([M+H]$^+$) 254.0058, found 254.0041.

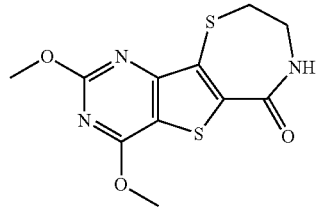 [SMILES: COc1nc(OC)c2sc3c(c2n1)SCCNC3=O]

2,4-Dimethoxy-7H,8H,9H-1,4-thiazepino[7',6'-5,4]thiopheno[3,2-d]pyrimidin-6-one (kmg-NB5-13C). Yield: 77%; Mp 288.0° C. (dec); IR (ATR, neat) 3321, 1642, 1579, 1545, 1491, 1476, 1458, 1346, 1331, 1206 cm$^{-1}$; $^1$H NMR (DMSO-d$_6$, 500 MHz) δ 8.65 (t, 1H, J=5.7 Hz), 4.09 (s, 3H), 3.96 (s, 3H), 3.69-3.64 (m, 2H), 3.38-3.34 (m, 2H); $^{13}$C NMR (DMSO-d$_6$, 125 MHz) δ 165.5, 164.1, 163.5, 159.9, 135.9, 130.3, 111.5, 54.74, 54.72, 42.8, 31.8.

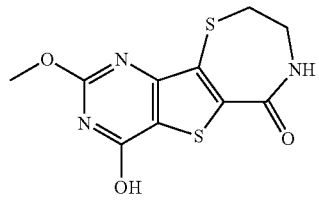 [SMILES: COc1nc(O)c2sc3c(c2n1)SCCNC3=O]

4-Hydroxy-2-methoxy-7H,8H,9H-1,4-thiazepino[7',6'-5,4]thiopheno[3,2-d]pyrimidin-6-one (kmg-NB5-15A). Yield: 77%; Mp 295.0° C. (dec); IR (ATR, neat) 3266, 3170, 2740, 1674, 1646, 1603, 1465, 1407, 1316 cm$^{-1}$; $^1$H NMR (DMSO-d$_6$, 400 MHz) δ 12.72 (s, 1H), 8.56 (t, 1H, J=5.2 Hz), 3.94 (s, 3H), 3.66-3.60 (m, 2H), 3.32-3.28 (m, 2H); $^{13}$C NMR (DMSO-d$_6$, 125 MHz) δ 164.0, 158.4, 156.8, 153.8, 135.7, 130.6, 118.6, 54.9, 42.7, 31.9; MS (EI) m/z 283 (M$^+$, 100).

Inhibition of Protein Kinase D

The inventive compounds inhibit pan—PKD as evidenced by an ex vivo assay set forth by a published protocol. See Sharlow, E. R., et. al., *J Biol Chem*, 283: 33516-33526, (2008). The assay established the concentration of inhibitor that is required to reduce PKD1 activity by 50% (IC$_{50}$), as shown in Table 2 above.

In Vitro Inhibition of Protein Kinase D1

The radiometric PKD kinase assay was carried out by co-incubating 0.5 μCi γ-32P-ATP (PerkinElmer, Boston, Mass.), 20 μM ATP, 50 ng purified recombinant human PKD (PKD1, PKD2, PKD3) proteins, and 2.5 μg Syntide-2 (Sigma) in 50 μl kinase buffer that contains 50 mM Tris-HCl, pH 7.5, 4 mM MgCl$_2$, 10 mM β-mercaptoethanol. The reaction was carried out under sub-saturation conditions, such that the initial rate was within linear kinetic range. The reaction mixture was incubated at 30° C. for 10 min, followed by spotting 25 μl of the mix onto a Whatman P81 filter paper (Whatman Inc, Clifton, N.J.). The filter papers were then washed three times in 0.5% phosphoric acid, air-dried, and counted using a Beckman LS6500 multi-purpose scintillation counter (Beckman, Fullerton, Calif.).

Cellular Inhibition of Protein Kinase D1

The compound to be tested was dissolved in DMSO at an initial concentration of 10 mM. LNCaP prostate cancer cells were pre-treated with DMSO or increasing concentrations of the compound for 45 min, followed by treatment with or without 100 nM phorbol 12-myristate 13-acetate (PMA), an activator of PKD, for 20 min. The cells were harvested for Western blot analysis.

Briefly, cells were lysed in lysis buffer containing 200 mM Tris-HCl, pH 7.4, 100 μM 4-(2-aminoethyl)benzenesulfonyl fluoride, 1 mM EGTA, and 1% Triton X-100. Protein concentration was determined using the BCA Protein Concentration Assay reagent kit (Pierce). Equal amounts of protein were subjected to SDS-PAGE followed by electrotransfer to nitrocellulose membranes. Membranes were blocked with 5% nonfat milk in Tris-buffered saline and then probed with primary antibodies for p-S916-PKD1 (Millipore), p-S744/748-PKD1 (Cell Signaling Technology), or GAPDH (Enzo), followed by anti-mouse or anti-rabbit secondary antibodies conjugated to horseradish peroxidase (Bio-Rad). The bands were detected by incubating with the enhanced chemiluminescence (ECL) Western blotting detection reagent (Amersham Biosciences) and exposing to X-ray films.

IMAP-Based Counter-Screening Assays

Automated, highthroughput screening (HTS) formatted IMAP-based AKT fluorescent polarization assay (AKT FP), and PLK1 and CAK TR-FRET assays were used to assess the specificity of the PKD analogs as previously described. See Sharlow, E. R., et. al., *J. Biol Chem,* 283: 33516-33526, (2008). For the PLK2 IMAP TR-FRET assay, PLK2 kinase reactions were generated by the stepwise addition of a 3-fold excess concentration of substrate/ATP (1650 nM/105 μM), analog, and PLK2 enzyme (1.02 milliunits/μL). PLK2 kinase reactions were incubated for 150 min at room temperature and stopped with the addition of an IMAP binding reagent supplemented with terbium. Assay plates were then incubated overnight. Analysis was performed as described in the literature. Id.

The PLK2 substrate (FAM-LKKLTRRASFSGQ) was obtained from Molecular Devices (Sunnyvale, Calif.). H-89 was used as a positive inhibitory control compound in the assays. A 10 point concentration range for each compound to be tested was used to determine $IC_{50}$ values. The maximum concentration of a particular compound used in this assay was either 50 μM, or 100 μM, depending on the solubility of the individual compounds. Each experiment was assayed in triplicate and data is represented as average $IC_{50} \pm SD$. The $IC_{50}$ determinations for each analog evaluated in the IMAP (PLK2, PLK1, CAK, and AKT) formats were conducted within the linear range of the captured signal readout.

Methods of Treatment and Uses

The inventive compounds are useful for inhibiting the expression or activity of PKD1. The enzymes of the protein kinase D family play an important role in the control of various cellular response, including cell proliferation, cell survival, signaling, gene expression, cell motility and immune responses to name a few. Aberrant PKD expression and activity contribute to various pathological conditions including cancer and cardiac hypertrophy. Thus, inhibitors of protein kinase D are candidate therapeutics for treating various disorders, including cancer and cardiac hypertrophy.

In one aspect of the invention, the invention provides methods and uses for inhibiting PKD1, by contacting the cell with at least one inventive compound or composition. More specifically, the invention provides a method for treating or preventing a disease or condition associated with abnormal expression or activity of PKD1 in a subject, by administering to the subject a therapeutically effective amount of at least one compound according to Formula I.

According to the inventive methodology the subject or patient undergoing treatment is a mammal selected from the group consisting of human, dog, cat, horse, cow sheep, reptile and lamb. For instance, the methods and uses described herein are suitable for medical use in humans.

As stated above, the inventive compounds can be formulated using pharmaceutically acceptable buffers, excipients, preservatives, coloring agents, and taste enhancing agents. The inventive formulations administer a therapeutically effective amount of the inventive compound to a subject in any number of ways. The therapeutically effective amount of the compound can depend upon the amounts and types of excipients, the amounts and specific types of active ingredients in a dosage form, the route by which the compound is to be administered to patients. However, typical dosage forms of the invention comprise a compound, or a pharmaceutically acceptable salt, solvate, hydrate, or prodrug.

Typical dosage levels generally range from about 0.001 to about 100 mg per kg patient body weight per day which can be administered in single or multiple doses. An exemplary dosage is about 0.01 to about 25 mg/kg per day or about 0.05 to about 10 mg/kg per day. In other embodiments, the dosage level is from about 0.01 to about 25 mg/kg per day, about 0.05 to about 10 mg/kg per day, or about 0.1 to about 5 mg/kg per day.

A dose may be given as a single once-a-day dose or, alternatively, as divided doses throughout the day, optionally taken with food. In one embodiment, the daily dose is administered twice daily in equally divided doses. A daily dose range can be from about 5 mg to about 500 mg per day, such as, for example, between about 10 mg and about 300 mg per day. In managing the patient, the therapy can be initiated at a lower dose, perhaps from about 1 mg to about 25 mg, and increased if necessary up to from about 200 mg per day to about 2000 mg per day, administered as either a single dose or multiple doses, depending on the patient's global response.

Depending on the disease to be treated and the subject's condition, the compounds of the invention may be administered by oral, parenteral (e.g., intramuscular, intraperitoneal, intravenous (IV), infusion via implant, through the IV route, such as central lining), or sublingual, routes of administration. The compounds can be formulated alone or in combination with other suitable therapeutic agents, in suitable dosage unit formulations containing conventional nontoxic pharmaceutically acceptable carriers, adjuvants and vehicles, as described above, that are appropriate for each route of administration. The invention also contemplates administration of the compounds of the invention in a depot formulation, in which the active ingredient is released over a defined time period.

What is claimed is:

1. A compound according to Formula I,

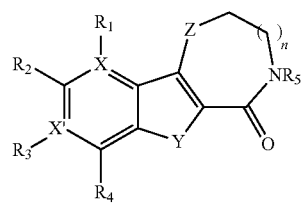

wherein
- R₁, R₂, R₃, and R₄ are each independently selected from the group consisting of hydrogen, straight or branched chain (C₁-C₆)alkyl, (C₂-C₆)alkene, halogen, —OH, —OR', —OC(O)CH₃, (C₁-C₆)alkoxy, —N₃, —NR'R", isocyanate, isothiocyanate, straight or branched (C₁-C₆)haloalkyl and straight or branched (C₁-C₆)haloalkoxy;
- R₅ is selected from the group consisting of hydrogen, a straight or branched chain (C₁-C₆)alkyl, (C₁-C₆) alkylene-NH₂, (C₁-C₆)alkoxy, and —C(O)—(C₁-C₆)alkyl;
- each of X and X' is a —C— or —N—;
- Y is —S—;
- Z is —S—; and
- n is 1;
- wherein R', R", Rᵃ, Rᵇ and Rᵈ are each independently selected from the group consisting of H, straight or branched (C₁-C₆)alkyl, (C₂-C₆)alkene, (C₂-C₆)alkenyloxy, halogen, —OH, —OC(O)CH₃, —C(O)CH₃, —C(O)CH₂-halide, straight or branched (C₁-C₆)haloalkyl, and benzyl,
- wherein R₁ is only present when X is C, and R₃ is only present when X' is C,
- or a pharmaceutically acceptable salt, stereoisomer, tautomer, or prodrug thereof.

2. The compound according to claim 1, wherein R₂ is —OH.

3. The compound according to claim 1, wherein R₂ is (C₁-C₆)alkoxy.

4. The compound according to claim 3, wherein R₂ is methoxy.

5. The compound according to claim 1, wherein R₂ is an azide.

6. The compound according to claim 1, wherein each of X and X' is —N—.

7. The compound according to claim 1, wherein each of X and X' is —CH—.

8. The compound according to claim 1, wherein R₂ is H.

9. The compound according to claim 1 that is selected from the following table:

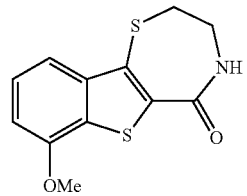 [SMILES: COc1cccc2c3c(sc12)C(=O)NCCS3]

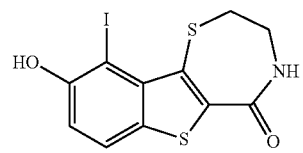 [SMILES: O=C1NCCSc2c1sc1ccc(O)c(I)c21]

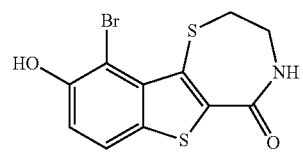 [SMILES: O=C1NCCSc2c1sc1ccc(O)c(Br)c21]

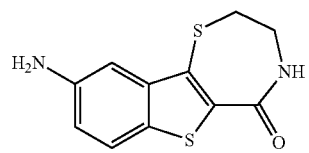

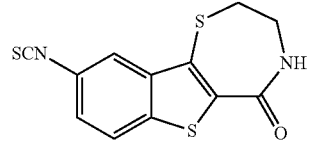 [SMILES: Nc1ccc2sc3c(c2c1)SCCNC3=O]

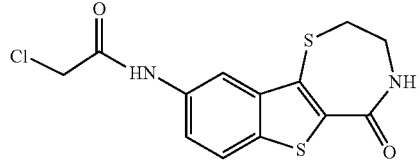 [SMILES: O=C(CCl)Nc1ccc2sc3c(c2c1)SCCNC3=O]

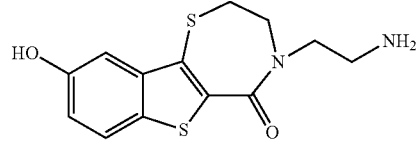 [SMILES: NCCN1CCSc2c(sc3ccc(O)cc23)C1=O]

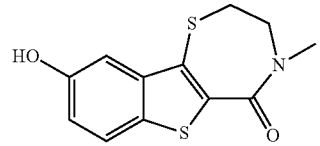 [SMILES: CN1CCSc2c(sc3ccc(O)cc23)C1=O]

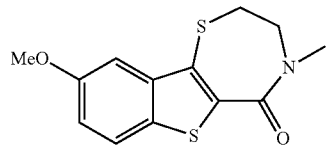 [SMILES: COc1ccc2sc3c(c2c1)SCCN(C)C3=O]

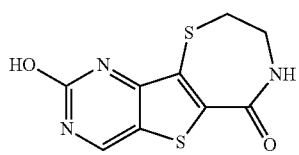 [SMILES: O=C1NCCSc2c1sc1cnc(O)nc21]
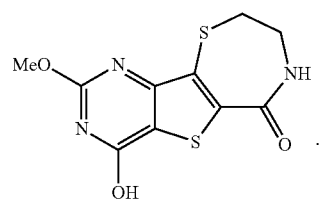
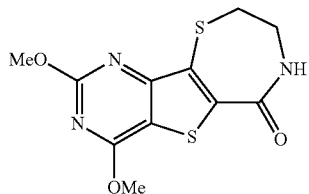 [SMILES: COc1nc(OC)c2sc3c(c2n1)SCCNC3=O]
10. A pharmaceutical composition comprising a therapeutically effective amount of at least one compound according to claim 1, or a pharmaceutically acceptable salt, tautomer, or prodrug thereof; and a pharmaceutically acceptable carrier.
11. A method for inhibiting PKD1 in a cell, comprising contacting the cell with at least one compound according to claim 1.
* * * * *